United States Patent
Janssen et al.

(10) Patent No.: US 10,548,660 B2
(45) Date of Patent: Feb. 4, 2020

(54) ABLATION APPARATUS AND SYSTEM TO LIMIT NERVE CONDUCTION

(71) Applicant: Serene Medical, Inc., San Ramon, CA (US)

(72) Inventors: William M. Janssen, San Mateo, CA (US); James P. Newman, Redwood City, CA (US); Ammon B. Balaster, Boulder, CO (US); Jeffrey M. Buske, Broomfield, CO (US)

(73) Assignee: SERENE MEDICAL, INC., San Ramon, CA (US)

( * ) Notice: Subject to any disclaimer, the term of this patent is extended or adjusted under 35 U.S.C. 154(b) by 0 days.

(21) Appl. No.: 14/852,983

(22) Filed: Sep. 14, 2015

(65) Prior Publication Data

US 2016/0066984 A1 Mar. 10, 2016

Related U.S. Application Data

(63) Continuation of application No. 13/570,138, filed on Aug. 8, 2012, now Pat. No. 9,168,091, which is a
(Continued)

(51) Int. Cl.
*A61B 18/12* (2006.01)
*A61B 18/14* (2006.01)
(Continued)

(52) U.S. Cl.
CPC ...... *A61B 18/1477* (2013.01); *A61B 18/1206* (2013.01); *A61B 18/16* (2013.01);
(Continued)

(58) Field of Classification Search
CPC . A61B 18/1477; A61B 18/1206; A61B 18/12; A61B 2018/00434;
(Continued)

(56) References Cited

U.S. PATENT DOCUMENTS

| | | |
|---|---|---|
| 3,104,879 A | 9/1963 | Jetton |
| 4,306,111 A | 12/1981 | Lu et al. |

(Continued)

FOREIGN PATENT DOCUMENTS

| | | |
|---|---|---|
| JP | 2000-515774 | 11/2000 |
| WO | WO 1997/021387 | 6/1997 |

(Continued)

OTHER PUBLICATIONS

Ellis and Bakala (1998) "Anatomy of the motor innervation of the corrugator supercilli muscle: clinical significance and development of a new surgical technique for frowning" Jour. Otolaryngology 27(4):222-227.

(Continued)

*Primary Examiner* — Aaron F Roane
(74) *Attorney, Agent, or Firm* — Duane Morris LLP

(57) ABSTRACT

A method of managing a system of minimally invasive surgery. The management method includes providing a practitioner with a minimally invasive surgery system including a controller. One or more use parameters is stored to memory associated with the controller. In addition, an electrosurgical probe having its own memory is provided to mate with the remaining elements of the system. Complementary use parameters are stored in the memory of the probe. The management method also includes communicating and comparing the use parameters of the controller with the complementary use parameters of the probe and managing the use of the electrosurgical probe according to the use parameters.

18 Claims, 36 Drawing Sheets

Related U.S. Application Data continuation of application No. 12/612,360, filed on Nov. 4, 2009, now Pat. No. 9,283,031, which is a continuation-in-part of application No. 11/460,870, filed on Jul. 28, 2006, now abandoned, and a continuation-in-part of application No. 11/559,232, filed on Nov. 13, 2006, now abandoned, which is a continuation-in-part of application No. 10/870,202, filed on Jun. 17, 2004, now abandoned.

(51) Int. Cl.
  *A61B 90/30* (2016.01)
  *A61B 18/16* (2006.01)
  *A61B 90/00* (2016.01)
  *A61B 18/00* (2006.01)
  *A61B 17/00* (2006.01)

(52) U.S. Cl.
  CPC .... *A61B 90/30* (2016.02); *A61B 2017/00482* (2013.01); *A61B 2018/0072* (2013.01); *A61B 2018/00434* (2013.01); *A61B 2018/00577* (2013.01); *A61B 2018/00702* (2013.01); *A61B 2018/00732* (2013.01); *A61B 2018/00761* (2013.01); *A61B 2018/00988* (2013.01); *A61B 2018/1467* (2013.01); *A61B 2018/162* (2013.01); *A61B 2090/0803* (2016.02); *A61B 2090/0814* (2016.02); *A61B 2090/3937* (2016.02)

(58) Field of Classification Search
  CPC .......... A61B 2018/00577; A61B 2018/00702; A61B 2018/0072; A61B 2018/00732; A61B 2018/00761; A61B 2018/1467; A61B 2018/162
  USPC ......................................................... 606/41
  See application file for complete search history.

(56) References Cited

U.S. PATENT DOCUMENTS

| | | | |
|---|---|---|---|
| 4,411,266 A | 10/1983 | Cosman | |
| 4,674,499 A | 6/1987 | Pao | |
| 4,896,671 A | 1/1990 | Cunningham et al. | |
| 4,936,842 A | 6/1990 | D'Amelio et al. | |
| 5,078,717 A | 1/1992 | Parins | |
| 5,098,431 A | 3/1992 | Rydell | |
| 5,122,137 A | 6/1992 | Lennox | |
| 5,364,393 A | 11/1994 | Auth et al. | |
| 5,397,339 A | 3/1995 | Desai | |
| 5,403,311 A | 4/1995 | Abele et al. | |
| 5,439,224 A | 8/1995 | Bertonicino | |
| 5,450,846 A | 9/1995 | Goldreyer | |
| 5,454,809 A | 10/1995 | Janssen | |
| 5,458,597 A | 10/1995 | Edwards et al. | |
| 5,540,681 A | 7/1996 | Strul et al. | |
| 5,540,734 A | 7/1996 | Zabara | |
| 5,674,191 A | 10/1997 | Edwards et al. | |
| 5,697,536 A | 12/1997 | Eggers et al. | |
| 5,697,882 A | 12/1997 | Eqqers et al. | |
| 5,697,909 A | 12/1997 | Eqqers et al. | |
| 5,749,914 A | 5/1998 | Janssen | |
| 5,782,826 A | 7/1998 | Swanson | |
| 5,843,019 A | 12/1998 | Eqqers et al. | |
| 5,895,386 A | 4/1999 | Odell et al. | |
| 5,897,552 A | 4/1999 | Edwards et al. | |
| 5,906,614 A | 5/1999 | Stern et al. | |
| 5,971,983 A | 10/1999 | Lesh | |
| 6,004,319 A | 12/1999 | Goble et al. | |
| 6,016,452 A | 1/2000 | Kasevich | |
| 6,023,638 A | 2/2000 | Swanson | |
| 6,096,035 A | 8/2000 | Sodhi et al. | |
| 6,099,524 A | 8/2000 | Lipson et al. | |
| 6,102,907 A | 8/2000 | Smethers et al. | |
| 6,122,549 A | 9/2000 | Sharkey et al. | |
| 6,139,545 A * | 10/2000 | Utley | A61B 5/053 606/34 |
| 6,146,380 A | 11/2000 | Racz et al. | |
| 6,149,620 A | 11/2000 | Baker et al. | |
| 6,149,647 A | 11/2000 | Tu et al. | |
| 6,159,194 A | 12/2000 | Eqqers et al. | |
| 6,161,048 A | 12/2000 | Sluijter et al. | |
| 6,165,169 A | 12/2000 | Panescu et al. | |
| 6,165,173 A | 12/2000 | Kamdar et al. | |
| 6,197,021 B1 | 3/2001 | Panescu et al. | |
| 6,241,753 B1 | 6/2001 | Knowlton | |
| 6,246,912 B1 | 6/2001 | Sluijter et al. | |
| 6,259,945 B1 | 7/2001 | Epstein et al. | |
| 6,259,952 B1 | 7/2001 | Sluijter et al. | |
| 6,292,695 B1 | 9/2001 | Webster et al. | |
| 6,312,428 B1 | 11/2001 | Eggers et al. | |
| 6,337,994 B1 | 1/2002 | Stoianovici et al. | |
| 6,379,349 B1 | 4/2002 | Mueller et al. | |
| 6,381,498 B1 | 4/2002 | Knowlton | |
| 6,384,384 B1 | 5/2002 | Conolly | |
| 6,405,732 B1 | 6/2002 | Edwards et al. | |
| 6,428,537 B1 | 8/2002 | Swanson et al. | |
| 6,432,986 B2 | 8/2002 | Levin | |
| 6,466,817 B1 | 10/2002 | Kaula et al. | |
| 6,524,308 B1 * | 2/2003 | Muller | A61B 18/1206 606/27 |
| 6,564,096 B2 | 5/2003 | Mest | |
| 6,569,028 B1 | 5/2003 | Nichols | |
| 6,575,969 B1 | 6/2003 | Rittman, III et al. | |
| 6,618,626 B2 | 9/2003 | West, Jr. et al. | |
| 6,663,627 B2 | 12/2003 | Francischelli et al. | |
| 6,706,016 B2 | 3/2004 | Cory et al. | |
| 6,719,754 B2 | 4/2004 | Underwood et al. | |
| 6,735,475 B1 | 5/2004 | Whitehurst et al. | |
| 6,740,084 B2 | 5/2004 | Ryan | |
| 6,749,604 B1 | 6/2004 | Eggers et al. | |
| 6,911,027 B1 | 6/2005 | Edwards et al. | |
| 6,989,010 B2 | 1/2006 | Francischelli et al. | |
| 7,115,124 B1 | 10/2006 | Xiao | |
| 7,177,677 B2 | 2/2007 | Kaula et al. | |
| 7,282,049 B2 | 10/2007 | OrszuJak et al. | |
| 7,300,435 B2 | 11/2007 | Wham et al. | |
| RE40,279 E | 4/2008 | Sluijter et al. | |
| 8,512,715 B2 | 8/2013 | Papay | |
| 8,521,295 B2 | 8/2013 | Laufer | |
| 8,666,498 B2 | 3/2014 | Newman | |
| 2002/0065481 A1 | 5/2002 | Cory et al. | |
| 2002/0065567 A1 | 5/2002 | Kodera | |
| 2002/0068930 A1 | 6/2002 | Tasto et al. | |
| 2002/0111618 A1 | 8/2002 | Stewart et al. | |
| 2002/0120260 A1 | 8/2002 | Morris et al. | |
| 2004/0059328 A1 | 3/2004 | Daniel et al. | |
| 2005/0033137 A1 | 2/2005 | Oral et al. | |
| 2005/0177211 A1 | 8/2005 | Leung et al. | |
| 2005/0283148 A1 | 12/2005 | Janssen et al. | |
| 2006/0089688 A1 | 4/2006 | Panescu | |
| 2006/0153876 A1 | 7/2006 | Sanders | |
| 2007/0060921 A1 | 3/2007 | Janssen et al. | |
| 2007/0167943 A1 | 7/2007 | Janssen et al. | |
| 2008/0051859 A1 | 2/2008 | Sharkey et al. | |
| 2009/0062886 A1 | 3/2009 | O'Handley et al. | |
| 2010/0114095 A1 | 5/2010 | Janssen et al. | |
| 2010/0114191 A1 | 5/2010 | Newman | |
| 2012/0071811 A1 | 3/2012 | Ansarinia | |
| 2013/0046292 A1 | 2/2013 | Janssen et al. | |
| 2014/0058372 A1 | 2/2014 | Belson | |
| 2014/0303617 A1 | 10/2014 | Shimada | |

FOREIGN PATENT DOCUMENTS

| | | |
|---|---|---|
| WO | WO 2003/068095 | 8/2003 |
| WO | WO 2008/011730 | 1/2008 |
| WO | WO 2008/014465 | 10/2008 |

(56) References Cited

OTHER PUBLICATIONS

Guyuron et al. (1995) "Corrugator supercilli muscle resection through blepharaplasty incision" Plastic Reconstructive Surg., 95(4):691-696.
Hernandez-Zendejas & Guerrero-Santos (1994) "Percutaneous Selective Radio-Frequency Neuroblation in Plastic Surgery" Aesthetic Plastic Surgery, 18:4148.
J. Jankovic el al., "Therapeutic uses of botulinum toxin." (1991) The New England Journal of Medicine 324:1186-1194.
Utley and Goode (1999) "Radiofrequency Ablation of the Nerve to the Corrugator Muscle for Elimination of Glabellar Furrowing" Archives of Facial Plastic Surgery, Jan.-Mar. 1999 VI pp. 46-48.

\* cited by examiner

ABLATION APPARATUS AND SYSTEM TO LIMIT NERVE CONDUCTION

CROSS-REFERENCE TO RELATED APPLICATIONS

This application is a continuation of U.S. patent application Ser. No. 13/570,138 filed Aug. 8, 2012, which is a continuation of U.S. patent application Ser. No. 12/612,360, filed on Nov. 4, 2009, which is a continuation of U.S. patent application Ser. No. 11/460,870, filed on Jul. 28, 2006, and also a continuation of U.S. patent application Ser. No. 11/559,232, filed Nov. 13, 2006, both of which are a continuation-in-part applications of U.S. patent application Ser. No. 10/870,202, filed Jun. 17, 2004, each of which applications are hereby incorporated by reference.

TECHNICAL FIELD

The present invention relates to a method and device used in the field of Minimally Invasive Surgery (or MIS) for interrupting the flow of signals through nerves. These nerves may be rendered incapable of transmitting signals either on a temporarily (hours, days or weeks) or a permanent (months or years) basis. One embodiment of the apparatus includes a single puncture system which features electrodes capable of creating areas of nerve destruction, inhibition and ablation.

BACKGROUND OF THE INVENTION

The human nervous system is used to send and receive signals. The pathway taken by the nerve signals conveys sensory information such as pain, heat, cold and touch and command signals which cause movement (e.g. muscle contractions).

Often extraneous, undesired, or abnormal signals are generated (or are transmitted) along nervous system pathways. Examples include, but are not limited to, the pinching of a minor nerve in the back, which causes extreme back pain. Similarly, the compression or other activation of certain nerves may cause referred pain. Certain diseases also may compromise the lining of nerves such that signals are spontaneously generated, which can cause a variety of maladies, from seizures to pain or (in extreme conditions) even death. Abnormal signal activations can cause many other problems including (but not limited to) twitching, tics, seizures, distortions, cramps, disabilities (in addition to pain), other undesirable conditions, or other painful, abnormal, undesirable, socially or physically detrimental afflictions.

In other situations, the normal conduction of nerve signals can cause undesirable effects. For example in cosmetic applications the activation of the corrugator supercilli muscle causes frown lines which may result in permanent distortion of the brow (or forehead); giving the appearance of premature aging. By interruption of the corrugator supercilli activation nerves, this phenomenon may be terminated. Direct surgical interruption of nerves is however a difficult procedure.

Traditional electrosurgical procedures use either a unipolar or bipolar device connected to that energy source. A unipolar electrode system includes a small surface area electrode, and a return electrode. The return electrode is generally larger in size, and is either resistively or capacitively coupled to the body. Since the same amount of current must flow through each electrode to complete the circuit; the heat generated in the return electrode is dissipated over a larger surface area, and whenever possible, the return electrode is located in areas of high blood flow (such as the biceps, buttocks or other muscular or highly vascularized area) so that heat generated is rapidly carried away, thus preventing a heat rise and consequent burns of the tissue. One advantage of a unipolar system is the ability to place the unipolar probe exactly where it is needed and optimally focus electrosurgical energy where desired. One disadvantage of a unipolar system is that the return electrode must be properly placed and in contact throughout the procedure. A resistive return electrode would typically be coated with a conductive paste or jelly. If the contact with the patient is reduced or if the jelly dries out, a high-current density area may result, increasing the probability for burns at the contact point.

Typical bipolar electrode systems are generally based upon a dual surface de ice (such as forceps, tweezers, pliers and other grasping type instruments) where the two separate surfaces can be brought together mechanically under force. Each opposing surface is connected to one of the two source connections of the electrosurgical generator. Subsequently, the desired object is held and compressed between the two surfaces. When the electrosurgical energy is applied, it is concentrated (and focused) so that tissue can be cut, desiccated, burned, killed, stunned, closed, destroyed or sealed between the grasping surfaces. Assuming the instrument has been designed and used properly, the resulting current flow will be constrained within the target tissue between the two surfaces. One disadvantage of a conventional bipolar system is that the target tissue must be properly located and isolated between these surfaces. Also, to reduce extraneous current flow the electrodes can not make contact with other tissue, which often requires visual guidance (such as direct visualization, use of a scope, ultrasound or other direct visualization methods) so that the target tissue is properly contained within the bipolar electrodes themselves, prior to application of electrical energy.

In recent years, considerable efforts have been made to refine sources of RF or electrical energy, as well as devices for applying electrical energy to specific targeted tissue. Various applications such as tachyarrhythmia ablation have been developed, whereby accessory pathways within the heart conduct electrical energy in an abnormal pattern. This abnormal signal flow results in excessive and potentially lethal cardiac arrhythmias. RF ablation delivers electrical energy in either a bipolar or unipolar configuration utilizing a long catheter, similar to an electrophysiology (EP) catheter. An EP catheter consisting of a long system of wires and supporting structures normally introduced via an artery or vein which leads into the heart is manipulated using various guidance techniques, such as measurement of electrical activity, ultrasonic guidance, and/or X-ray visualization, into the target area. Electrical energy is then applied and the target tissue is destroyed.

A wide variety of technology in the development of related systems, devices and EP products has already been disclosed. For example, U.S. Pat. No. 5,397,339, issued Mar. 14, 1995, describes a multipolar electrode catheter, which can be used to stimulate, ablate, obtain intercardiac signals, and can expand and enlarge itself inside the heart. Other applications include the ability to destroy plaque formations in the interior of lumens within the body; using RF energy applied near, or at the tip of catheters such as described in U.S. Pat. Nos. 5,454,809 and 5,749,914. In these applications a more advanced catheter which is similar to the EP catheters described above contains an array of electrodes that are able to selectively apply energy in a specific direction. Such devices allow ablation and removal of asymmetric deposits or obstructions within lumens in the body, U.S. Pat. No. 5,098,431 discloses another catheter based system for removing obstructions from within blood vessels. Parins, in U.S. Pat. No. 5,078,717 discloses yet another catheter to selectively remove stenotic lesions from the interior walls of blood vessels. Auth in U.S. Pat. No. 5,364,393 describes a modification of the above technologies whereby a small guide wire which goes through an angioplasty device and is typically 110 cm or longer has an electrically energized tip, which creates a path to follow and thus guides itself through the obstructions.

In applications of a similar nature, catheters which carry larger energy bursts, for example from a defibrillator into chambers of the heart have been disclosed. These catheters are used to destroy both tissues and structures as described in Cunningham (U.S. Pat. No. 4,896,671).

Traditional treatments for the elimination of glabellar furrowing, have included surgical forehead lifts, resection of corrugator supercilli muscle, as described by Guyuron, Michelow and Thomas in pi Corrugator Supercilli Muscle Resection Through BlepharoplastyIncision, Plastic Reconstructive Surgery 95 691-696 (1995). Also, surgical division of the corrugator supercilli motor nerves is used and was described by Ellis and Bakala in Anatomy of the Motor Innervation of the Corrugator Supercilli Muscle: Clinical Significance and Development of a New Surgical Technique for Frowning, J Otolaryngology 27, 222-227 (1998). These techniques described are highly invasive and sometimes temporary as nerves regenerate over time and repeat or alternative procedures are required.

More recently, a less invasive procedure to treat glabellar furrowing involves injection of botulinum toxin (Botox) directly into the muscle. This produces a flaccid paralysis and is best described in The New England Journal of Medicine, 324:1186-1194 (1991). While minimally invasive, this technique is predictably transient; so, it must be re-done every few months.

Specific efforts to use RF energy via a two needle bipolar system has been described by Hernandez-Zendejas and Guerrero-Santos in: Percutaneous Selective Radio-Frequency Neuroablation in Plastic Surgery, Aesthetic Plastic Surgery, 18:41 pp 41-48 (1994) The authors described a bipolar system using two parallel needle type electrodes. Utley and Goode described a similar system in Radiofrequency Ablation of the Nerve to the Corrugator Muscle for Elimination of Glabellar Furrowing, Archives of Facial Plastic Surgery, January-March, 99, VI P 46-48, and U.S. Pat. No. 6,139,545. These systems were apparently unable to produce permanent results possibly because of limitations inherent in a two needle bipolar configuration. Thus, as is the case with Botox, the parallel needle electrode systems would typically require periodic repeat procedures.

There are many ways of properly locating an active electrode near the target tissue and determining if it is in close proximity to the nerve. Traditional methods in the cardiac ablation field have included stimulation by using either unipolar and bipolar energy by means of a test pacemaker pulse prior to the implantation of a pacemaker or other stimulation device. A method of threshold analysis called the strength duration curve has been used for many years. This curve consists of a vertical axis (or Y-axis) typically voltage, current, charge or other measure of amplitude, and has a horizontal axis (or X-axis) of pulse duration (typically in milliseconds). Such a curve is a rapidly declining line, which decreases exponentially as the pulse width is increased.

Various stimulation devices have been made and patented. One process of stimulation and ablation using, a two-needle system is disclosed in U.S. Pat. No. 6,139,545. The stimulation may also be implemented negatively, where tissue not responsive to stimulation is ablated as is described in U.S. Pat. No. 5,782,826 (issued Jul. 21, 1998).

SUMMARY OF THE INVENTION

One aspect of the present invention is an electrosurgical probe including a probe body which defines a longitudinal probe axis. Thus the probe resembles a single needle and can be placed into tissue through a single opening. The electrosurgical probe also includes a first and second conductive electrode, each disposed along the probe axis. The surface area of the first conductive electrode is, in this aspect of the invention, greater than the surface area of the second conductive electrode. The ratio of the surface area of the first conductive electrode to the surface area of the second conductive electrode may be equal to or greater than 3:1 or equal to or greater than 8:1. The ratio of the surface area of the first conductive electrode to the surface area of the second conductive electrode may be adjustable.

The electrosurgical probe of the subject invention may further include a stimulation energy source in electrical communication with either the first or the second conductive electrode. Similarly, the electrosurgical probe may also include an ablation energy source communicating with either the first or second conductive electrode. A switch may be provided for the selective connection of the stimulation energy source or the ablation energy source to at least one of the conductive electrodes. Either the first or the second conductive electrode may be nearer the point of the electrosurgical probe at one end of the probe axis.

Another aspect of the present invention is an electrosurgical probe including a probe body defining a longitudinal probe axis, an active electrode operatively associated with the probe body at a first location along the probe axis, a stimulation electrode associated with the probe body at a second location along the probe axis and a return electrode operatively associated with the probe body at a third location along the probe axis. The stimulation electrode may be positioned between the active and return electrodes. The electrosurgical probe of this embodiment may further include a stimulation energy source in electrical communication with the stimulation electrode. The stimulation energy source may provide variable stimulation current. Either the active electrode, the return electrode or both may be connected to a ground for the stimulation energy source. Alternatively, a separate ground may be employed. This aspect of the present invention may also include an ablation energy source connected to the active electrode. The ablation energy source may be configured to provide variable ablation energy.

Another aspect of the present invention is an electrosurgical probe also having a probe body defining a longitudinal probe axis. At least three electrodes will be associated with the probe body at distinct and separate locations along the probe axis. A stimulation energy source connected to at least one of the electrodes is also included.

The stimulation energy source of this embodiment of the present invention may be configured to provide variable stimulation energy in addition, the stimulation energy source may be selectively connected by means of a switch to at least one or more of the various electrodes. Similarly, a ground for the stimulation energy source may be selectively connected to one or more of the electrodes.

Another aspect of the present invention is a method for positioning an electrosurgical probe. The method includes providing an electrosurgical probe such as those described immediately above, inserting the electrical surgical probe to a first position within tissue containing a target nerve and applying stimulation energy to an electrode. Upon the application of stimulation energy, a first response of a muscle associated with the target nerve may be observed. Thereupon, the electrosurgical probe may be moved to a second position and a second application of stimulation energy may be undertaken. The method further includes observing a second response of a muscle associated with the target nerve and comparing the second response with the first response. The method may also include varying the level of stimulation energy between the first and second applications of stimulation current. If the electrosurgical probe provided to implement the method has a third electrode, stimulation energy may be applied to a select third electrode as well. Certain advantages will be observed with respect to positioning the electrosurgical probe if stimulation energy is sequentially applied to first, second, third and subsequent electrodes.

Another aspect of the present invention is a method of managing a system of minimally invasive surgery. The management method includes providing, a practitioner with a minimally invasive surgery system including a controller. One or more use parameters is stored to memory associated with the controller. In addition, an electrosurgical probe having its own memory is provided to mate with the remaining elements of the system. Complementary use parameters are stored in the memory of the probe. The management method also includes communicating and comparing the use parameters of the controller with the complementary use parameters of the probe and managing the use of the electrosurgical probe according to the use parameters. The use parameters may include items such as a practitioner identification designation, a controller identification designation and a permitted therapeutic protocol. Other use parameters may be devised. This aspect of the present invention may also include maintaining a probe use flag in the electrosurgical probe memory.

Another aspect of the present invention is a system for minimally invasive surgery including a controller associated with memory, an electrosurgical probe associated with memory, a communication link between the controller and the probe and means for comparing use parameters stored in the memory of the controller with complementary use parameters stored in the electrosurgical probe. In addition, the system includes means for managing use of the electrosurgical probe according to the use parameters.

Another aspect of the present invention is an electrosurgical probe having a probe body defining a longitudinal probe axis with multiple conductive electrodes operatively disposed along the probe axis. The probe also includes a stimulation current source in electrical communication with at least one conductive electrode and a blunt tip operatively disposed at a first end of the probe.

Another aspect of the present invention is an electrosurgical probe including a probe body defining a longitudinal probe axis, multiple conductive electrodes operatively disposed along the probe axis, and a stimulation current source in electrical communication with at least one of the conductive electrodes. This aspect of the present invention further includes a handle operatively associated with the probe body and a switch operatively associated with the handle. The switch is selected so that selective actuation of the switch may increase or decrease the application of stimulation current to at least one conductive electrode. The switch may also be configured such that an alternative actuation of the switch allows the application of ablation current to at least one conductive electrode.

Another aspect of the present invention is a system for minimally invasive surgery including an electrosurgical probe, a source of ablation current in electrical communication with the electrosurgical probe and apparatus for automatically delivering a therapeutic quantity of energy from the source of ablation current to the electrosurgical probe. The therapeutic quantity of energy may include a select waveform, a select energy application duration, or a predetermined power profile that varies over time. Other attributes of the therapeutic quantity of energy are possible.

Another aspect of the present invention is a method of minimally invasive surgery which includes automatically supplying a therapeutic quantity of energy from a source of ablation current such as is described above.

Certain terms used herein are defined as follows:

Medical Terms

Corrugator supercili muscles—skeletal muscles of the forehead that produce brow depression and frowning.

Cepressor anguli oris—skeletal muscle of the corner of the mouth that produces depression of the corner of the mouth.

Depressor labii inferioris—skeletal muscle of the lower lip that causes the lip to evert and depress downward.

Dystonias—medical condition describing an aberrant contraction of a skeletal muscle which is involuntary.

Frontalis—skeletal muscle of the forehead that produces brow elevation or raising of the eyebrows.

Hyperhidrosis—condition of excessive sweat production.

Masseter—skeletal muscle of the jaw that produces jaw closure and clenching.

Mentalis—skeletal muscle of the lower lip and chin which stabilizes lower lip position.

Orbicularis oculio—skeletal muscle of the eyelid area responsible fir eyelid closure.

Orbicularis ori—skeletal muscle of the mouth area responsible for closure and competency of the lips and mouth.

Parasymapathetic—refers to one division of the autonomic nervous system.

Platysma myoides—skeletal muscle of the neck that protects deeper structures of the neck.

Platysma—same as above.

Procerus muscles—skeletal muscle of the central forehead responsible for frowning and producing horizontal creasing along the nasofrontal area.

Procerus—same as above.

Rhinorrhea—excessive nasal mucous secretions.

Supercilli—a portion of the corrugator muscle that sits above the eyelids.

Temporalis—skeletal muscle of the jaw that stabilized the temporamandibular joint.

Zygomaticus major—skeletal muscle of the face that produces smiling or creasing of the midface.

Electrical Terms.

ADC: Analog to digital converter.

ASCII: American standard of computer information interchange.

BAUD: Serial communication data rate in bits per second.

BYTE: Digital data 8-bits in length.

CHARACTER: Symbol from the ASCII set.

CHECKSUM: Numerical sum of the data in a list.

CPU: Central processing unit.

EEPROM: Electronically erasable programmable read only memory.

FLASH MEMORY: Electrically alterable read only memory. (See EEPROM)

UI: Graphical user interface.

HEXADECIMAL: Base 16 representation of integer numbers.

I2C BUS: Inter Integrated Circuit bus. Simple two-wire bidirectional serial bus developed by Philips for an independent communications path between embedded ICs on printed circuit boards and subsystems.

The I2C bus is used on and between system boards for internal system management and diagnostic functions.

INTERRUPT: Signal the computer to perform another task.

PC: Personal computer.

PWM: Pulse-width modulation.

ROM: Read only memory.

WORD: Digital data 16-bits in length

BRIEF DESCRIPTION OF THE DRAWINGS

Figure 1:
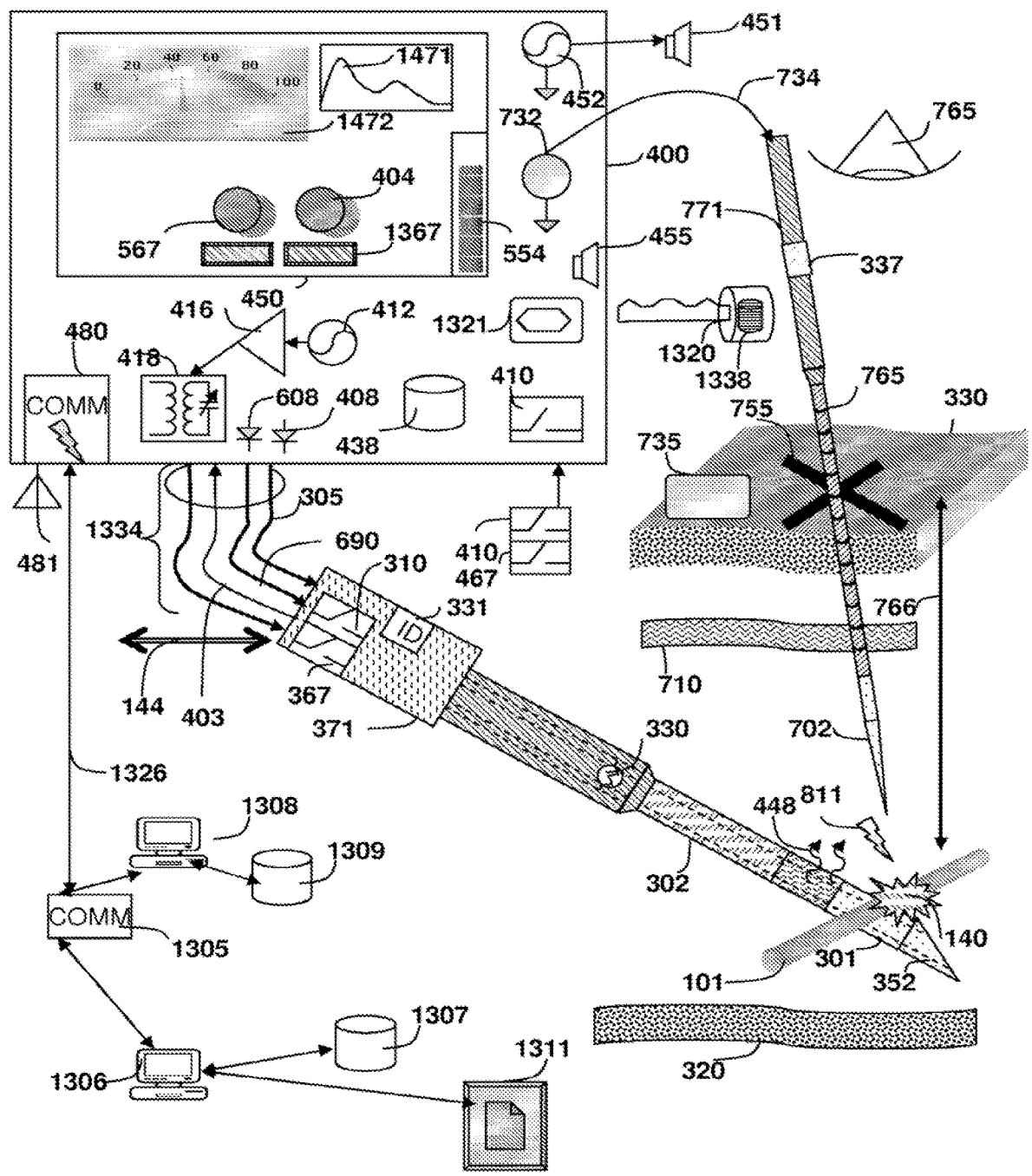
FIG. 1 Bi-Polar Driver System.

FIG. 1 illustrates two main components and one optional component, which are the energy generator 400, the probe 371 (alternate probes are described in FIGS. 3A-D) and optionally probes 771 or 772 that may be used.

In normal operation, the novel probe 371 would combine a unique bipolar configuration in a single MIS needle, is inserted into the patient using MIS techniques. The probe, which may contain and/or convey various functions described later, is initially guided anatomically to the region of the anticipated or desired location. Various means of locating the tip 301 are utilized of placing the zone of ablation in the proper area to interrupt signal flows through the nerve 101.

Device Operation

Many combinations of electrode diameters and tip shapes are possible. The 'novel' probe performs a variety of functions, such as stimulation, optical and electronic guidance, medication delivery, sample extraction, and controlled ablation. This bi-polar electrode is designed as a small diameter needle inserted from a single point of entry thus minimizing scaring and simplifying precise electrode placement. This low cost, compact design provides a new tool to the art.

Figure 8:
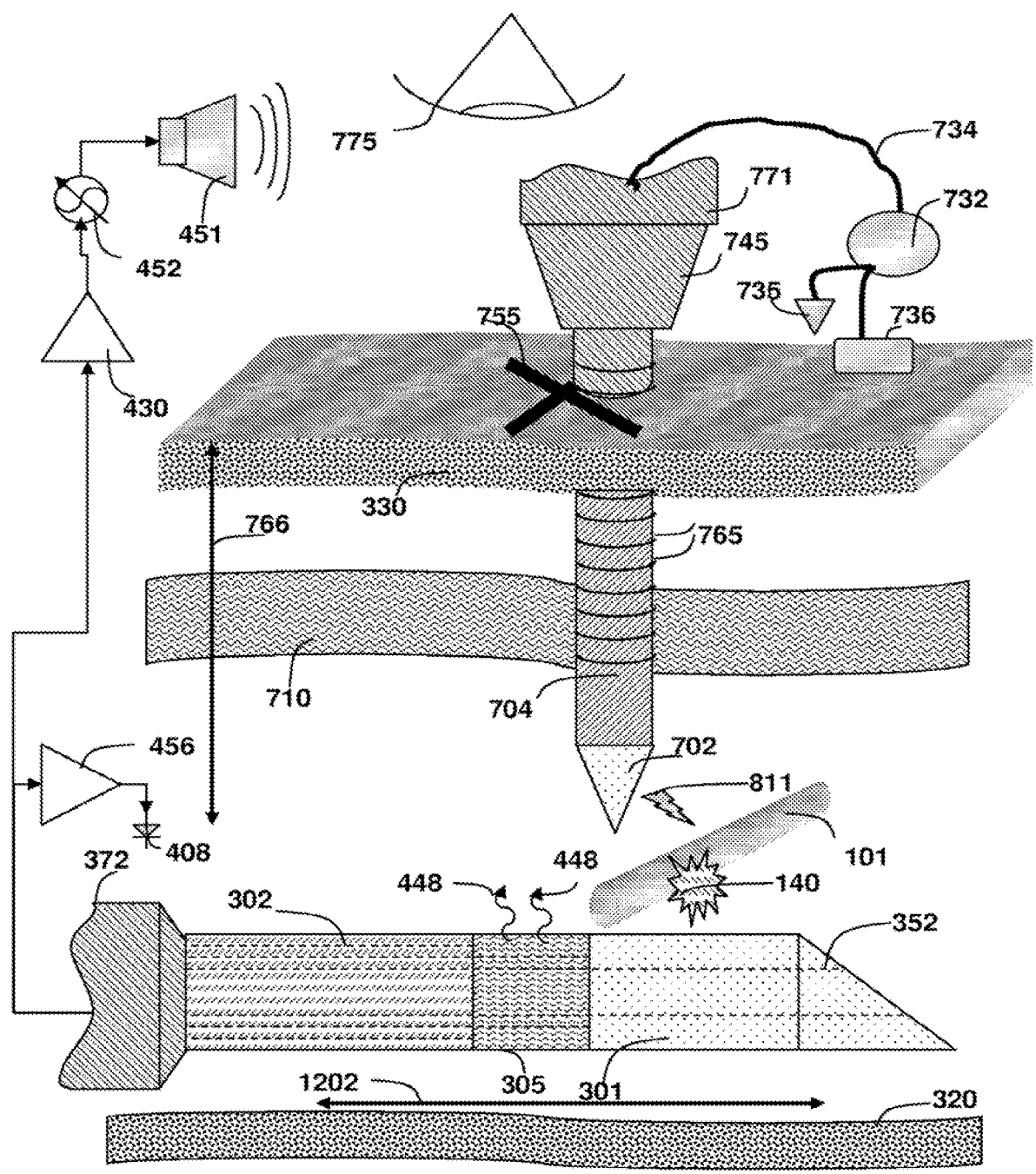
FIG. 8 Side view of guided ablation procedure with auxiliary nerve probe(s).

Probes may emit fiber optic illumination for deep applications using electronic guidance as taught in FIGS. 1 and 8. The invention offers a simple low cost ablation probe that is capable of performing precise ablation while minimizing damage to nearby tissue structures. The metered ablation energy and precise probe targeting give the practitioner a tool is also not available in prior art. The practitioner has unprecedented control of treatment permanence in a minimally invasive procedure. Such a procedure is typically performed in less than one hour with only local anesthetic and would require no stitches or chemicals common to prior medical art.

Stimulation/Ablation

Figure 4:
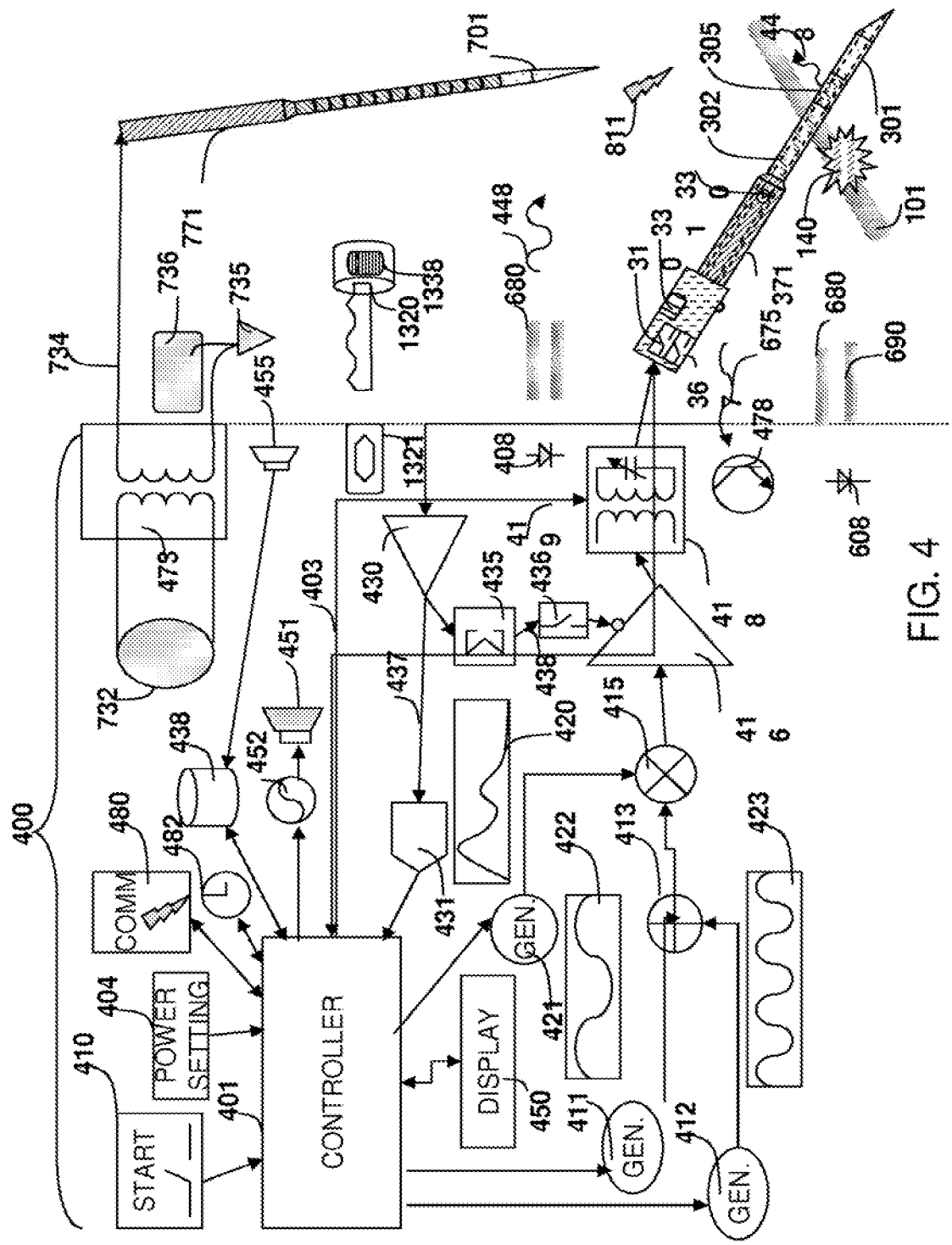
FIG. 4 Schematic diagram of the bi-polar driver system.

First the probe electrode 301 must be in the desired location relative to the target nerve 101 (FIG. 4), then the user initiates the treatment via switch(s) 410 and 310 using the selected power setting 404 (FIG. 4). The controller configures the generators 411 (FIG. 4) and 412 to the amplitude frequency and modulation envelope, delivering 50 K Hz-2.5 MHz of 5 to 500 watts of available energy. The summing junction 413 combines the RF outputs as the application requires and passes them to the pulse-width modulator 415 for output power control. The output of modulation generator 420 is applied to the multiplier 415 with radio frequency RF signals 422 and 423. This permits complex energy profiles to be delivered to a time variant non-linear biologic load. All of these settings are based on the information provide to the generator by the installed probe 371 the selected power 404 settings, and the modulation envelope 420 (FIG. 4) settings, which are then loaded b the generator 421.

For example, both a high amplitude sine wave 910 (FIG. 9), used for cutting, and a pulse-width modulated (or PWM) sine wave 920, used for coagulation, are well known to electro-surgery art Precise power rates and limits of average total power are controlled via integrator 435 minimizing damage to nearby structures or burning close to the skin for shallow procedures. Where nearby structures 111 are too close to be avoided by electrodes such as 371 (FIG. 3), 372 (FIG. 3A), and 372 (FIG. 3B), additional probe geometries as taught in FIGS. 3D, 6, 6A, and 6B offer novel methods to direct energy and limit ablation to a smaller region, thereby avoiding other structures. For safety a hardwired switch 436 disables the power amplifier in the event of a system limit, the probe is unplugged or over power condition, thus protecting both the patient and practitioner.

The output of the modulator 415 is applied to the input of the power amplifier 416 section. The power amplifier's 416 outputs are then feed into the impedance matching network 418, which provides dynamic controlled output to the biologic loads that are highly variable and non-linear, and require dynamic control of both power levels and impedance matching. The tuning of the matching network 418 is performed for optimal power transfer for the probe, power level, and treatment frequencies settled. The system's peak power is 500 watts for this disclosed embodiment. Precise control is established by the proximity of the tip and the control loops included in the generator itself. The final energy envelope 420 is delivered to probe tip 301 and return electrodes 302.

This precise control of energy permits extension of the ablation region(s), 140 and 1203 (FIG. 10), and the duration of treatment efficiency. Low or medium energy settings 404 permit temporary nerve-conduction interruption for 3-6 months. Higher energy settings at 404 may result in a longer nerve conduction interruption of 1 year to permanent. In the prior art, procedures had little control over duration of termination of such signal flow through the nerve. This invention gives the practitioner enhanced control of such duration. Patients can evaluate controlled temporary treatment before choosing longer or permanent treatment options.

A low energy nerve stimulator 771 has been integrated into the system to assist in more precise identification of nearby structures and for highly accurate target location. Lastly, additional sensors, such as temperature 311, voltage, frequency, current and the like are read directly from the device and/or across the communications media 403 to the probe.

Directed Ablation

In addition to the substantial radially-symmetric ablation patterns with probes as taught in 371 (FIG. 3) and 372, switching or dividing ablation power to multiple electrodes (FIG. 3D) can generate an asymmetric ablation zone. This high intensity source 608 with probe 610 (FIGS. 6 and 6A) minimizes damage to nearby structures 111 or the burning of skin 330 in shallow procedures. Also, FIG. 3D identify probe configurations for selective or asymmetric ablation.

Power Feedback

The power amplifier output 430 and buffered the feedback signals 437 are connected to an Analog to Digital converter (or ADC) 431 for processor analysis and control. Said signals 437 control power modulation 420 settings and impact the impedance matching control signals 419. This integrated power signal 437 is recorded to the operating-condition database (FIG. 11) for later procedure review. This power level is also compared to reading taken from the probe 1492 (FIG. 11A) as compared against procedure maximums, which if exceeded will in turn disable the amplifier output, thereby protecting the patient from error or equipment fault. Similarly, limits from the probe and generator sensors such as temperature 330 are also used to terminate or substantially reduce the modulated power levels and ultimately the procedure.

Probe Identification

At power startup, the controller 401 (FIG. 4) reads the probe status and internal identification kept within the probe itself 331 (and 371) via serial communications 403 (or bus). Serial communications is used because it is commonly available to most single-chip microprocessors. This or similar methods (e.g. I2C, or SPI) may be used, but this disclosed embodiment will use serial for its simplicity. Serial communications 403 permits the generator to address and control EEROM memory 331, temperature sensors 330, processors, ADC and DACs within the single-chip microprocessor embedded in the probe itself The user selects the desired power setting 404 and based on probe identification read from the EEROM or microprocessor 331 makes the appropriate configurations. The probe 371 is connected via cable 1334 (FIG. 1) to control unit 101 or generator. This probe is not intended for multiple procedural uses. So to prevent such use of the probe, the controller 401 (FIG. 4) reads the stored time register from ID memory module 331. If the probe's initialized time 1467 (FIG. 14) is zero, the current real-time clock 482 value is written to probe's 331's initial time register via serial bus 403. If time read on module 331 is non-zero, the probe's initial time register is added to two (2) times the procedural time (based on the probe type) FIG. 14 1420. If that value when compared to current real-time clock 482, is less than current time, the controller will alert the practitioner via display 450, speaker 451 and flashing probe illumination 608, that the procedure will be terminated and the probe rendered invalid.

The controller 401 also verifies selected procedure 1415 (FIG. 1) for compatibility with installed probe. If incompatible, the user is also prompted to select a different power setting 404, procedure, or probe 371. If probe 371 matches power setting 404, the system enables power amplifier 416, guide light source 408, and low-voltage nerve simulation 732. Both of these procedures are enforced by a mandatory "hand shake" protocol and the serialized information, which must be present and properly verified by the electronic circuitry for a procedure to be instituted. During a clinical procedure, information is required to be conveyed by the embedded electronics contained within the probe, which provides another way of enforcing this protection and thus again preventing unauthorized re-use. The ultimate goal is prevent cross-contamination between patients. The probe will accomplish this by being unique, serialized, and given the above procedures. Once plugged in, the probe will enter the serial number into the data logging system via the serial bus 403 and circuit logic will thereafter prevent re-use of the probe and cross-contamination that would occur. Further, this scheme will prevent the use of unauthorized third party probes, for they will not be activated, preventing potential inferior or uncertified probes from being used and presenting potential danger to the patient.

Nerve Target Location Tools

Prior to treatment, the practitioner may use auxiliary probe 771 (FIG. 4), to locate target 101 and nearby structures 111 as taught in FIGS. 4, 7, 7A, 8, and 10. When needle 771 is in place, the practitioner may locate and place a mark or marks on the surface of the skin 755 (see FIGS. 7 and 8) or leaves auxiliary probe 771 in place. For shallow subcutaneous procedures, probe tip illumination 448 from source 408 is visible to practitioner aiding, in probe placement to pre-marked location.

Location Via Florescence Marker Dye.

Figure 6:
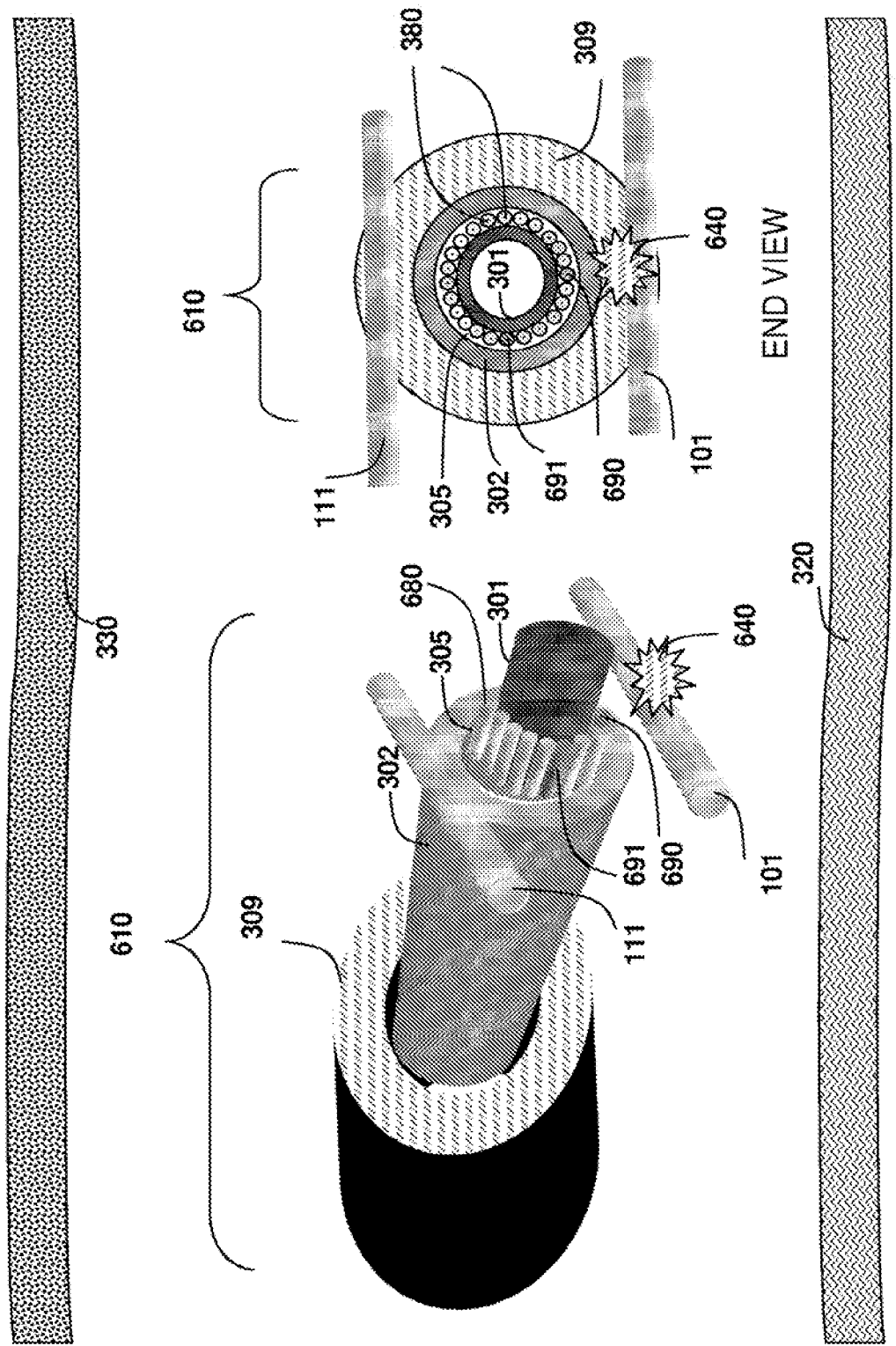
FIG. 6. Side view Hybrid bi-polar needle for nerve ablation.
Figure 6A:
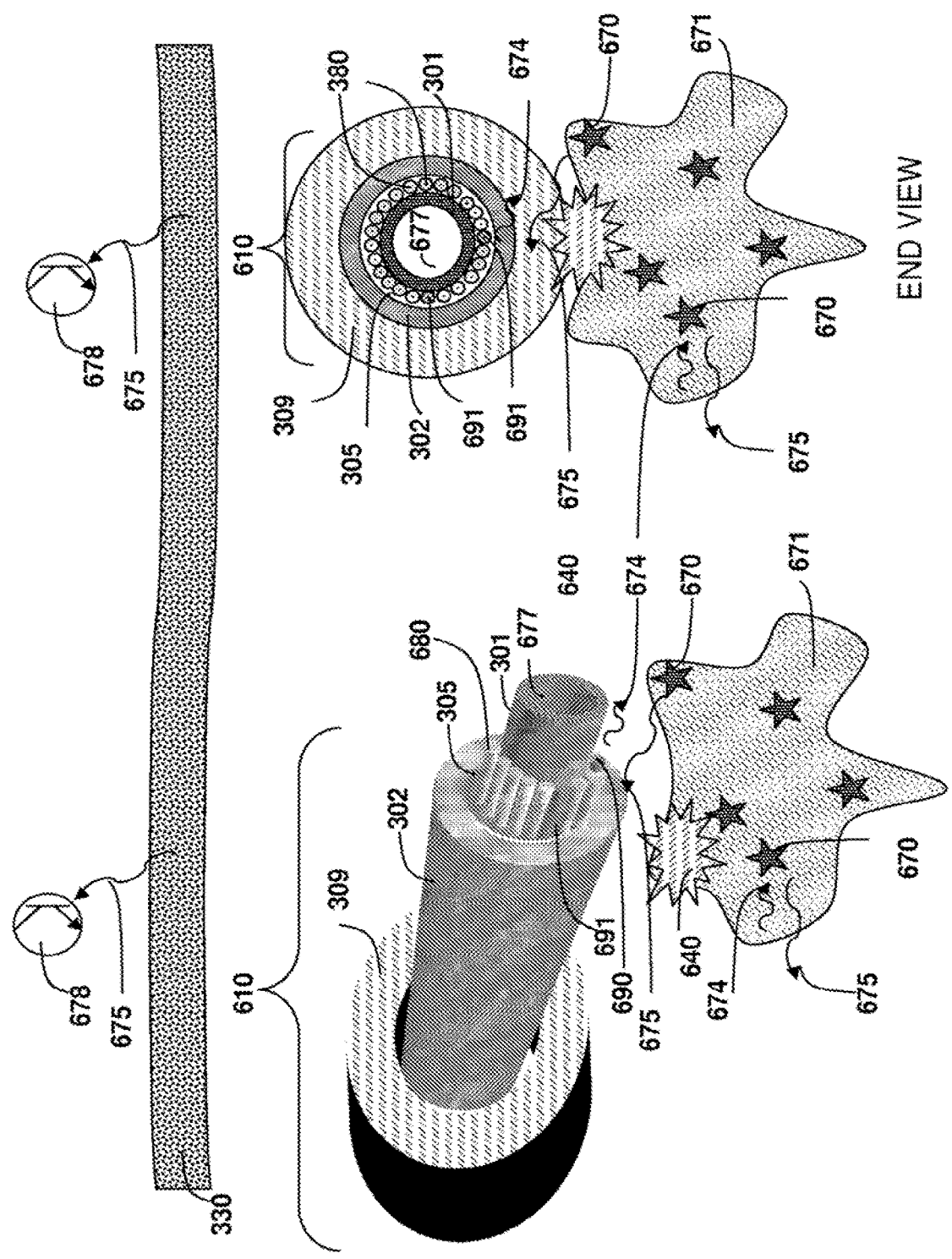
FIGS. 6A and 6B illustrate examples of directing energy and limiting ablation to smaller regions and thereby avoiding other structures.
Figure 6B:
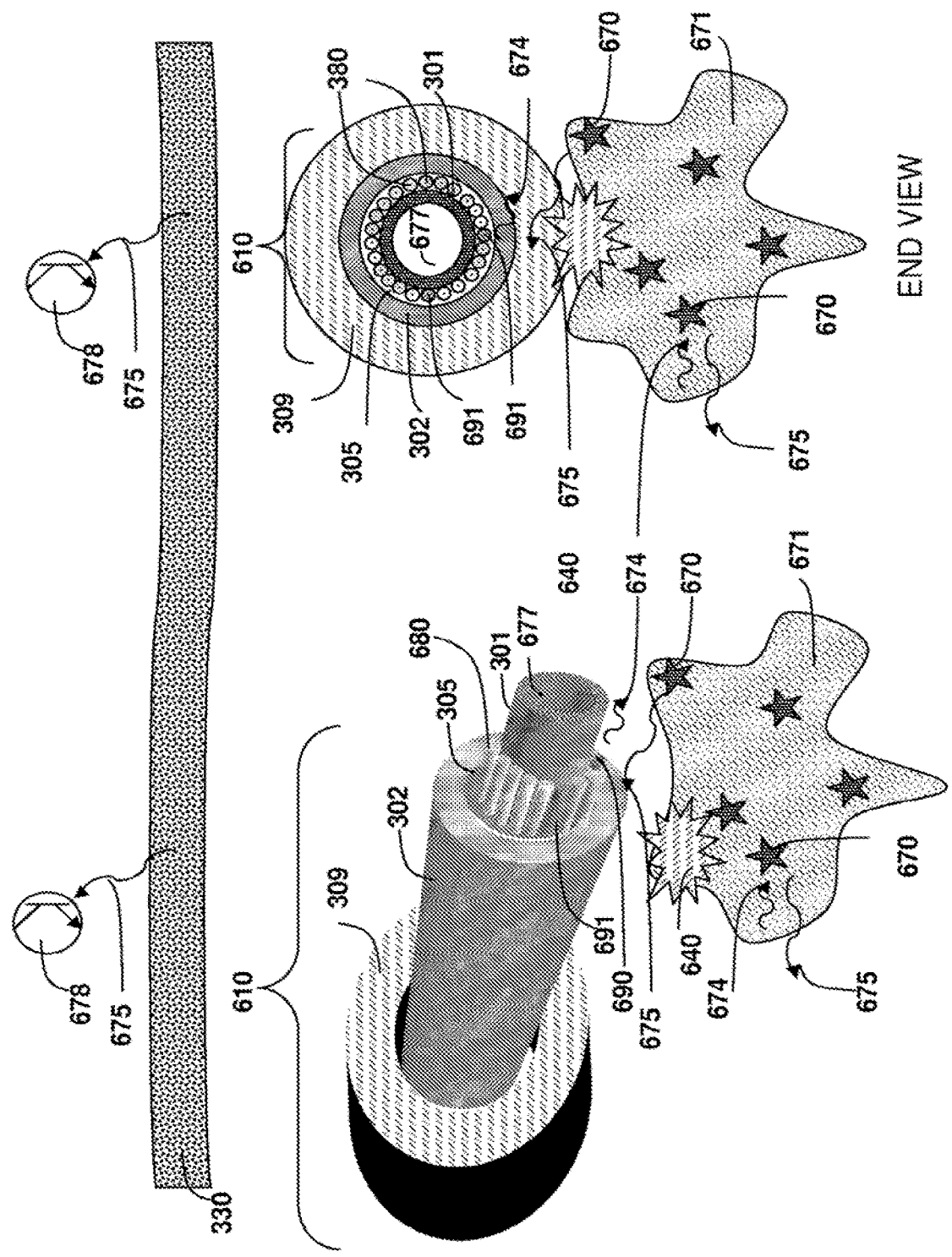

In other procedures, whereby somewhat larger targets are sought, such as more diffuse nerve structures or small areas of abnormal growth (e.g. such as cancer) the injection of specially designed dyes that attach to target structures are used, as taught in FIG. 6A. The probe 610 (FIG. 6) is moved into the proximity of the target 671. The light source 6087 illuminates quantum-dot/dye tagged antibody 670. The dye fluoresces 675 at a frequency/wavelength of a particular material and will typically emit light in the visible to infrared (or IR) or potentially other wavelength regions. The return fiber(s) 680 deliver emissions 675 to the detector 478 for measurement and are the result is then displayed on bar graph 554 (FIG. 1) and/or an audio tone sounded via speaker 451 based on proximity. Visible and IR light emissions propagate over limited distances permitting additional external detectors 678 to be used for shallow targets just under the skin 330. Location via this method is similar to the electronically guided probe method taught in FIG. 8 where probe 640 movement maximizes the signal output when in close proximity. IR emissions propagate and can permit deeper (typically several centimeters) detection with optional additional external sensors 678. Unfortunately, many dyes fluoresce in the visible region making external detection imposable for deep targets or when obscured by bone. However, probe 610 (FIG. 6A) solves this problem by integrating; target illumination 674, emission 675 detector, ablation, biopsy, and medication delivery in single compact probe. Electronic probe guidance (FIG. 8) if required is used in combination with florescence detection to rapidly locate target. The instant invention offers a minimally invasive system for locating and treating small/deep tumors and other tissue that are to be ablated, destroyed or removed.

Electronic Probe Guidance

Low energy nerve stimulation current 810 (FIG. 8) assist in locating, desired treatment region and avoiding nearby structures. Probe 771 is selectable between nerve stimulator and current measurement to/from auxiliary probe tip 702 (FIG. 8). Return electrode 736 provides a return path for local ground 735. Ablation probe switch 367 selects low-energy stimulator/receiver and high-energy ablation to/from probe 372. Amplitude of measured guidance current 811 and light 478 are transmitted to display 554, and audio feedback 452 through the speaker 451.

Optical Probe Guidance

Disclosed invention provides optical sources 408 that aid in probe placement (FIG. 10) by supplementing stimulation source 732 and acting as preliminary guide. Probe 771 is selectable between nerve stimulator or current 811 measurement and to or from the auxiliary probe tip 702. The ablation probe switch 367 selects low-energy stimulator/receiver or high-energy ablation to or from probe 371, 372, 373, and 374. In this mode, the physician operator will have previously placed marks 755 on the surface of the skin by various means described. The physician operator 775 will then see the tip when the 448 if the optical illumination is turned on. It 448 will provide a bright spot wider the skin indicating the location of the tip in relation to the marks 755. The physician 775 will then guide the probe tip 301 into precise alignment under these marks 755 so as to enable ablation of that target tissue 101.

Data and Voice

Real-time engineering parameters are measured such as average power 437, luminous intensity 478, probe current 811, energy 438 and, temperature 330 to be recoded into USB memory 438. Simultaneously, the internal parameters disclosed such as frequency 423, modulation 420 and such are recoded into SIB memory 438 as well. Additionally probe, patient, and procedure parameters (FIG. 11) are written to local storage 438. The practitioner dictates text and voice notes via microphone 455, which are saved to memory 438 (FIG. 1). All data and records are time stamped using the real-time clock 482. This permits detailed post procedure graphing and analysis.

Data Transfer

At procedure conclusion, the system transfers the data 438 recorded to the USB removable memory 1338 and to a file server(s) 1309 and 1307. In the disclosed embodiment, data transfer is performed over Ethernet connection 480. Probe usage records 1460 (FIG. 11) that are stored in local memory 438 are then written to removable memory module 1338. Parallel records are mirrored to local storage 1309 and remote server 1306 storage 1307 via Ethernet connection 480 or similar means. Sensitive records are encrypted and transferred via secure network connection and also written to removable module 1320. The database contained on the remote server tracks the following information: equipment by manufacture, probe accessory inventory, usage, billing, repair/warranty exchange information, and program records. As a system 400 is certified for new procedures 1410 (FIG. 11), the relational databases are automatically updated to reflect new billing/procedure codes 1416, potential power settings 1417 and the like. This insures that the equipment is current and alerts the practitioner to new probes/procedures as they are developed and certified.

Before further explaining the disclosed embodiment of the present invention in detail, it is to be understood that the invention is not limited in its application or to the details of the particular arrangement shown. The invention is capable of other embodiments. Further, the terminology used herein is for the purpose of describing the probe and its operation. Each apparatus embodiment described herein has numerous equivalents.

FIG. 1 Bi-Polar Driver System

Figure 2:
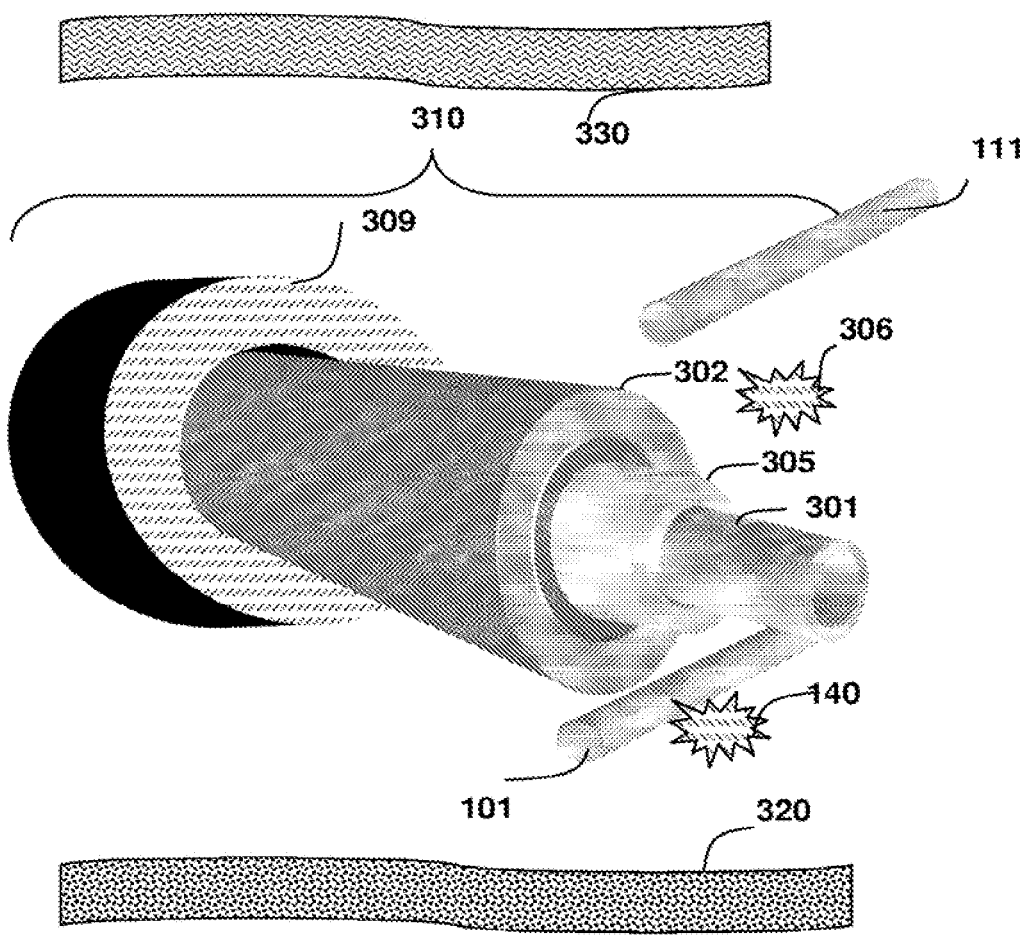
FIGS. 2, 2A and 2B are schematic diagrams.
Figure 2A:
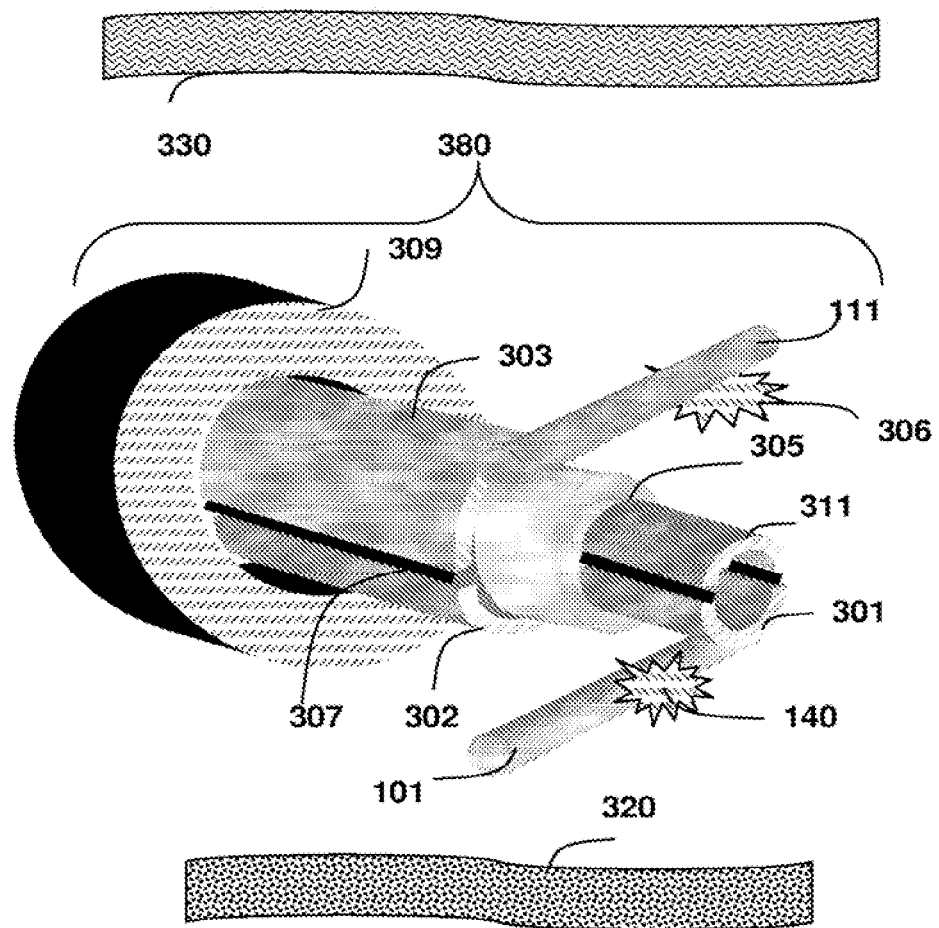
Figure 2B:
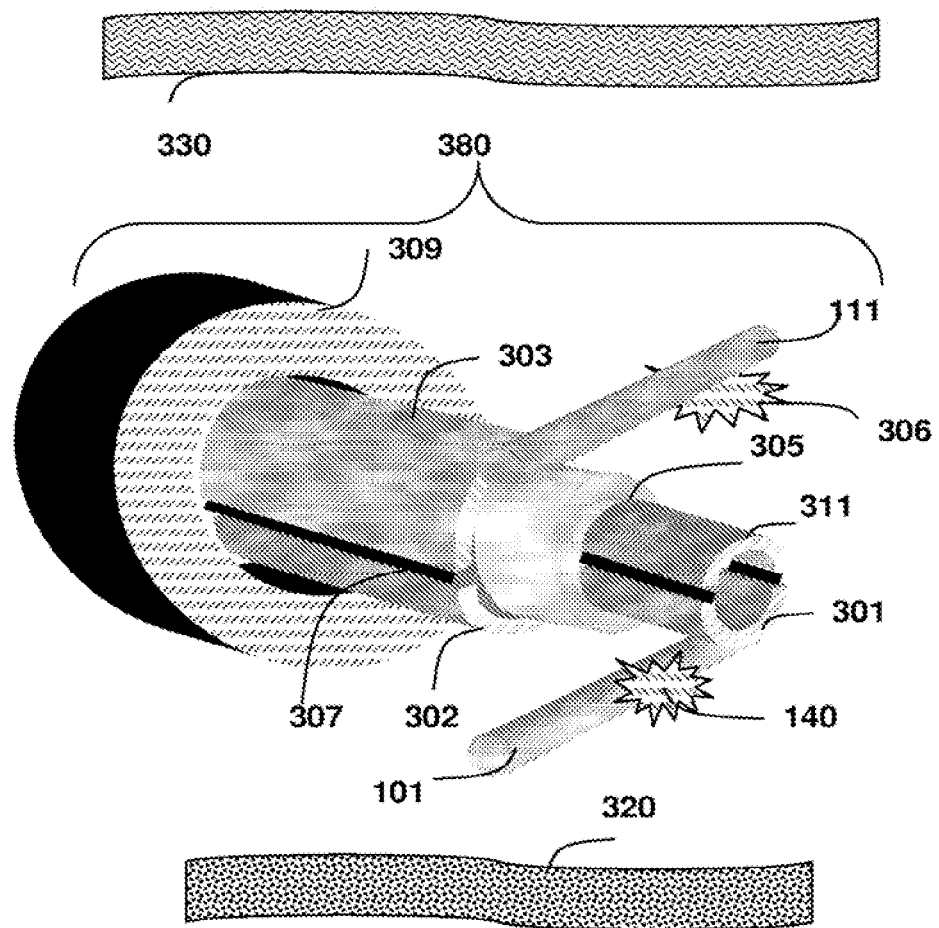

FIG. 1 identifies the two required components of the system, various modules and optional items. The two components always utilized during a procedure will be the energy generator/controller/data storage device 400 and probe 371. 400 contains advanced electronic systems capable of recognizing a properly authorized probe, preventing re use of a previously used probe, generating appropriate energy as described, performing safety checks, storing data, and other functions as described. Main functions of 400 may include, but not be limited to, generation of light, generation of location-stimulation currents, generation of ablation energies, data logging, storage, communication and retrieval, and other functions critical to a MIS procedure. Probe 371 and its various forms are single puncture bipolar surgical tools that may be used in identifying proper location of its tip 301, in relation to target tissue 101 which is desired to be ablated, modified or destroyed. Probe 771 and its various derivatives may optionally be used to assist in locating and properly positioning tip 301 of probe 371, FIG. 2 Isometric View of the Bi-Polar Probe Bi-polar probe 310 represents probes 371, 372, 373 shown in FIGS. 3A-C with exception to type of needlepoint on the probe. FIG. 3D varies from the other because it has a split return probe. Bi-polar probe 310 (not drawn to scale) consists of insulating dielectric body 309 made from a suitable biology inert material, such as Teflon, PTFE or other insulative material, covering electrode 302 except for where 302 is exposed as a return electrode. Conductive return electrode 302 tube is fabricated from medical grade stainless steel, titanium or other conductive material. Hollow or solid conductive tip electrode 301 protrudes from surrounding dielectric insulator 305. Sizes of 309, 302, 305, and 301 and its inner lumen (diameter, length, thickness, etc.) be adjusted so as to allow for different surface areas resulting in specific current densities as required for specific therapeutic applications.

Hollow Electrode 301 often used as a syringe to deliver medication such as local anesthetic. Tip electrode 301 is connected to power amplifier 416 via impedance matching network 418 (FIG. 4). Return electrode(s) 302 delivers return current to power amplifier 416 via impedance matching network 418. Dielectric insulator in the disclosed embodiment is a transparent medical grade polycarbonate acting as a light pipe or fiber optic cable. Light source LED or laser 408 (FIG. 4) provides illumination at the far end of the probe via fiber optic cable/transparent dielectric 305 for guiding the probe under the skin i.e. shallow procedures. In an alternate embodiment dielectric, insulator is replaced with a plurality of optical fibers for viewing and illumination as taught in FIG. 6.

Ablation regions 306 and 140 extend radially about electrode 301 generally following electric field lines. For procedures very close to skin 330 a chance of burning exists in region 306. To minimize the chance of burning, a split return electrode probe 374 in FIG. 3D is offered. Thereby concentrating, the current away from region 306 to 140 or vice versa.

Figure 3A:
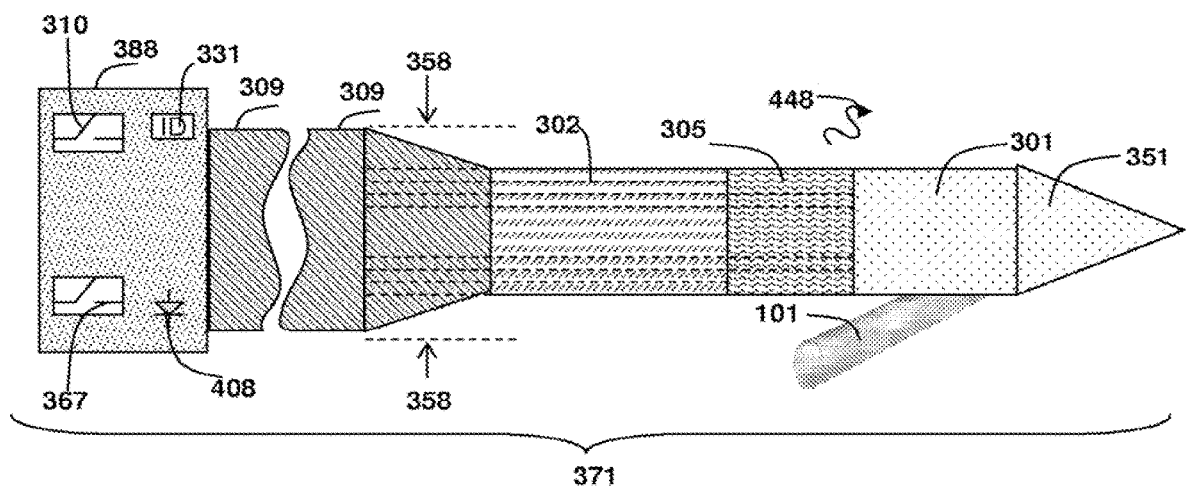
FIG. 3A Magnified side view of conical bi-polar probe.

FIG. 3A Conical Bi-Polar Needle

Bi-polar probe 371 discloses conical shaped electrode 301 and tip 351 for minimally invasive single point entry. Probe diameter 358 is similar to a 20-gage or other small gauge syringe needle, but may be larger or smaller depending on the application, surface area required and depth of penetration necessary. In disclosed embodiment, electrode shaft 302 is 30 mm long with approximately 5 mm not insulated. Lengths and surface areas of both may be modified to meet various applications such as in cosmetic surgery or in elimination of back pain. The conductive return electrode 302 is fabricated from medical grade stainless steel, titanium or other conductive material. The dielectric insulator 305 in the disclosed embodiment is a transparent medical grade material such as polycarbonate, which may double as a light pipe or fiber optic cable. The high intensity light source 408 LED/laser (FIG. 4) provides guidance Illumination 448 at working end of probe. The illumination source modulation/flash rate is proportional to the received stimulation current 810 as taught in FIG. 8. A small diameter electrode permits a minimally invasive procedure that is typically performed with local anesthetic. This configuration may contain lumens for delivery of agents as described elsewhere.

Figure 3B:
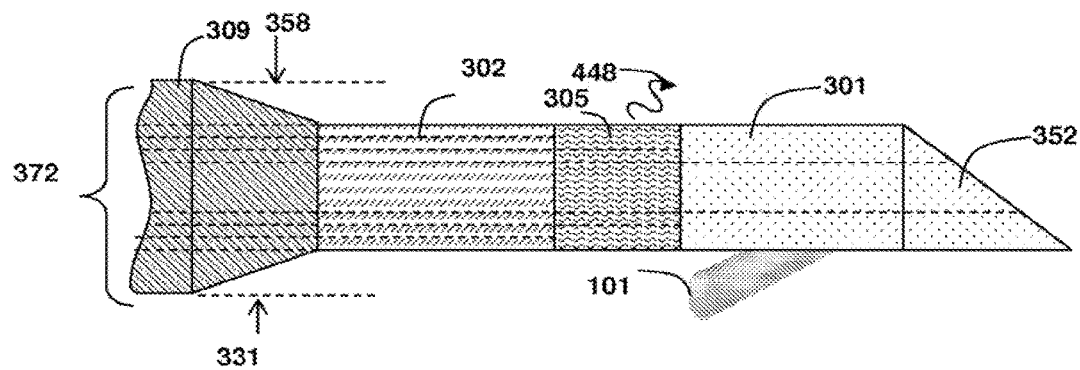
FIG. 3B Magnified side view of hollow chisel bi-polar probe.

FIG. 3B Hollow Chisel.

The hollow chisel electrode 352 is often used as a syringe to deliver medication such as local anesthetic, medications/tracer dye. The hollow electrode may also extract a sample. Dielectric insulator 305 in the disclosed embodiment is a transparent medical grade polycarbonate and performs as a light pipe or fiber optic cable. The novel dual-purpose dielectric reduces probe diameter and manufacturing costs. Light source 408, typically a LED or laser (FIG. 4 not shown), provides Illumination 448 at the working end of probe. It provides an illumination source for guiding the probe under the skin. A second embodiment, as taught in FIG. 6, dielectric insulator is replaced/combined with plurality of optical fibers for viewing/illumination.

Figure 3C:
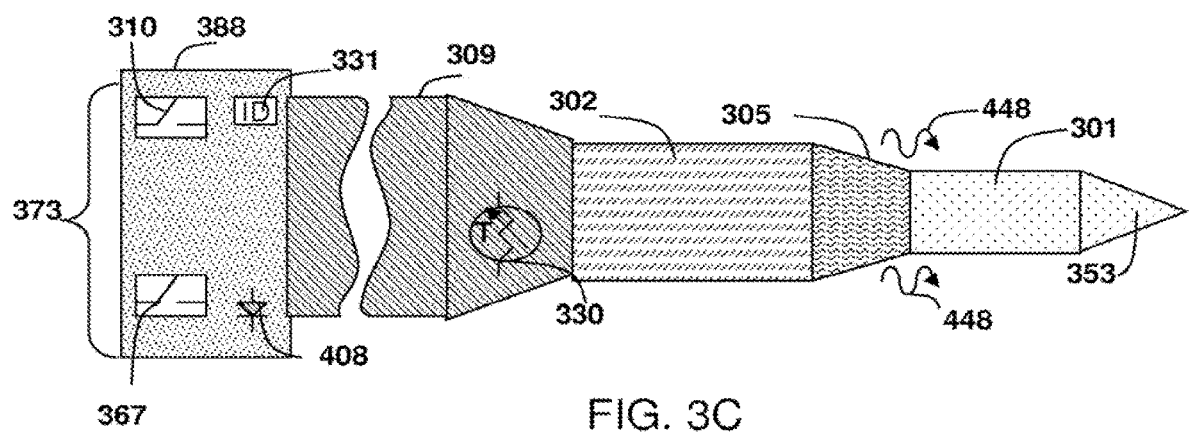
FIG. 3C Magnified side view of tapered conical bi-polar probe.
Figure 3D:
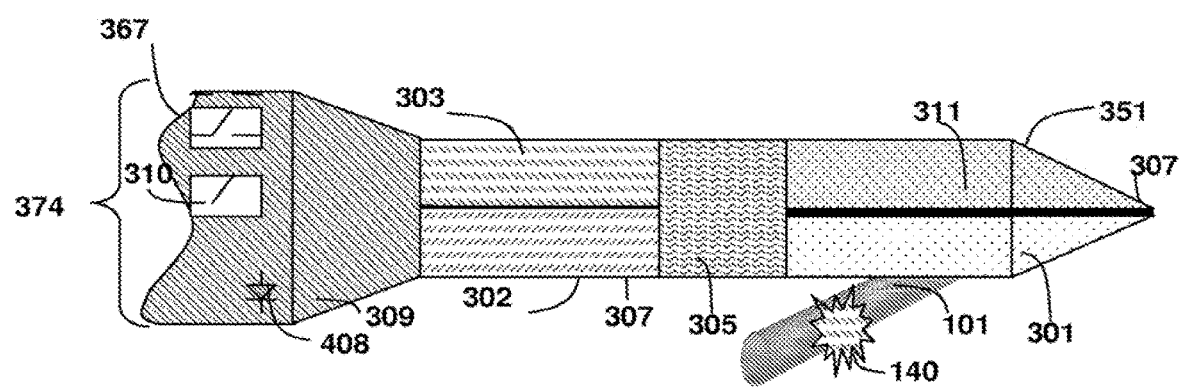
FIG. 3D Magnified side view of split conical bi-polar probe.

FIG. 3C Tapered Conical

Figure 13:
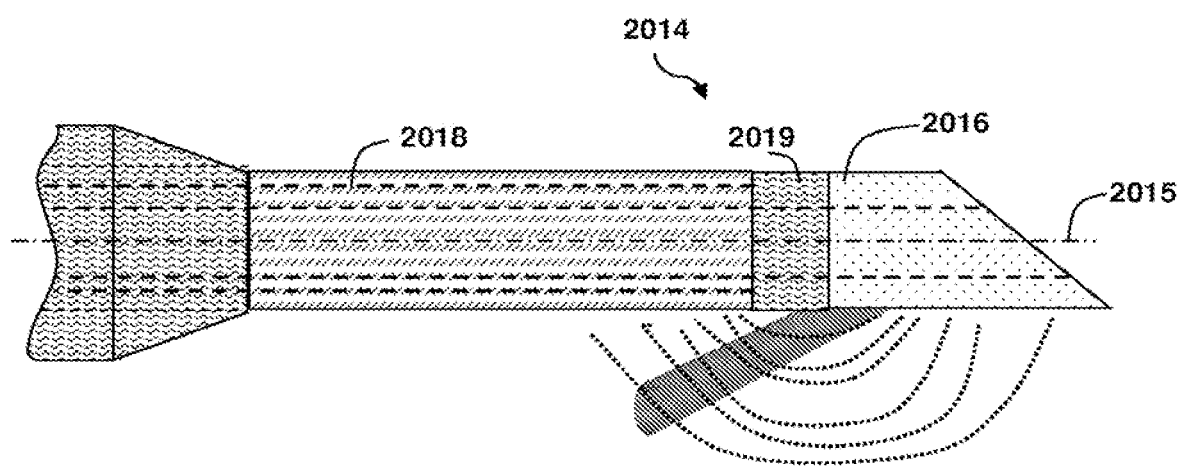
FIG. 13 is a side view of a single axis electrosurgical probe having two electrodes of differing surface areas.

The bi-polar probe 373 discloses a tapered conical shaped probe for minimally invasive single point entry. It is constructed similarly to probe 371 as taught in FIG. 3A. Probe tip is not drawn to scale to teach the tip geometry. In disclosed embodiment, electrode 301 is approximately 5 mm long and fabricated from medical grade stainless steel but may be of various lengths to accommodate specific application and surface area requirements. The solid tapered conductive tip electrode 353 protrudes from tapered dielectric insulator 305. Transparent dielectric insulator 305 also performs as light pipe or fiber optic cable terminated to high intensity light source 408 (FIG. 4) providing illumination 448. The electrode assembly is mounted in an ergonomic handle 388 (which has not been drawn to scale). Handle 388 holds ablation on/off switch 310, ablation/stimulation mode switch 367, identification module 331 and terminations for cable 1334 (FIG. 13). Temperature sensor 330 (located close to tip) monitors tissue temperature.

FIG. 3D Split Conical Bi-Polar Probe

Description of this probe is described in both drawings 2A and 3D. Bi-polar probe 374 (not drawn to scale) consists of insulating dielectric body 309 made from a suitable biologically inert material, such as Teflon, that covers split return electrodes 302 and 303. Conductive return electrodes 302 are fabricated from medical grade stainless steel, titanium or other suitable conductive material. Hollow or solid split conductive tip electrodes 301 and 311 protrude from surrounding dielectric insulator 305. Their operation is very similar to probe tip 380. Solid tapered conductive tip electrodes 311 and 301 protrude from transparent dielectric insulator 305. Dielectric insulator 305 also performs as a light pipe or fiber optic cable terminated to high intensity light source 408 providing illumination 448.

Probe handle (not drawn to scale) encloses memory module 331, on/off switch 310 and mode switch 367. Temperature sensor 330 (located close to tip) monitors tissue temperature. Split electrode 380 permits dividing or splitting energy delivered to electrode pairs 301/302 and 311/303. Dual amplifiers or time multiplexing/switching main amplifier 416 are located between electrode pairs directing energy to target 101 avoiding 111 creating asymmetric ablation volume. A small diameter electrode needle is injected from a single point of entry minimizing scaring and simplifying precise electrode placement.

Connections consist of a tapered dielectric sleeve 309 covering the ridged stainless electrode tube 302 Insulating sleeve 309 is made from a suitable biologically inert, material, which covers electrode 302. Dielectric 305 insulates conical tipped electrodes 351 and 301.

Figure 5A:
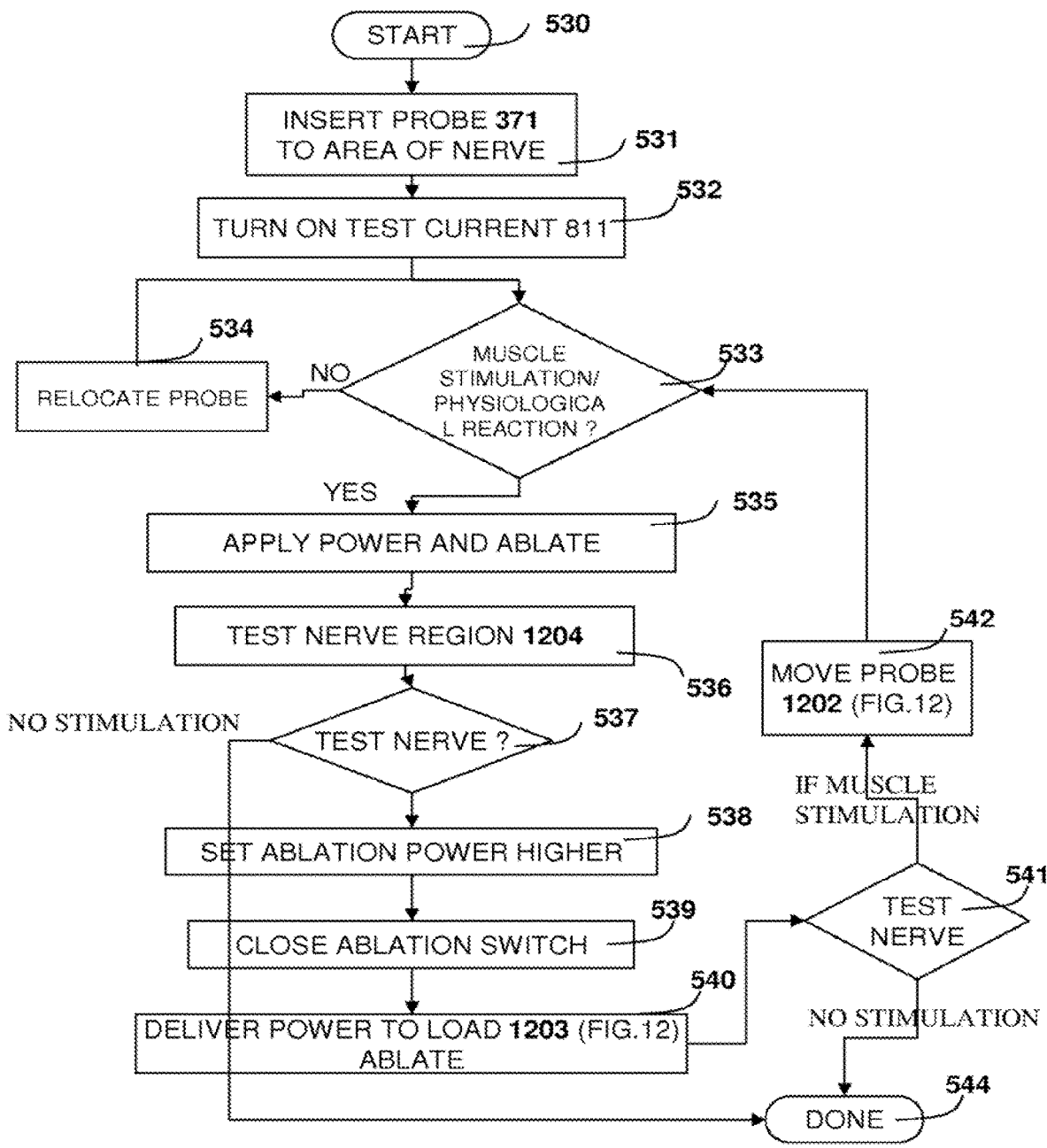
FIG. 5A Ablation Procedure without Auxiliary probe.

FIG. 5A Ablation Procedure (Without Auxiliary Probes)

Ablation probe 371 is inserted and directed anatomically into the area where the target nerve to be ablated (Box 531) is located. Test current 811 is applied (Box 532). If probe is located in the immediate proximity of the target nerve a physiological reaction will be detected/observed (Example: During elimination of glabellar furrowing, muscle stimulation of the forehead will be observed). If reaction is observed, then a mark may optionally be applied on the surface of the skin to locate the area of the nerve. Power is applied (Box 535) in an attempt to ablate the nerve. If physiological reaction is not observed, (Box 534) the probe will be relocated closer to the target nerve and the stimulation test will be repeated (Box 536 & 537). If no physiological reaction is observed, the procedure may be terminated (Box 544). Also, the probe may be moved in any direction, up, down, near, far, circular, in a pattern, etc. to create a larger area of ablation for a more permanent result.

In Box 537, if stimulation is observed again, then the ablation power may be set higher (Box 538), alternatively, as mentioned, the needle may be moved in various directions, or a larger dosage of energy may be reapplied, to form a larger area of ablation, for more effective or permanent termination of signal conduction through the nerve. After delivery of power (Box 540), stimulation energy may be applied again (Box 541). If there is no stimulation, the procedure is completed (Box 544). If there is still signal flow through the nerve (stimulation or physiological reaction) then the probe may be relocated (Box 542) and the procedure is started over again (Box 533).

Figure 5B:
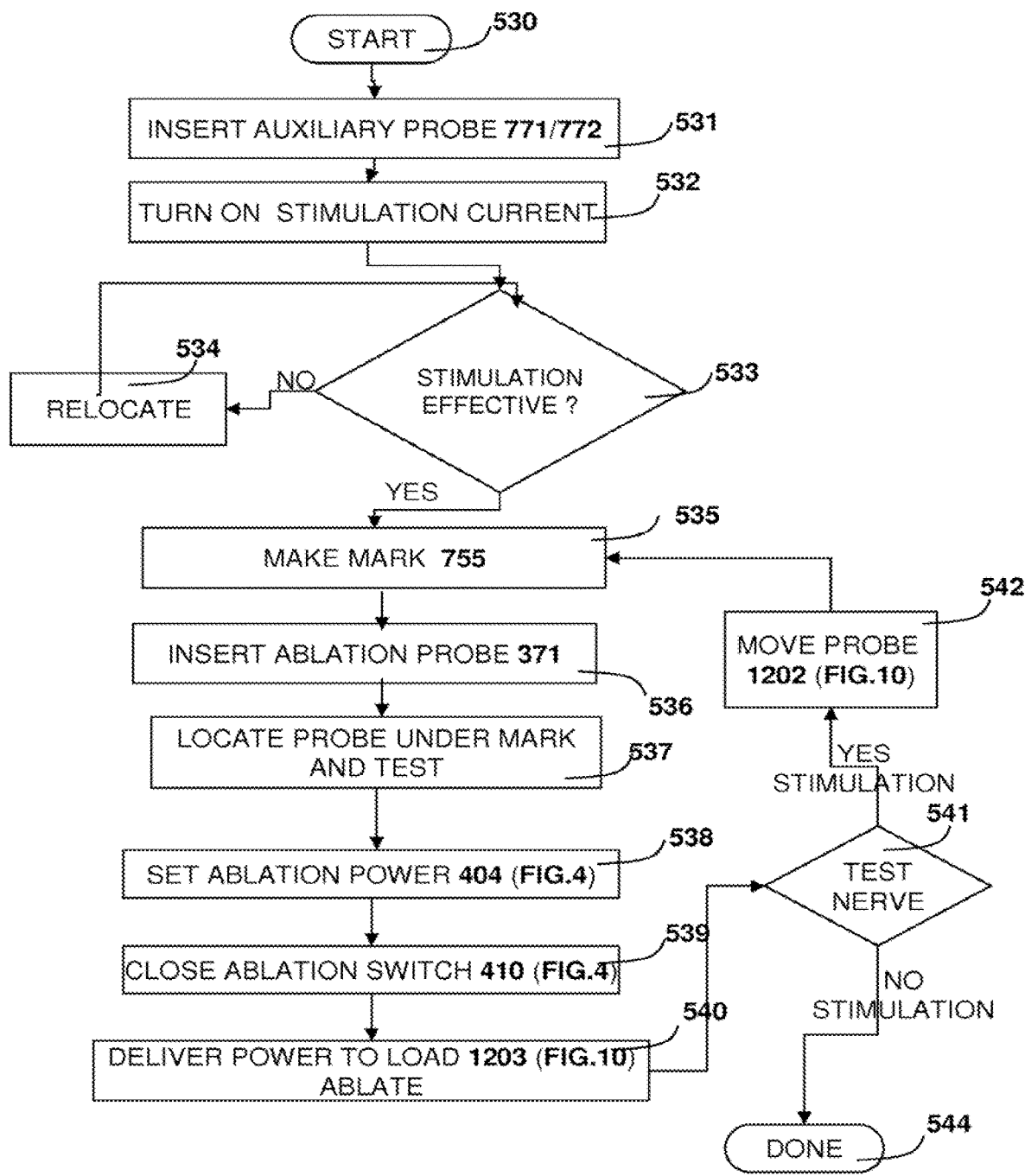
FIG. 5B Ablation Procedure with Auxiliary probe.

FIG. 5B Flow Chart of Visually Guided Ablation Procedure Using Auxiliary Probes Such As 771 and 772.

Auxiliary probes 771 and 772 (FIGS. 7, 7A and 7B) provide a method to quickly and accurately locate target structure 101 and subsequently mark target location 755. Auxiliary probes may be much smaller (like acupuncture needles) than ablation probes. Structures are marked typically with an ink or similar pen allowing the illuminated ablation probe 371 or other ablation probe to be quickly guided to mark 755. Optionally, non-illuminated probes may be used allowing the practitioner to simply feel for the probe tip. For deep structures, probe 771 (FIG. 8) us employed as an electronic beacon. Small current 811, which is similar to the stimulation current but smaller, from probe tip 702 is used to guide ablation probe 372 (FIG. 8).

Operation 530 (FIG. 5B) inserts auxiliary probe 771 or 772 (FIGS. 7 and 7A) thru skin 330 and muscle layer(s) 710 near nerve 101. Target 101 depth 766 is measured (FIGS. 7 and 7A) using auxiliary probe markings 765. Decision 533 checks if the probe is in position if not adjustments are performed in 534. Operation 532 enables nerve simulation current 811. When muscle stimulation is obtained or physiological reaction is obtained. Auxiliary probe tip is in place. Depth may be noted by reading marks 765 and location marks 755 may be made in operation 535. With the probe in position under mark in operations 536 and 537, operation 538 sets power level 404 and closes ablation switch 410. Alternatively, stimulation may be applied directly from the ablation probe as taught elsewhere. Operation 540 and controller 401 set generator 411 (FIG. 4) frequencies, modulation 420 envelope and enables power amplifier 416 to deliver preset ablation energy. Region 1203 (FIG. 10) shows the general shape of the ablation region for conical tip 301 for example.

Between each ablation, procedure 540 (FIG. 5A or FIG. 5B) (nerve conduction) is tested in 541. Probe amplifier 416 delivers small nerve stimulation current 811 from electrode 301 or Auxiliary probe 771 or both. Based on the nerve conduction test 541 if the desired level of conduction is achieved the procedure is compete. Operation 542 moves the probe to the next position and repeats conduction test 541. If complete, the probe(s) is removed in operation 544. Number and ablation intensity/energy are set by the particular procedure and the desired permanence. The practitioner selects the procedure/power level 404 (FIG. 4) and controller 401 compares the installed probe via identification 331 (FIG. 4) for compatibility with selected procedure. The practitioner is alerted if the installed probe is incompatible with selected power range 404.

Figure 10:
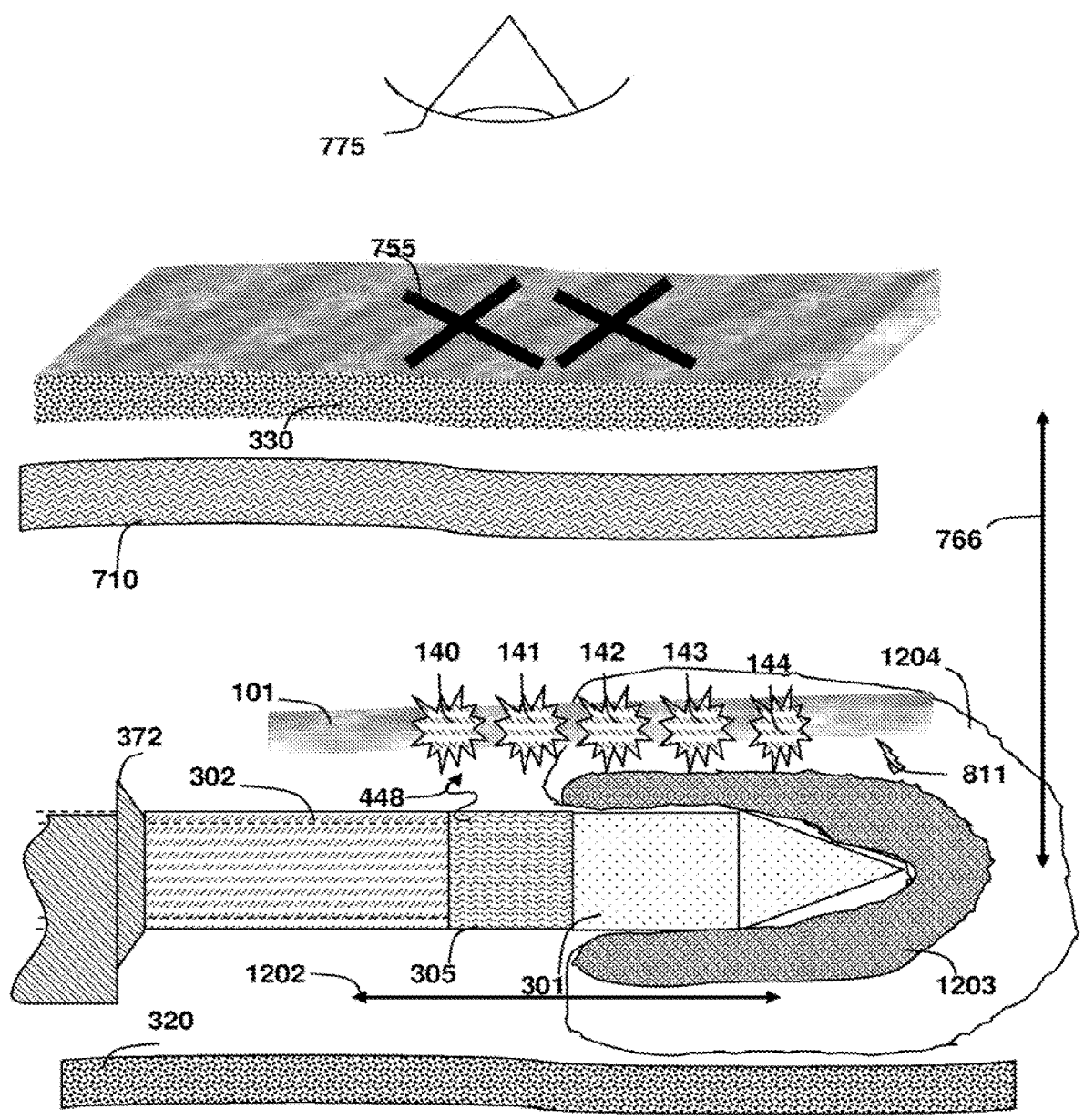
FIG. 10 Side view of visually guided ablation procedure.

As an example and not a limitation, five ablation regions (140, 141, 142, 143, and 144) are shown in FIG. 10. Ablation starts with area 144, then the probe is moved to 143 and so on to 140. Alternatively, movement may be during insertion, moved, laterally, in a circular manner or other manner to enlarge the area of targeted nerve destruction. Nerve responses may be tested after each ablation allowing, the practitioner to immediately check the level of nerve conduction. Probe position and power adjustments are made before applying additional ablations if required. Accurate probe location tools and methods taught herein permit use of minimal, ablation energy thereby minimizing damage to non-target structures. This translates to reduced healing time and minimal patient discomfort. The instant invention gives the practitioner a new tool to perform a minimally invasive nerve conduction limiting procedure with the ability to select, temporary or permanent nerve conduction interruption with a new level of confidence. This new tool offers a low cost procedure performed typically in office or outpatient setting often taking less than one hour with local anesthetic. In contrast to prior art where surgical procedures require stitches and longer healing intervals with limited control of permanence (nerve re-growth).

FIG. 6 Side View of the Bi-Polar Probe 610 With Enhanced Laser Targeting.

Probe insertion and placement is same as taught in FIG. 3. Probe construction is the same as FIG. 3 with the dielectric 305 having embedded optical fibers 690 and 680 providing imaging/illumination. Additional fiber(s) 690-691 are illuminated by a high intensity laser source.

In special cases were target nerve 101 or ablation region 640 is in close proximity to second nerve 111 or skin 330 bi-polar probes 371 or 372 (FIG. 3) create an annular ablation region between electrodes 301 and/or 302, potentially damaging nearby structures such as other nerves 111. With probe 610 in the desired position, laser 608 (FIG. 4) is turned on target 670 (FIG. 6A) with illuminating fiber(s) 690. Fiber(s) transmitting high intensity laser light to ionized region 640 is illuminated by fiber(s) 690. Simultaneous with laser illumination. RF energy 470 is delivered to electrodes 301 and 302. A relatively low impedance path is created by the high intensity laser illumination wherein RF energy will follow this newly created path. Thus very specific regions may be selected for ablation. By permitting operation at a lower power, energy is concentrated where it is needed and eliminates or reduces damage to nearby structures such as skin 330 or nerves 111. Probe 610 improves on the already very precise ablation taught in FIG. 3 with the addition of a low power laser (or other type light source) and fiber delivery system. In the disclosed embodiment a diode pumped Nd:YAG (Neodymium Doped Yttrium Aluminum Garnet) laser is offered as an example and not a limitation.

FIG. 6A Side View is the Florescence Emission Guided Hybrid Bi-Polar Tumor Probe.

Probe construction is similar to FIGS. 3A and 6 with dielectric 305 embedded with a plurality of optical fibers 380, 690, and 680 for illumination detection/imaging. These enhanced systems and processed augments the selective nature of previously disclosed probes. Fiber(s) 690-691 are illuminated by a high intensity light source(s) 608 which is typically a tunable laser or UV LED. Source(s) 608 (FIG. 4) provides illumination for tagged marker(s) 670 in the disclose embodiment where a tunable laser is employed. Excitation/illumination wavelength(s) are specific to the dye/ nano-particle used with marker 670 that is very specific for the desired target 671. The marker/tag is typically a protein specific antigen combined with a florescent marker. The novel probe illumination permits delivery of intense illumination to the target for maximum system sensitivity. Many dyes excited by short (Blue/UV) wavelength light are transmitted poorly in tissue but are easily delivered by fiber 690. A second application offered for hybrid bi-polar ablation probe 610 is for locating/destroying small cancer lesions. The probe addresses cases where surgery is not practical or it dangerous due to location or sub-operable size. Quantum-dot or dye tagged antibody materials 670 are injected into the patients where it attaches to target structure 671. Once tagged, cancer node(s) may be located, tested, and treated.

Figure 7:
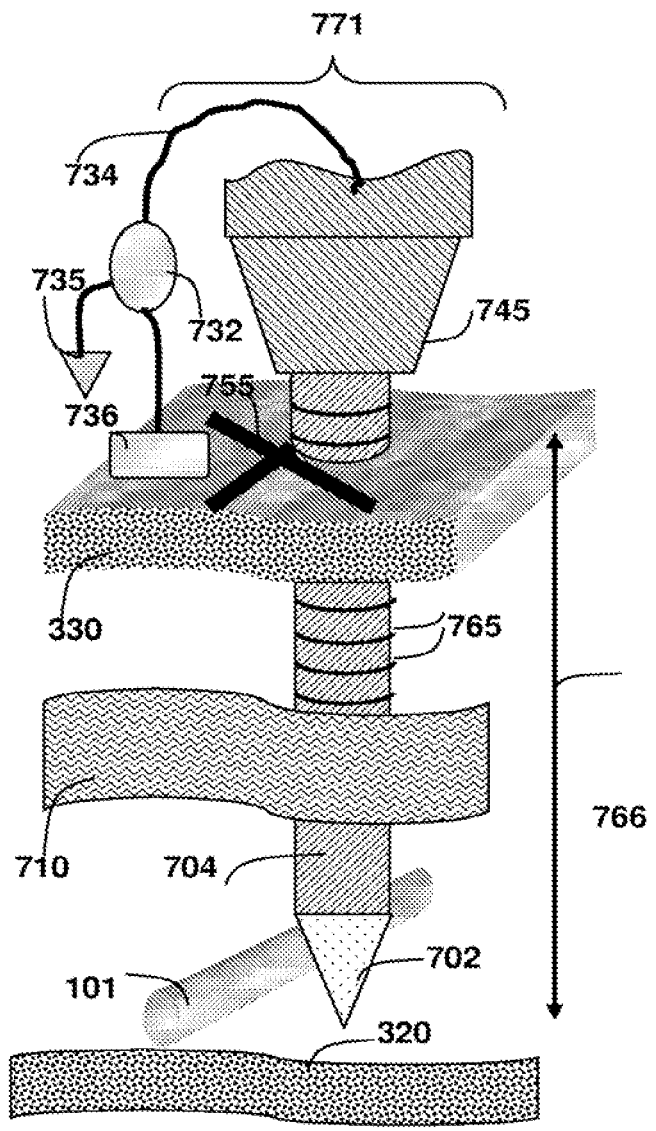
FIG. 7 Side view of auxiliary nerve probe.

FIG. 7 Side View of Auxiliary Single Tipped Nerve Probe

This probe may be used in conjunction with any of the therapeutic probes 371 and their derivatives. The needle itself will be very fine in nature, such as an acupuncture type needle. By its small size, numerous needle insertions may be accomplished with no scarring and minimal pain. The probe 771 will be inserted in the vicinity of the target tissue through skin 330. The exposed tip of 771, 702 will be exposed and electrically connected to generator 732 via wire 734. The surface of probe 771 is covered with dielectric 704 so the only exposed electrical contact is surface 702 and return electrode 736. Exposed tip 702 will be advanced to the vicinity of target 101 and test stimulation current will be applied. Appropriate physiological reaction will be observed and when the tip 702 is properly located, depth will be noted via observing marks 765. External mark 755 may be applied for reference. Ablation probe 371 may then be advanced to the proximity of the target tissue wider the X mark 755 and ablation/nerve destruction as described elsewhere may be performed.

Figure 7A:
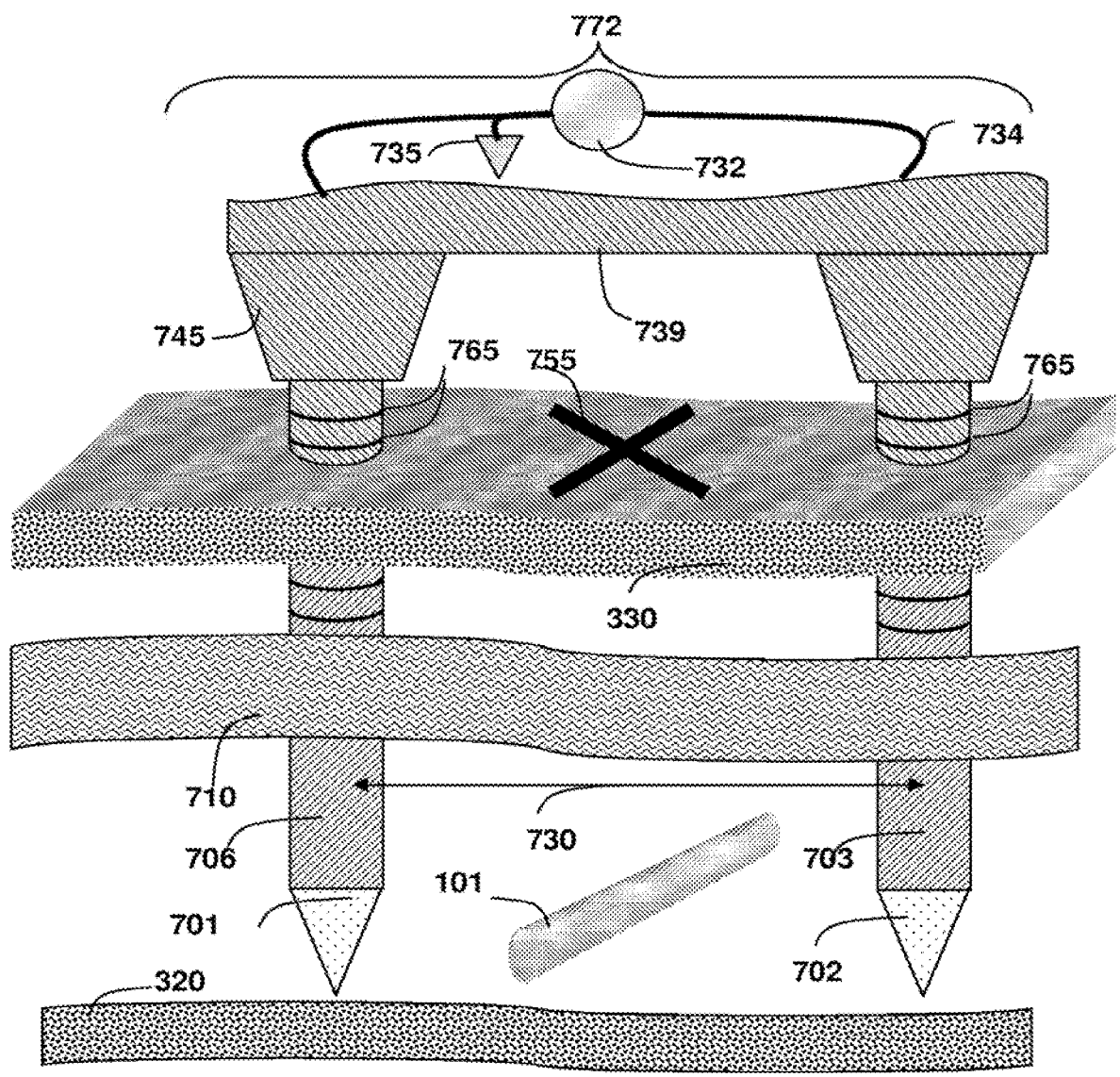
FIGS. 7A and 7B illustrate side views.
Figure 7B:
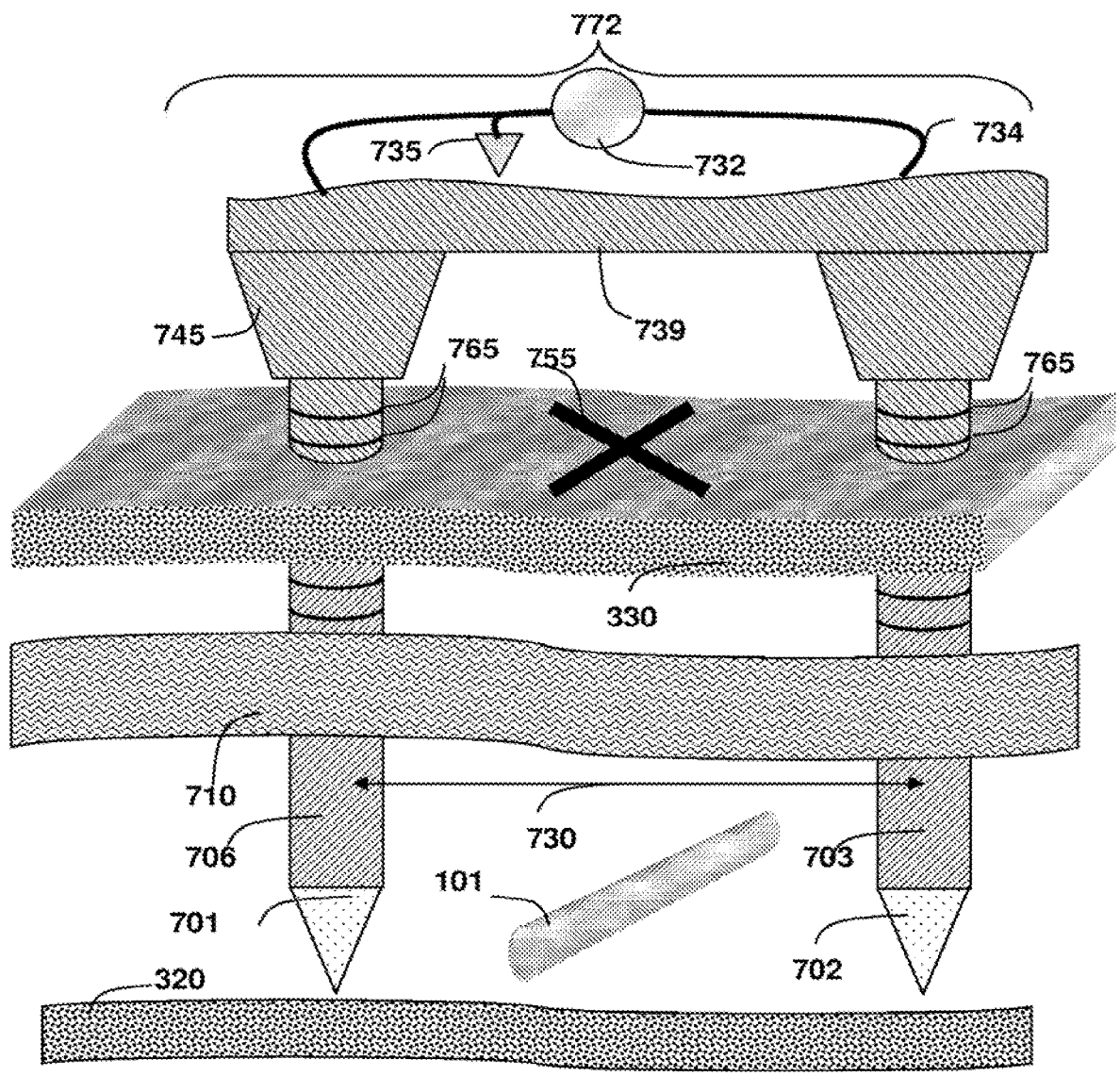

FIG. 7A Side View of Auxiliary Dual-Tipped Nerve Probe.

Dual tipped probe 772 otters an additional embodiment that eliminates return electrode pad 736. Probe frame/handle 739 holds two fine needles, 702 and 701, in the disclosed embodiment that are spaced a short distance (a few mm)-mm apart (730). The shaft of conductive needle 701 is covered with dielectric insulator 706, similar to the construction of probe 771 (FIG. 7). The shaft of the second conductive needle 702 is covered with dielectric insulator sleeve 703. Electric generator 732 provides current to the probes via conductors 734 and 735. Current originates from 701 and returns via electrode 702. Large probe handle 739 is drawn out to teach the dual probes. To aide in probe depth measurement, markers 765 are printed on needle shafts. Dielectric insulating sleeves 703 and 706 isolate the needle shaft current from muscle layer 710. Current applied via generator 732 stimulates the nerve directly while avoiding muscle 710. Smaller probe tips with smaller current permits accurately locating small structures.

Probes 702 and 701 are very small gage needles similar in size to common acupuncture needles, thus permitting repeated probing with minimal discomfort, bleeding, and insertion force. Sharp probes are inserted thru skin 330 and muscle layer(s) 710 near nerve 101. The practitioner locates target nerve 101, then the skin surface may be marked 755 as location aide for ablation step as shown in flow chart (FIG. 5B). Once the desired site of ablation is located, ablation probe(s) 610 (FIG. 6), 371 and related probes (FIG. 3), may be inserted under skin 330, illuminated 448 by tip 305. They are visible through skin (via illumination 448 from tip 305) and are guided to mark 755 (FIG. 8). The observed intensity 765 from illumination source 305 is used as an estimator of measured depth 765. This simple probe system permits rapid, accurate locating of target structures with minimal pain and injury. Accurate target location permits use of lower ablation energy thereby minimizing damage to nearby structures.

FIG. 8 Side View of Guided Ablation Procedure With Auxiliary Nerve Probe(s).

Auxiliary probes 771 and 772 (FIGS. 7 and 7A) are used to accurately locate target structure 101. Probe 771 holds a fine conductive needle 702 that has a shaft covered with dielectric insulator 704. Electric generator 732 provides a small current to the auxiliary probe via conductor 734 and return conductor 735 via return electrode 736. The sharp auxiliary probe is inserted thru skin 330 and muscle layer(s) 710 near target nerve 101. Dielectric insulating sleeve 704 isolates needle shaft from muscle layer 710. Current is applied via generator 732 thereby stimulating the nerve directly while avoiding muscles 710. Prior art probes without insulating sleeve 704 stimulate both the nerve and muscle simultaneously, masking nerve 101 and subsequently making nerve location difficult.

Auxiliary probe 771 and 772 provide a method to quickly locate shallow or deep target structures. Shallow structures are typically marked with ink pen allowing illuminated ablation probe 371 or its equivalents to be quickly guided to mark 755. Optionally, non illuminated probes may be used by the practitioner who simply feels for the probe tip. For deep structures, probe 771 may also be employed as an electronic beacon; small current 811 (which will be lower intensity and different from the stimulating current) from probe tip 702 is used to guide ablation probe 372. Amplifier 430 (FIG. 4) detects current from tip electrode 301 for reading and displays it by controller 401. Alternately probe 701 is used as a receiver detecting current 811 from electrode 301 Moving probe tip 301 horizontally 1202 and in depth 766 relative to auxiliary probe 702 changes current 810 inversely proportional to distance. Detected signal current 811 isolated and buffered by amplifier 430, is measured and the current is displayed to simple bar graph 554 for rapid reading. In addition, audio feedback, in which the tone is modulated b proximity of probe tip 351, 352 or equivalent in relation to auxiliary probe tip 702 is provided to minimize or eliminate the practitioner having to look away from the needle, thus assisting in accurate probe placement. Variable frequency/pitch and volume audio signal are proportional to sensed current 811 that is generated by 452. The tone signal emitted by speaker 451 (FIGS. 4 and 1) provides a pleasant and accurate method to aide in probe placement. Simultaneously, illumination source 408 is modulated by amplifier 456 to blink at a rate proportional to the sensed current. This permits the practitioner to quickly and accuracy guide ablation probe 372 into position using a combination of audio and visual guides. The audio and visual aides also reduce the practitioner's training/learning time. The novel real-time probe placement feedback gives the practitioner confidence that the system is working correctly so he/she can concentrate on the delicate procedure. Accurate probe location permits use of minimal energy during ablation, minimizing damage to non-target structures and reducing healing time and patient discomfort.

Figure 9:
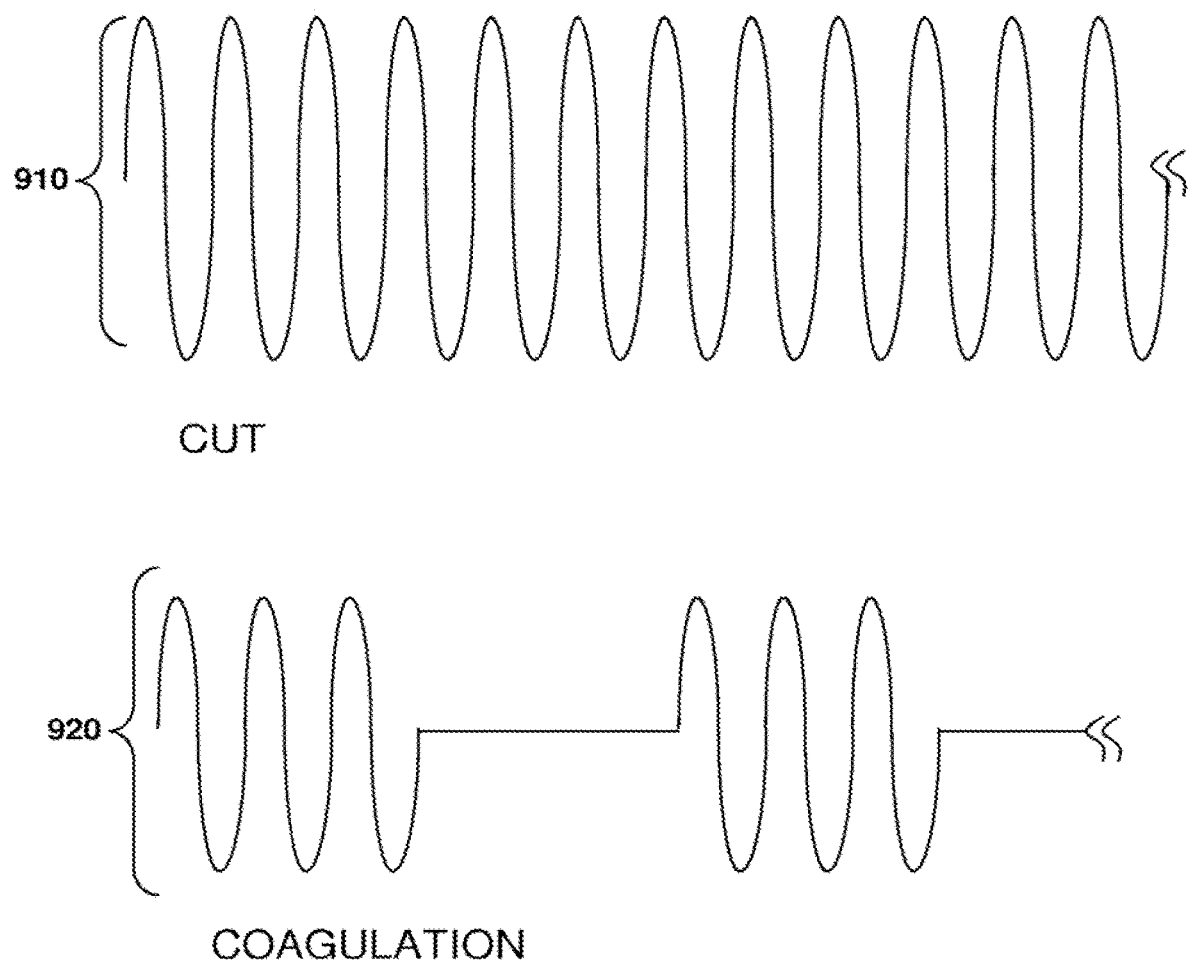
FIG. 9 Sample electro-surgery waveforms.

FIG. 9 A High-Energy Electro-Surgery Sinusoid Cutting Waveform 910.

Lower energy pulse width modulated (or PWM) sinusoid 920 for coagulation is also well known to electro-surgery art. Variations of cut followed by coagulation are also well known.

FIG. 10 Side View of Visually Guided Ablation Procedure.

Auxiliary probes 771 and 772 (FIGS. 7 and 7A) have accurately located target structure 101 and subsequently marked target locations 140 to 144. Shallow structures are marked typically with ink pen (755) allowing illuminated ablation probe 371, 372 or equivalent to be quickly guided to that point. For deep structures, probe 771 is employed as electronic beacon, small current 811 from probe tip 702 is used to guide ablation probe 372 as taught in FIG. 8.

Ablation probe 372 is inserted thru skin 330 and muscle layer(s) 710 near nerve 101. Illumination source 408 permits practitioner to quickly and accuracy guide illuminated 448 ablation probe 372 into position. Illumination 448 from ablation probe as seen by practitioner 775 is used as an additional aide in depth estimation. Selectable nerve simulation current 811 aids nerve 101 location within region 1204. This novel probe placement system gives practitioner confidence system is working correctly so she can concentrate on the delicate procedure. Accurate probe location permits use of minimal energy during ablation, minimizing damage to non-target structures and reducing healing time and patient discomfort.

Region 1203 shows the general shape of the ablation region for conical tip 301. Tip 301 is positioned in close proximity to target nerve 101. Ablation generally requires one or a series of localized ablations Number and ablation intensity/energy are set by the particular procedure and the desired permanence.

Five ablation regions are illustrated 140, 141, 142, 143, and 144; however, there could be more or less regions. Ablation starts with area 144, then the probe is moved to 143 and so on to 140, conversely, ablations could start at 140 and progress to 144. Also, the practitioner could perform rotating motions, thus further increasing the areas of ablation and permanence of the procedure. Between each ablation procedure 540 (FIG. 5A or FIG. 5B), a small nerve stimulation test current 811 is emitted from electrode 301. The approximate effective range of the nerve stimulation current 811 is shown by 1204. Testing nerve response after each ablation allows the practitioner to immediately check level of nerve conduction. Without probe 372 removal, the practitioner receives immediate feedback as to the quality of the ablation. Then minor probe position adjustments are made before conducting additional ablations (if required).

FIG. 1-11A Controller and Probe Data Base Structure

Controller 101 maintains local probe 1460, patient 1430, and procedure 1410 databases. All work together to insure correct probes and settings are used for the desired procedure. Automatically verifying that the attached probe matches selected procedure and verifying probe authentication and usage to avoid patient cross contamination or use of unauthorized probes. Automatic probe inventory control quickly and accurately transfers procedure results to the billing system.

Figure 11:
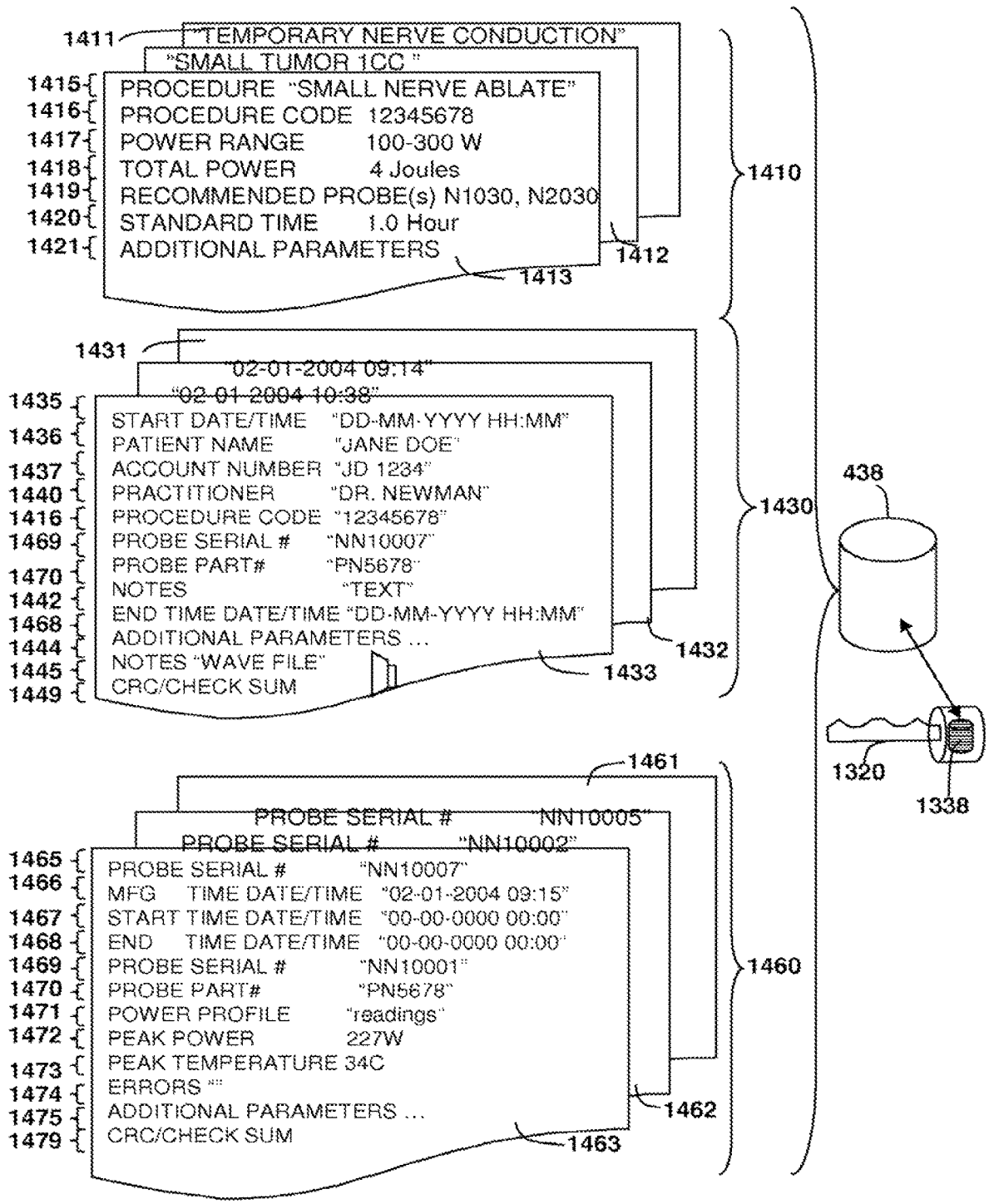
FIGS. 11-11A Controller and probe data base structure.

FIG. 11—Procedure Parameters Code(s) Database 1410

From a touch screen, the practitioner selects the desired procedure from list 1410. For example "TEMPORARY NERVE CONDUCTION" 1411, "SMALL TUMOR ICC" 1412, and "SMALL NERVE ABLATE" 1413 are a few of the choices. Each procedure has a unique procedure code 1416 to be used in the billing system. Power range parameter 1417 is a recommended power setting via power level control 404. The recommended probe(s) Associated with procedure 1415 and power range parameter 1417 are listed in parameters 1419. With the probe connected, the part number is read from memory 331 (FIGS. 1, 3 and 4) and compared to list 1419. The total power parameter 1418 is the maximum energy that the system may deliver for this procedure and is determined by the procedure code, probe being used and software parameters. These parameters may be modified, updated and changed as required by addition of new probes and procedures allowed/approved. Power is delivered, measured and totaled with integrator 435 (FIG. 4). The power integration circuit is designed as a hardwired redundant safety circuit that turns off the power amplifier if maximum energy is exceeded. This novel feature protects patients from system fault or practitioner error. Standard procedure time 1420 is doubled and added to current RTC 482 then written to probe memory 331 (in FIG. 1).

Figure 11A:
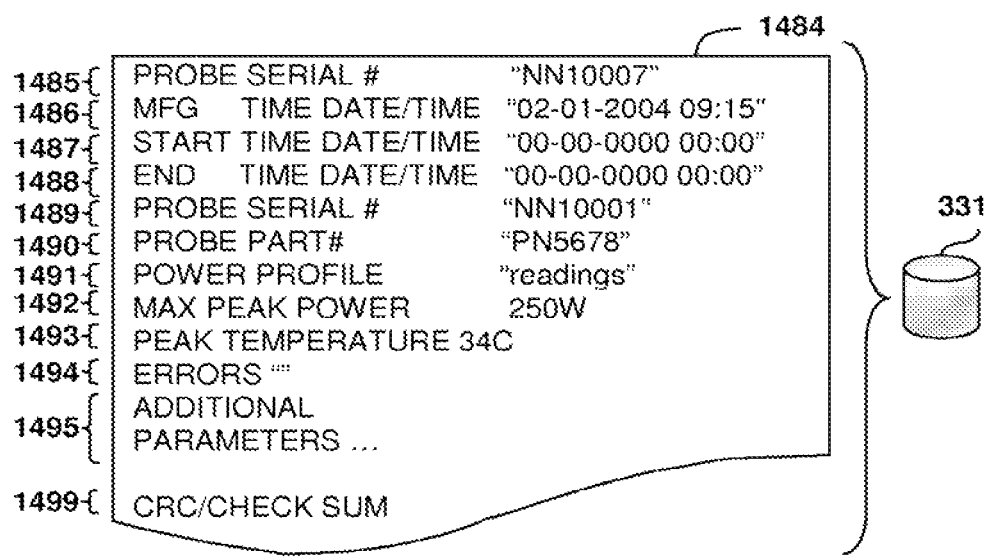

FIGS. 11 & 11A—Probe Usage Authorization Database 1460

Alternative Probe Configurations

Figure 12:
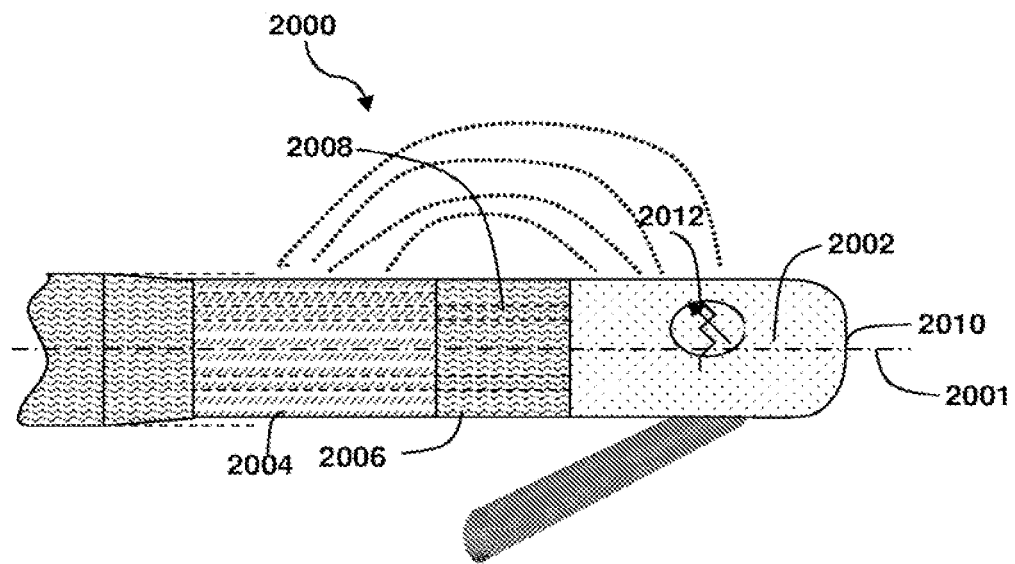
FIG. 12 is a side view of a single axis electrosurgical probe having equal surface area electrodes.

FIG. 12 is a schematic view of an alternative embodiment of a single axis electrosurgical probe 2000 having a longitudinal probe axis 2001, which is similar to the probe of FIG. 3. However, probe 2000 of FIG. 12 features substantially equal surface area conductive electrodes 2002 and 2004 located along a longitudinal axis. A probe 371 also having substantially equal surface area electrodes 301 and 302 is shown in FIG. 3A.

In an equal electrode surface area implementation, one of the conductive electrodes 2002, 2004 may be selectively connected to a stimulation current source or an ablation current source as described above. The other electrode 2002, 2004 may be unconnected or connected as a ground or return path for the connected current source. In the embodiment shown in FIG. 12 conductive electrode 2002 is configured to be connected to the ablation source making electrode 2002 the active electrode. Thus electrode 2004 is in this embodiment a return electrode. Either electrode 2002, 2004 may be connected to a current source or return with appropriate switches.

Since electrodes 2002 and 2004 have substantially equal surface area, the local heating formed upon the application of RF ablation energy to the active electrode 2002 results in a heating zone having a substantially symmetrical ellipsoid form.

The single axis electrosurgical probe 2000 of FIG. 12 also features a dielectric insulator 2006 positioned along the probe axis between the conductive electrodes 2002 and 2004. The dielectric insulator 2006 may have any suitable length, and probes with alternative length insulators may be manufactured for specific ablation procedures. Varying the length of the dielectric insulator 2006 varies the gap dimension 2008 between the electrodes 2002 and 2004. Varying the gap dimension 2008 provides for optimization of the current density within the ablation zone, varies the length of the ablation zone and permits the use of higher voltages, if desired. Thus, the gap dimension may be selected in conjunction with other parameters such as electrode surface area and ablation current to achieve select ablation volumes and tissue temperatures for specific applications.

The probe 2000 of FIG. 12 also features a blunt tip 2010 rather than the conical tip 351, chiseled tip 352 or other tips of FIG. 3. The blunt tip 2010 of FIG. 12 has a smooth rounded profile and is advantageous in certain instances to allow the probe to be easily advanced and maneuvered under the skin minimizing the risk of puncture or the cutting of adjacent tissue or anatomical structures. Thus, a blunt tip 2010 may significantly reduce the bruising or other trauma associated with a procedure.

The probe 2000 of FIG. 12 may include a sensor 2012. The sensor may be a temperature sensor 2012. A temperature sensor provides for active temperature monitoring within the ablation zone. Alternatively, a single axis electrosurgical probe of any configuration may be implemented with a Kalman filter as taught by Conolly U.S. Pat. No. 6,384,384 which patent is incorporated herein by reference in its entirety. Kalman filters are also used to estimate tissue temperature within an ablation volume. Kalman filters are suitable for use where well-defined tissue state changes occur at specific temperatures due to protein denaturation such as the denaturation of collagen at 65 C. Kalman filter temperature monitoring is advantageous because the bulk and cost of a separate temperature sensor can be avoided.

From touch screen 450 (FIGS. 1 and 4) practitioner selects desired procedure from list 1410. Probe 371 and equivalents (FIGS. 3A-D) type is selected from recommended list 1419 and is connected via cable 1334 (FIG. 1) to control unit 101. Once connected, controller 401 (FIG. 4) reads the stored time register from ID memory module 331 (FIG. 1). If start time 1487 read is zero (factory default), current real time clock 482 (FIG. 4) is written to database 1460 in the start time field 1467, 1430 and 1435. Simultaneously, twice the standard procedure time 1420 parameter is added to RTC 482 and written to time register 1487 via serial bus 403. If probe start time 1487 reads (331) non-zero, the value compared to real time clock 482. If greater than current time plus twice the standard selected procedure duration 1420, the controller alerts the practitioner via display 450, speaker 451 and flashing probe illumination 608 of previously probe used condition. To correct the situation, the practitioner simply connects a new sterile probe and repeats the above process. FIG. 13 teaches additional detail regarding probe verification usage and related database operations. Periodically controller 401 performs the above verification to alert practitioner that he/she has forgotten to change probe(s).

FIG. 13 is a schematic view of an asymmetrical single axis probe 2014 also defining a longitudinal probe axis 2015. The probe 2014 features a first conductive electrode 2016 and a second conductive electrode 2018 having different surface areas. In the embodiment shown in FIG. 13, the first electrode 2016 is an active electrode and the second electrode 2018 having a larger surface area is a return electrode. A probe having any surface area ratio between an active and return electrode may be fabricated, and used to achieve specific ablation results. In addition, the relative positions of the active electrode 2016 and the return electrode 2018 with respect to the tip of a given probe may be switched. In one embodiment the ratio of the active electrode 2016 to the surface area of the return electrode 2018 is 1:3. Other ratios including 1:8 may be implemented to achieve specific results. The surface area ratio may further be adjustable using a sleeve or other mechanism which will shield or cover a portion of on or both electrodes thus increasing or decreasing the length of the gap defining dielectric insulator 2019. Generally, asymmetrical electrode surface areas will result in asymmetrical heating and ablation because of the higher current density of the RF ablation energy at the electrode with smaller surface area. For example, upon the application of RF energy to the active electrode of the FIG. 13 embodiment, a tissue volume proximal the active electrode 2016 may be asymmetrically heated due to the greater current density resulting from the relatively small surface area of the active electrode 2016. Asymmetrical tissue heating coupled with precise RF power integration taught herein and various probe geometries permits the formation of selected repeatable and controlled ablation volumes.

Figure 14:
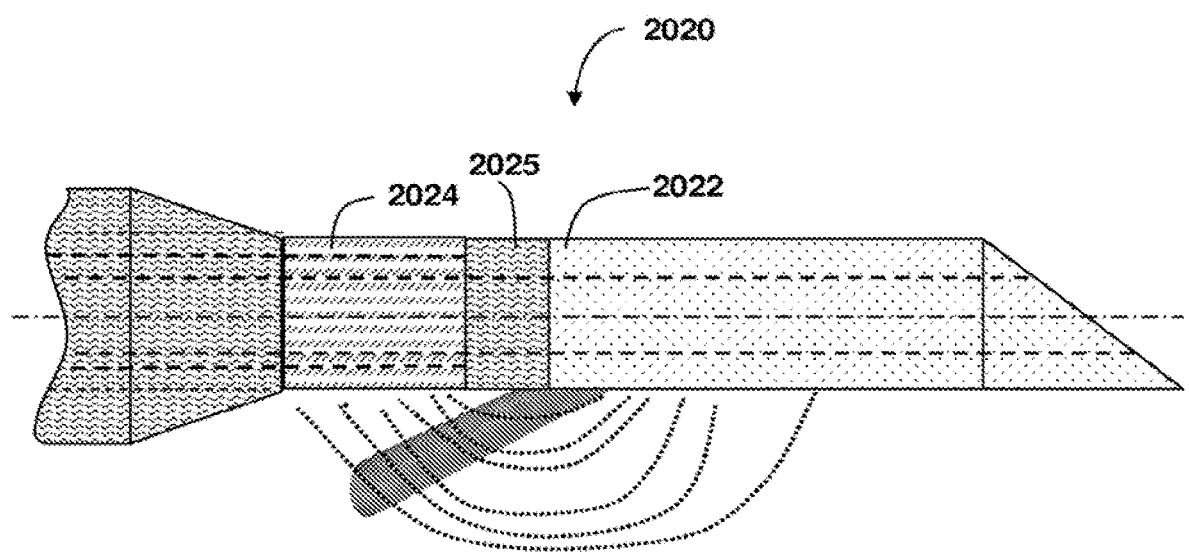
FIG. 14 is a side view of a single axis electrosurgical probe having two electrodes of differing surface areas.

FIG. 14 schematically illustrates an alternative asymmetrical probe 2020, which is similar in many respects to the asymmetrical probe 2014 of FIG. 13. The asymmetrical probe 2020 of FIG. 14, however, features an active electrode 2022 having a surface area greater than that of the return electrode 2024. In the FIG. 14 embodiment current density is higher at the relatively smaller surface area electrode 2024, thus ablation energy is concentrated in the dielectric insulator gap 2025 between the electrodes 2022 and 2024 nearer return electrode 2024 and away from the tip of the probe.

Figure 15:
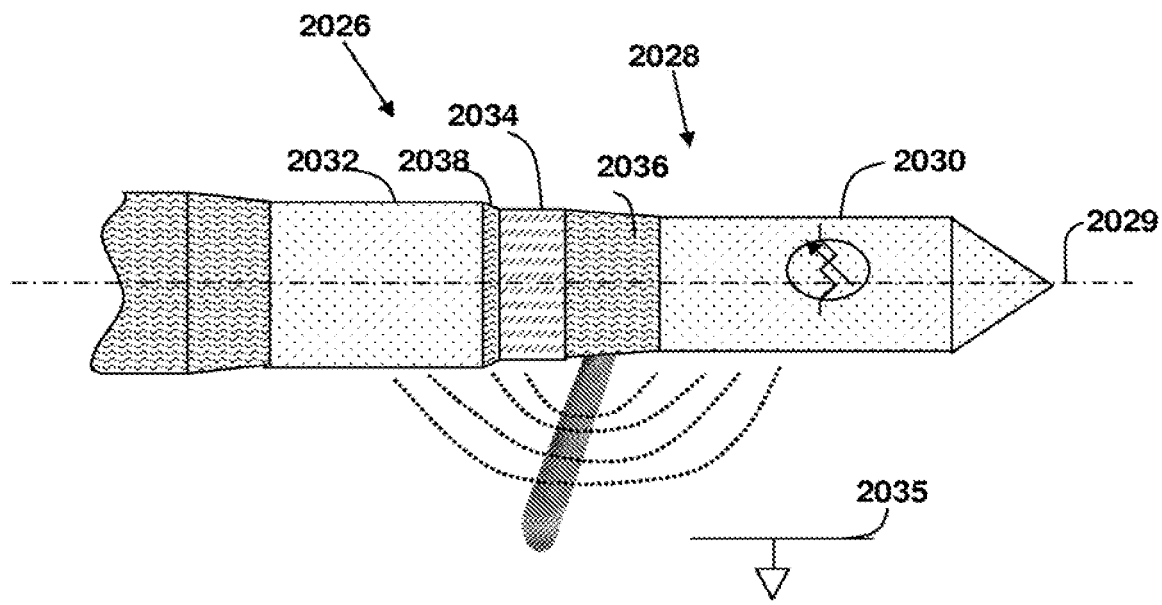
FIG. 15 is a side view of a single axis electrosurgical probe having three electrodes.
Figure 16:
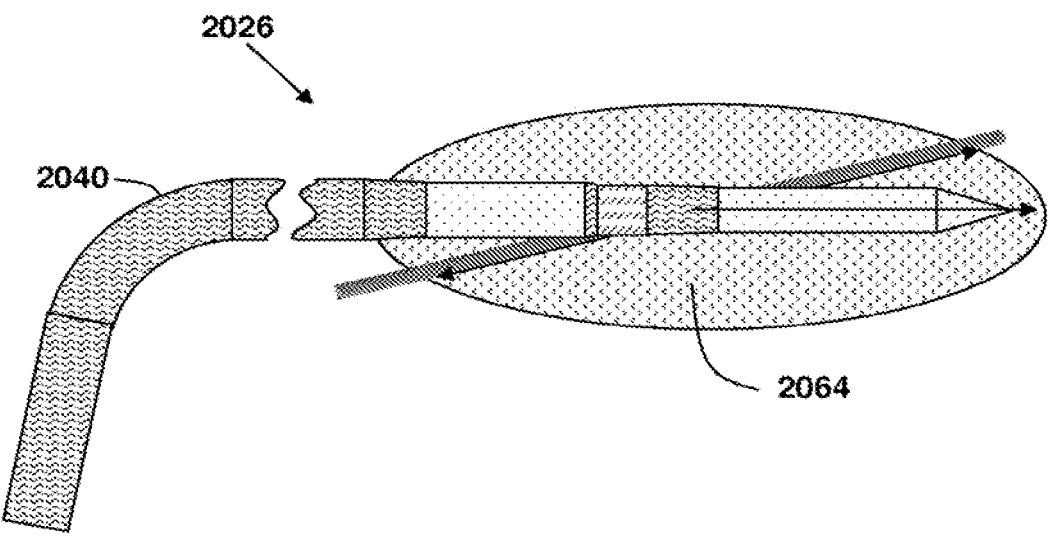
FIG. 16 is a side view of a single axis electrosurgical probe having three electrodes and a curved handle portion.

FIG. 15 is a schematic view of one embodiment of a multiple electrode probe 2026. The multiple electrode probe 2026 includes a substantially needle-shaped probe body 2028 which defines a longitudinal probe axis 2029. More than two electrodes are associated with the probe body and positioned at various locations along the probe axis. In the FIG. 15 embodiment the electrodes include an active electrode 2030, a return electrode 2032, and a stimulation electrode 2034 In this embodiment the active electrode is positioned near the tip of the multiple electrode probe 2026, the return electrode 2032 is positioned away from the tip and the stimulation electrode 2034 is positioned between the active electrode 2030 and the return electrode 2032. It should be noted that the position of the various electrodes with respect to each other and the tip may be varied to achieve specific ablation and probe positioning advantages. In addition, the connection of any given physical electrode as an active electrode, return or stimulation electrode may be varied at the discretion of the user with a simple switching mechanism between the electrode and the ablation or stimulation energy sources. Alternatively, a separate ground or return path 2035 may be utilized with any configuration of electrodes. The various electrodes of the multiple electrode probe 2026 are separated by a first dielectric insulator 2036 and a second dielectric insulator 2038. FIG. 16 schematically illustrates the multi-polar probe 2026 of FIG. 15 with the addition of a curved section 2040 opposite the portion of the probe body 2028 associated with the electrodes. The curved section 2040 may in certain instances allow the practitioner to achieve optimal probe positioning with a minimum of unnecessary tissue disruption. A multiple electrode probe 2026 may be implemented with dielectric insulators 2036, 2038 of varying dimensions, sensors or electrodes of different surface areas, all as described above, to achieve desired ablation results.

Figure 17:
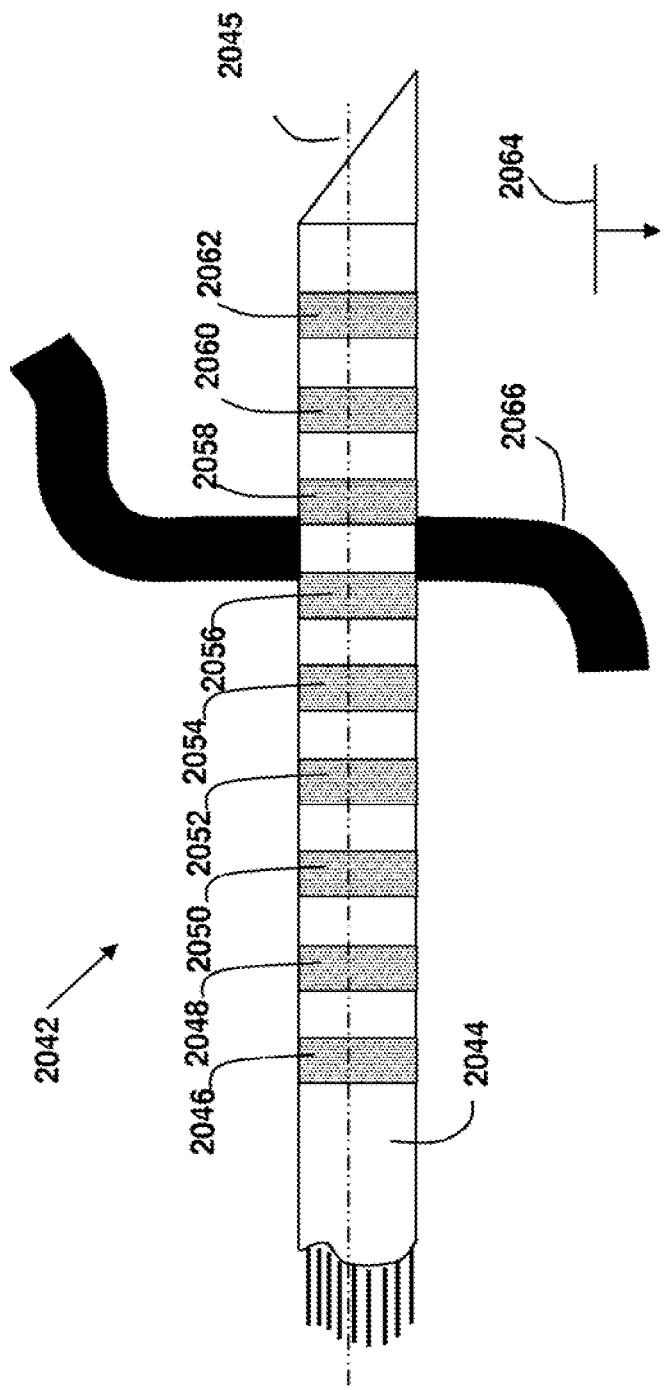
FIG. 17 is a side view of a single axis electrosurgical probe having multiple electrodes transverse a nerve.
Figure 18:
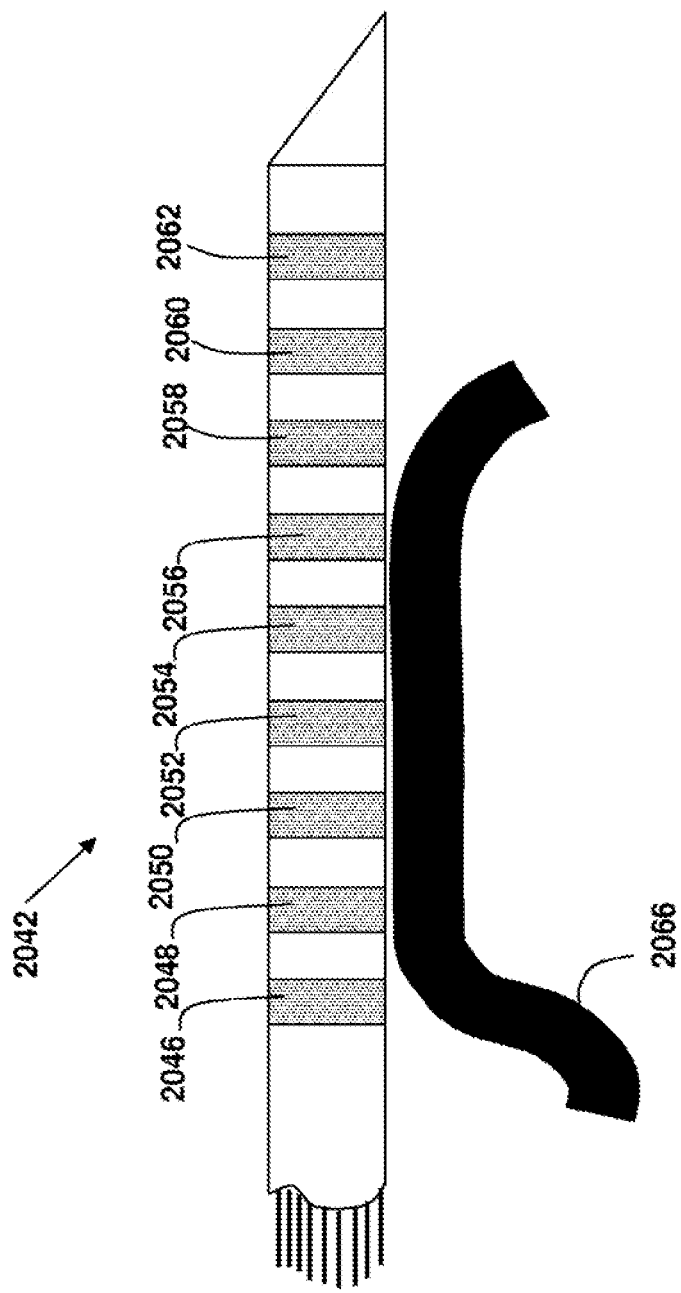
FIG. 18 is a side view of a single axis electrosurgical probe having multiple electrodes parallel to a nerve.
Figure 19:
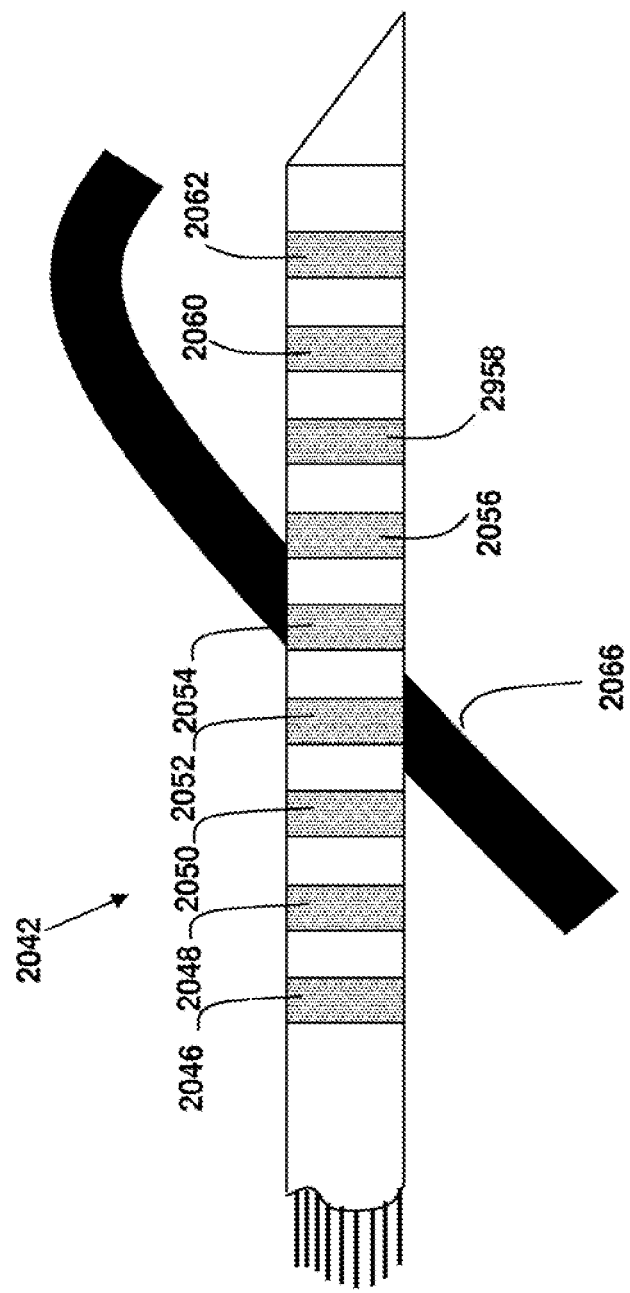
FIG. 19 is a side view of a single axis electrosurgical probe having multiple electrodes crossing a nerve at an angle.

FIG. 17-19 schematically illustrates an alternative embodiment of a multiple electrode probe 2042. The multiple electrode probe 2042 of FIG. 17-19 includes a probe body 2044 which defines a longitudinal probe axis 2045. Multiple electrodes 2046-2062 are associated with the probe body 2044 at separate locations along the probe axis. In the embodiment shown in FIG. 17-19 the electrodes are uniformly sized and spaced. It is important to note, however, that different sizes of electrodes and non-uniform spacing of the electrodes may be implemented to achieve specific ablation results. Preferably, each of the electrodes 2046-2062 may be selectively connected with one or more switches to a stimulation current source, an ablation current source, a ground for the stimulation current source a ground for an ablation energy source or left unconnected. As described in detail below, the flexibility provided by switched connection of each electrode to a current source or ground provides certain advantages in probe location and ablation. In addition, the multiple electrode probe 2042 could be deployed in conjunction with a separate return electrode 2064, typically placed in contact with tissue away from the ablation site.

Placement Methods

Several methods of properly positioning a probe adjacent to a selected nerve for ablation energy application are discussed above. For example, probe placement methods featuring florescence marker dyes, optical probe guidance and electronic probe guidance with the use of low energy nerve stimulation current are discussed in detail. Certain of the alternative probe configurations as illustrated in FIGS. 13-19 provide for refined probe placement methods using variations of the basic electrical stimulation techniques described above.

The single axis electrosurgical probe 2000 of FIG. 12 or the asymmetric probes 2014, 2020 of FIGS. 13 and 14 may each be properly positioned using an iterative technique, as described above with reference to FIGS. 5A-B. The iterative placement method ma be refined for uses with multiple electrode probes such as are depicted in FIGS. 15-19.

For example, the FIG. 15 embodiment of a multiple electrode probe 2026 includes a separate stimulation electrode 2034. The stimulation electrode 2034 is located along the longitudinal axis 2029 of the probe body, typically though not necessarily between an active electrode 2030 and a return electrode 2032. During the stimulation and positioning phases of a probe placement procedure the active electrode 2030, return electrode 2032 or a separate electrode 2035 not associated with the probe body 2028 may serve as the ground for the stimulation current source. As is described above with respect to FIG. 5 a practitioner will typically monitor target nerve response by observing muscle reaction elicited by the stimulation current as the multiple electrode probe 2026 is iteratively guided closer to the target nerve 101. The level of stimulation currently applied may be adjusted to increase or decrease the effective stimulation range depending, upon the muscle response observed by the practitioner. Typically, stimulation current will be continuously or stepwise reduced with a switch or other control to decrease the stimulation range as the stimulation electrode 2034 is guided in close proximity to the subject nerve 101, assuring that the nerve is ultimately placed adjacent to the stimulation electrode.

In probe embodiments where the stimulation electrode is positioned in between the ablation electrodes 2030, 2032, the above described iterative method guarantees that the target nerve is positioned within an elliptical ablation zone 2064 (see FIG. 16) which will be formed between the active electrode 2030 and return electrode 2032 upon the application of RF ablation energy.

FIG. 17-19 shows an alternative embodiment of a multiple electrode probe 2042 placed in various orientations with respect to a target nerve 2066. For example in FIG. 17, the multiple electrode probe 2042 is placed transverse the nerve 2066, in FIG. 18 the multiple electrode probe 2042 is placed parallel to a portion of the nerve 2066 and FIG. 19 shows the multiple electrode probe 2042 placed across the target nerve 2066 at an angle. As is described in detail above, each of the electrodes 2046-2065 may preferably be selectively connected to a stimulation current source, an ablation energy source, a ground or left unconnected. The electrodes 2046-2062 may be connected manually or switched and activated electronically.

The multiple electrodes of the FIG. 17-19 embodiment of the multiple electrode probe 2042 provides for certain advanced placement and ablation procedures. For example, FIG. 17 illustrates a method for locating and selectively ablating a target nerve 2066, which runs substantially transverse the probe at a point along the axial length of the probe 2042. This placement method features the practitioner initially positioning the probe across the target nerve 2066. The electrodes 2046 through 2062 are then activated sequentially with stimulating current, in adjacent active/ground pairs (bipolar mode) or individually with reliance upon an external around 2064 (mono-polar mode). The practitioner may then observe the response of one or more muscles associated with the target nerve as stimulation current is applied to successive electrodes 2046-2062.

For example, with reference to FIG. 17, stimulation current may be applied between electrodes 2046 and 2048. The practitioner notes that there is no corresponding muscle response. Stimulation current may next be applied between electrodes 2048 and 2050. Again, no muscle response is observed by the practitioner. Sequentially, stimulation current is then applied to successive electrode pairs. When the stimulation current is applied between electrodes 2054 and 2056 there may be a mild muscle response. When the stimulation current is applied between electrodes 2056 and 2058 however, a strong muscle response will be observed. Continuing, on, the stimulation is then applied between electrodes 2058 and 2060. Here a greatly reduced muscle response is observed indicating that the nerve is crossing the probe substantially between electrodes 2056 and 2058. Subsequently, ablation energy may be applied between designated electrodes 2056 and 2058 to ablate nerve 2066.

FIG. 18 illustrates a similar nerve location and ablation procedure wherein the nerve 2066 is substantially parallel to and adjacent to the axial length of the probe 2042 adjacent electrodes 2048 through 2056. In this second example the practitioner first applies stimulation current is applied, between electrodes 2046 and 2048. A mild muscle response or no muscle response may be observed. When stimulation current is applied between electrodes 2048 and 2050, a strong muscle response is noted by the practitioner.

Sequentially, the stimulation current is then applied between electrodes 2050 and 2052 with similar strong muscle response observed. This sequential stimulation and response process is observed through the activation of electrodes 2056 and 2058 where the muscle response is substantially diminished or not observable. This is an indication that electrodes 2048 through 2056 are all in contact with the nerve 2042. The electrodes 2048 through 2056 may then be switched to the ablation current source activated and sequentially or simultaneously in bi-polar pairs or individually in bi-polar or mono-polar mode to ablate the nerve 2042. The nerve could be ablated along a select length defined by the number of electrodes activated by the practitioner. This method could also be implemented in mono-polar mode whereby stimulation or ablation energy is applied between one or more electrodes 2046 through 2062 and a separate return electrode applied externally on the body.

FIG. 19 illustrates a substantially similar nerve location and ablation procedure wherein the multiple electrode probe 2042 crosses the nerve 2066 diagonally or at an oblique angle to the probe axis. Thus. FIG. 19 illustrates a method for angular positioning of the probe 2042 relative to the nerve 2066. In this example stimulation current applied as described above at electrodes 2052, 2054, and perhaps 2056 would result in a response in the associated muscle. If a larger number of electrodes elicit a muscle response, this is an indication of a broader nerve/probe contact area resulting from a more parallel contact placement of the probe 2042 relative to the nerve 2066. Such a determination of angular placement can be enhanced by fabricating a probe with relatively short distance between adjacent electrodes, relative to the diameter of a nerve of interest. The practitioner may also maneuver the probe to attain a muscle response from more or less electrodes as desired providing the opportunity to ablate a greater or lesser length of the never without axially repositioning the probe.

The above methods of angular probe positioning and sequential stimulation may be combined with the iterative techniques also described above. For example, the stimulation current generator may be set at a relatively high level initially and reduced when the general location of the nerve with respect to certain electrodes is determined.

For example, the stimulation current threshold (to elicit an observable response) between electrodes 2048 and 2050 of FIG. 19 would be higher than the threshold between electrodes 2050 and 2053. This information could be indicated graphically, numerically or audibly to allow the practitioner to reposition the probe for more parallel or more transverse positioning of probe 2042 relative to nerve 2066.

FIG. 13 is a schematic view of an asymmetrical single axis probe 2014 also defining a longitudinal probe axis 2015. The probe 2014 features a first conductive electrode 2016 and a second conductive electrode 2018 having different surface areas. In the embodiment shown in FIG. 13, the first electrode 2016 is an active electrode and the second electrode 2018 having a larger surface area is a return electrode. A probe having any surface area ratio between an active and return electrode may be fabricated and used to achieve specific ablation results. In addition, the relative positions of the active electrode 2016 and the return electrode 2018 with respect to the tip of a given probe may be switched. In one embodiment the ratio of the active electrode 2016 to the surface area of the return electrode 2018 is 1:3. Other ratios including 1:8 may be implemented to achieve specific results. The surface area ratio may further be adjustable using a sleeve or other mechanism which will shield or cover a portion of one or both electrodes thus increasing or decreasing the length of the gap defining dielectric insulator 2019. Generally, asymmetrical electrode surface areas will result in asymmetrical heating and ablation because of the higher current density of the RF ablation energy at the electrode with smaller surface area. For example, upon the application of RIF energy to the active electrode of the FIG. 13 embodiment, a tissue volume proximal the active electrode 2016 may be asymmetrically heated due to the greater current density resulting from the relatively small surface area of the active electrode 2016. Asymmetrical tissue heating coupled with precise RE power integration taught herein and various probe geometries permits the formation of selected repeatable and controlled ablation volumes.

During, the procedure (FIG. 10), various parameters such as peak temperature 1473, power 1472, impedance, etc . . . are read, scaled, stored and displayed. Parameters such as procedure start 1467; end time 1468, serial number 1469, and part number 1468 are recorded as well. Critical parameters are written to local high-speed memory 438 for display and analysis. On a time permitting or end of procedure, data is mirrored to removable USB 1320 memory stick 1338. Probe specific parameters 1463 are copied and written to probe memory 1338 for use at probe refurbishment facility. Database checksum/CRC(s) 1449, 1479, and 1499 are check and updated as required. Faults such as shorts (dielectric 305 (FIG. 3) breakdown) that are detected are saved to error field 1494 and 1474. If network connection 1305 is available, email request for replacement probe are automatically sent to repair/customer service center 1308. Defective probe 374 with saved failure information 1494 is returned for credit and repair.

Use of a USB memory stick permits continued operation in the event of a network 1326 failure Data is loaded to memory 1338 for simple transfer to office computer 1306 (FIG. 1) for backup. Commonly available USB memory sticks 1320 have large data capacities in the tens to hundreds of megabytes at a low cost with long, retention times. USB memory sticks also can support data encryption for secure transfer of patient data. Sealed versions are available as well compatible with chemical sterilization procedures.

If computer network 1326 such as Ethernet 802.11 or wireless 802.11x is available, files are mirrored to local storage 1309, remote server 1307. The remote server (typically maintained by equipment manufacture) can be remotely update procedure(s). To insure data integrity and system reliability a high availability database engine made by Birdstep of Americas Birdstep technology, Inc 2101 Fourth Ave. Suite 2000, Seattle Wash. is offered as an example. The Birdstep database supports distributed backups, extensive fault and error recovery while requiring minimal system resources.

FIG. 11—Patient/Procedure Database 1430

From a touch screen, the practitioner selects or enters patient name from previous procedure 1430 and creates a new record 1433. Similarly, a procedure is selected from 1410 (for example "TEMPORARY NERVE CONDUCTION" 1411, "SMALL TUMOR ICC" 1412, and "SMALL NERVE ABLATE" 1413). Each procedure has a unique procedure code 1416 that is used for the billing system. Other information such as practitioners name 1440, date 1435 is entered to record 1433. As taught above probe appropriate for the procedure is connected and verified, part 1470 and serial number 1469 recorded.

FIG. 11—Voice and Notes

The practitioner enters additional text notes to file 1442 or records them with microphone 455 (FIG. 5) to wave file 1445 for later playback or transcription. The instant invention permits temporary/permanent nerve conduction interruption. Thus, procedures are performed at intervals from months to years apart. A hands free integrated voice recorder is extremely useful. Detailed text and voice notes made while probing/ablating are also recording specific settings, and patient response. A feature that is very helpful when reviewing treatment progress and saves valuable time instead of writing notes. Practitioners play back voice/wave files 1445 with standard audio tools a his/or hers desk. Audio files 1445 can be sent via email or file transfer for transcription, updating note field 1442.

At the end of procedure, records are updated and stored to memory 438. Backup copies are written to USB 1320 memory stick 1338 (FIG. 1). If computer network 1326 such as Ethernet 802.11 or wireless 802.11x is available, files are mirrored to local storage 1309, remote server 1307. Patient name 1436, procedure date 1435, and procedure codes 1416 are automatically transferred via network or USB device 1320 to billing system 1306. USB memory stick permits continued operation in the event of a network 1326 failure. Data is loaded to USB memory 1338 for simple transfer to office computer 1306 (FIG. 1) for backup. USB memory sticks 1320 have large data capacities in the tens to hundreds of megabytes at a low cost with long retention times. USB memory stick also support data encryption for secure transfer of patient data. Insuring, patient is accurately billed with minimal office paper work. Probe inventory is automatic maintained with replacement probes automatic shipped as needed.

The probe 2000 of FIG. 12 also features a blunt tip 2010 rather than the conical tip 351, chiseled tip 352 or other tips of FIG. 3. The blunt tip 2010 of FIG. 12 has a smooth rounded profile and is advantageous in certain instances to allow the probe to be easily advanced, and maneuvered under the skin minimizing the risk of puncture or the cutting of adjacent tissue or anatomical structures. Thus, a blunt tip 2010 may significantly reduce the bruising or other trauma associated with a procedure.

The apparatus and methods described above may be implemented with various features which enhance the safety, ease of use and effectiveness of the system. For example, the probe may be implemented with an ergonomic and functional handle which enhances both operational effectiveness and provides for the implementation of safety features. Individual probes may be carefully managed, preferably with system software to assure that a selected probe functions properly, is sterile and not reused, and that the proper probe is used for each specific treatment procedure. Similarly, safeguards may be included with the system to assure that the operator is certified and trained for the specific treatment protocol selected. Various treatment management methods and specific treatment therapies may be selected for both the best results and for enhanced patient safety. In one embodiment, the treatment, therapeutic, and safety methods may be implemented with and rigorously controlled, by software running on a processor associated with the ablation apparatus and system as is described in detail below.

System Management Method

The concurrent goals of patient safety, procedure efficiency and therapeutic success can be advanced through an effective system management method. A system management method such as is described herein may be implemented through computer software and hardware including, computer processors and memory operating within or in association with the control console and the probe system described herein. Various interfaces between a practitioner, the control console, and the probe system may be present. In addition the hardware associated with an ablation system, including the probe stimulation current source, ablation current source, and the probe system may be in communication with and provide feedback to the system processor. Alternatively, the steps of the system management method could be implemented manually.

In a software and processor based system embodiment, the techniques described below for managing an electrosurgical probe and system may be implemented as a method, apparatus or article of manufacture using standard programming and/or engineering techniques to produce software, firmware, hardware, or any combination thereof. The term "article of manufacture" as used herein refers to code or logic implemented with or stored upon a medium or device (e.g., magnetic storage medium such as hard disk drives, floppy disks, tape), optical storage (e.g., CD-ROMs, optical disks, etc.), volatile and non-volatile memory devices (e.g., EEPROMs, ROMs, PROMs, RAMs, DRAMs, SRAMs, firmware, programmable logic, etc.). Code in the computer readable medium is accessed and executed by a processor. The code in which implementations are made may further be accessible through a transmission media or from a file server over a network. In such cases, the article of manufacture in which the code is implemented may comprise a transmission media such as network transmission line, wireless transmission media, signals propagating through space, radio waves, infrared, optical signals, etc. Of course, those skilled in the art will recognize that many modifications may be made to this configuration without departing from the scope of the implementations and that the article of manufacture may comprise any information hearing medium known in the art.

In a software and processor based system embodiment, the techniques described below for managing an electrosurgical probe and system may be implemented as a method, apparatus or article of manufacture using standard programming and/or engineering techniques to produce software, firmware, hardware, or any combination thereof. The term "article of manufacture" as used herein refers to code or logic implemented with or stored upon a medium or device (e.g., magnetic storage medium such as hard disk drives, floppy disks, tape), optical storage (e.g., CD-ROMs, optical disks, etc.), volatile and non-volatile memory devices (e.g., EEPROMs, ROMs, PROMs, RAMs, DRAMs, SRAM's, firmware, programmable logic, etc.). Code in the computer readable medium is accessed and executed by a processor. The code in which implementations are made may further be accessible through a transmission media or from a file server over a network. In such cases, the article of manufacture in which the code is implemented may comprise a transmission media such as network transmission line, wireless transmission media, signals propagating through space, radio waves, infrared, optical signals, etc. Of course, those skilled in the art will recognize that many modifications may be made to this configuration without departing from the scope of the implementations and that the article of manufacture may comprise any information bearing medium known in the art.

Figure 20:
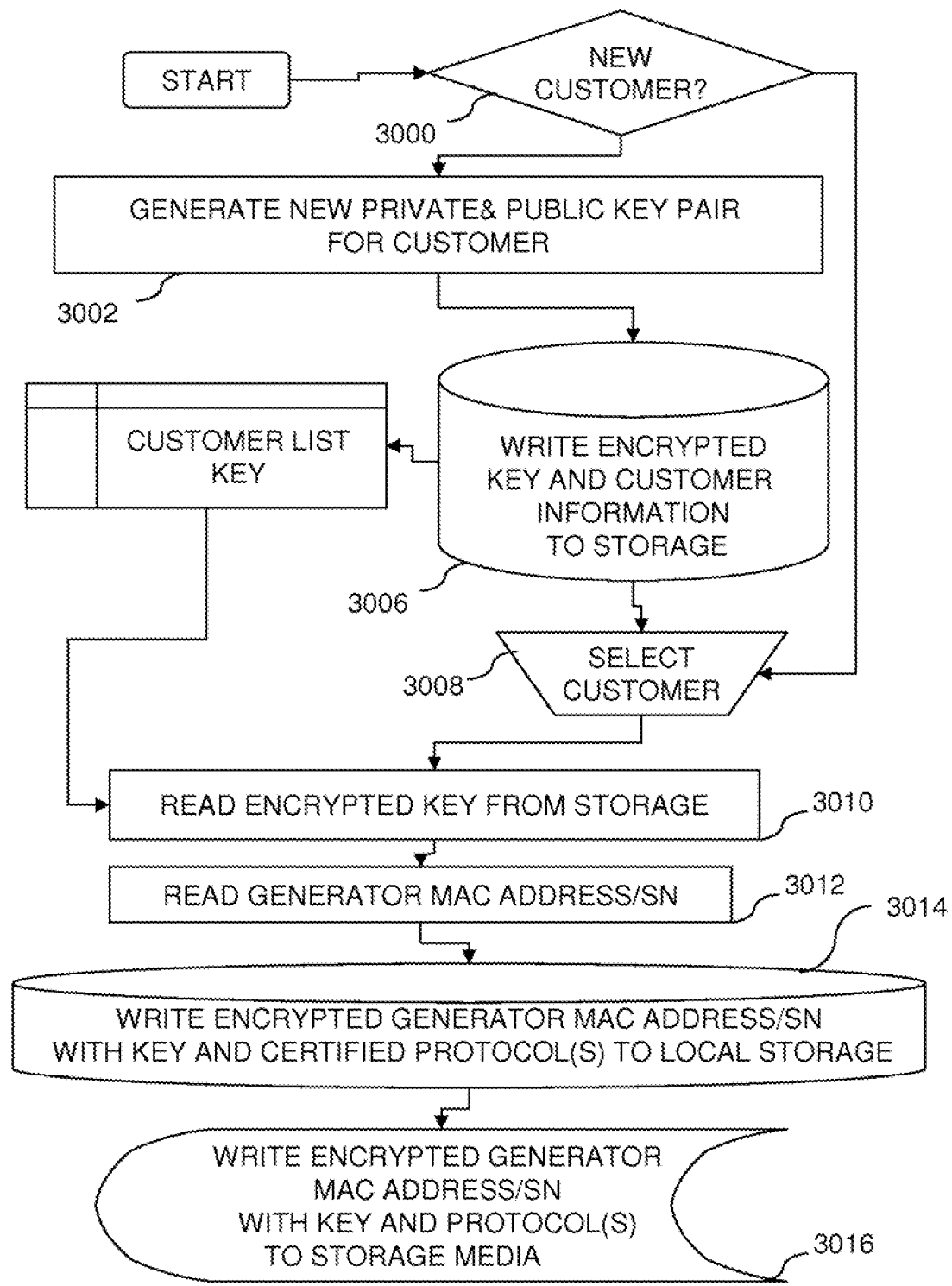
FIG. 20 is a flowchart illustrating certain aspects of a system management method consistent with the present invention.

One aspect of a system management method consistent with the present invention is illustrated in FIG. 20. FIG. 20 shows certain steps associated with a method of managing the "customers" of a treatment system provider and the setup of the customer's system prior to delivery, recognizing that the customers of the system providers are physicians, surgeons and other practitioners who provide therapeutic treatment. The method begins with a determination of the status of a select practitioner as a new customer or a returning customer of the system provider (step 3000). If the practitioner is new, a new private and public key pair is generated (step 3002) using any one of many well-known public-key cryptosystems or similar technologies. For example, Lu, et al. U.S. Pat. No. 4,306,111 discloses a representative cryptosystem, which patent is incorporated herein by reference. Public and private keys and other customer information such as identification or billing information associated with the practitioner are stored to a database (step 3006). Prior to performing any system setup procedure, a setup operator must select the new or previously stored practitioner data from the database (step 3008). The private key for the selected practitioner is read from the stored list (step 3010). Steps 3012, 3014 and 3016 include reading a serial number or media access control address (MAC address) from the men associated with an electrosurgical system using the MAC address or serial number as a seed for a hashing function to encrypt a private key for storage in the system memory. As discussed above in paragraphs 0194-0195, the system memory is in communication with the control for the system stimulation and ablation current sources. Thus implementation of the steps illustrated on FIG. 20 assures that the system (when provided to a practitioner) may be used to deliver only certain treatment protocols associated with the selected practitioner in accordance with the practitioner's established license, training and certification, as is described in greater detail below.

Figure 21:
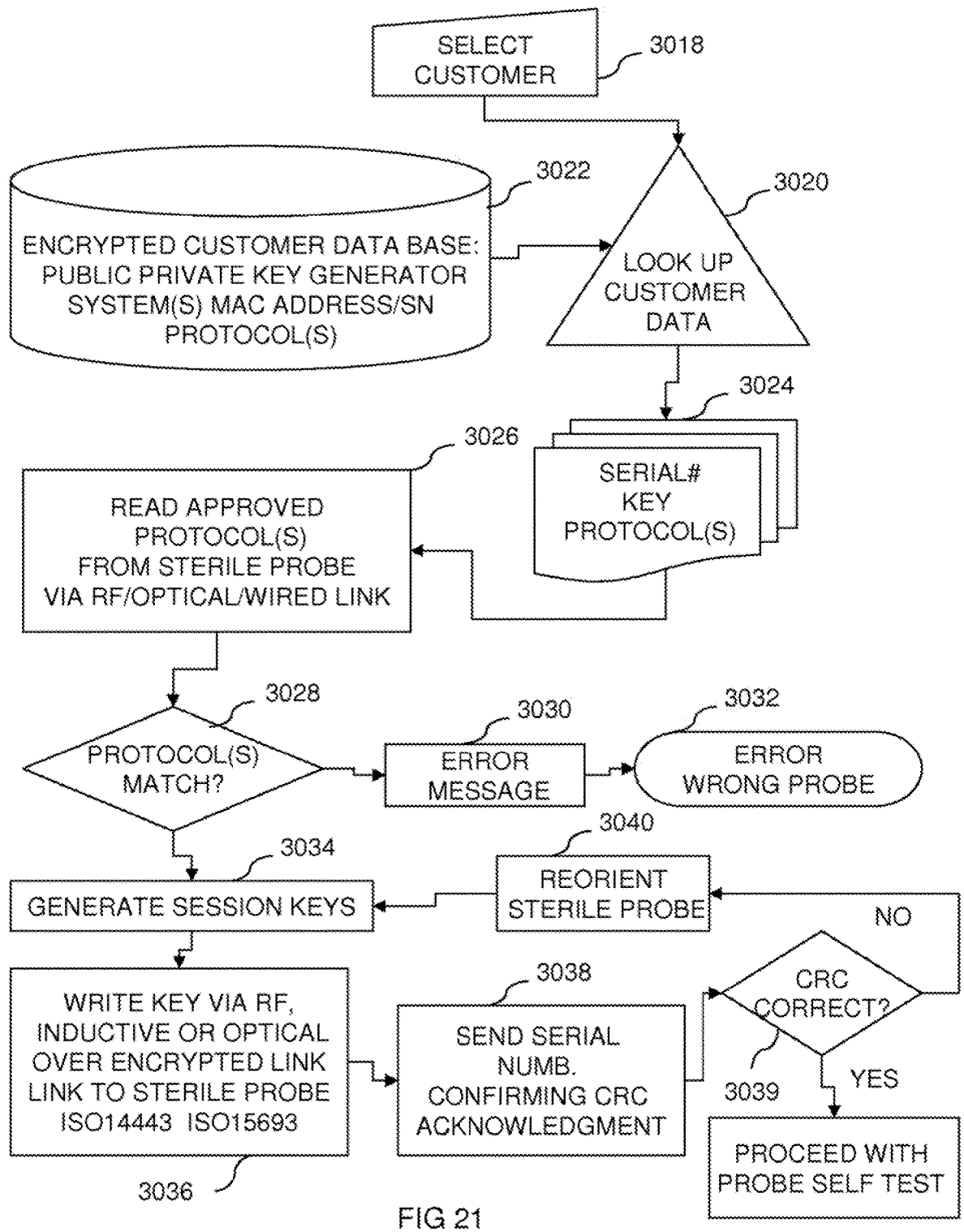
FIG. 21 is a flowchart illustrating certain aspects of a system management method consistent with the present invention.

FIG. 21 includes a flow chart of the probe selection and ordering aspects of the system management method. As is described in detail herein, specific probes having specific physical parameters and energy delivery capacities may be prescribed or selected for the various ablation or nerve block procedures a practitioner may desire to perform. The following steps assure that the practitioner orders a correct probe from a probe manufacturer or distribution center and that the correct probes may be used only according to the intended treatment procedure and the practitioner's current license or certification. As described below, additional steps also assure that the correct treatment protocol is delivered through the correct probe thereby enhancing patient safety and treatment effectiveness.

The probe ordering process begins with order information provided by the system or the practitioner Selection of the customer/practitioner (step 3018) and retrieval of the practitioner's data (step 3020) from the encrypted customer database (step 3022) follows. Previously stored practitioner data may be retrieved and if necessary decrypted (step 3020, step 3022). Most importantly the prescribed probe protocols associated with the practitioner's system and certifications are determined (step 3024). At this point, the probe which is being ordered must be matched with the protocols of intended use and the practitioner's registered system, license and certification data. This match could be accomplished manually; however, manual probe ordering introduces the possibility of human error. Preferably, a sterile packaged probe is interrogated via RF, optical or wired link for approved treatment protocols. For example, the probe may be interrogated for approved protocols over a communications link (step 3026). This step may occur at the probe distribution location. In one embodiment the communications link is an RF link using ISO18000 part 3 protocol operating at 1156 Mhz. Other suitable wired or wireless communication strategies could be used as well. A determination must be made whether the probe matches the allowed treatment protocols associated with the practitioner's system (step 3028). If no match occurs, an error message will be delivered in an automated implementation (step 3030 and step 3032). If a match is registered, session keys for use by hashing functions will be generated (step 3034). The session keys and other information are then written to memory associated with the selected sterile probe (step 3036). In step 3038 the probe serial number is returned to the system and a cyclic redundancy check (CRC) or other hash function is performed to verify both the correct serial number and proper information storage (step 3039), in a wireless implementation an incorrect CRC may result from communications failure. In this case, the probe may be reoriented for a better signal (step 3040). Upon the completion of probe ordering, a probe self test will typically be completed, before the probe is sent to a customer/practitioner.

Figure 22:
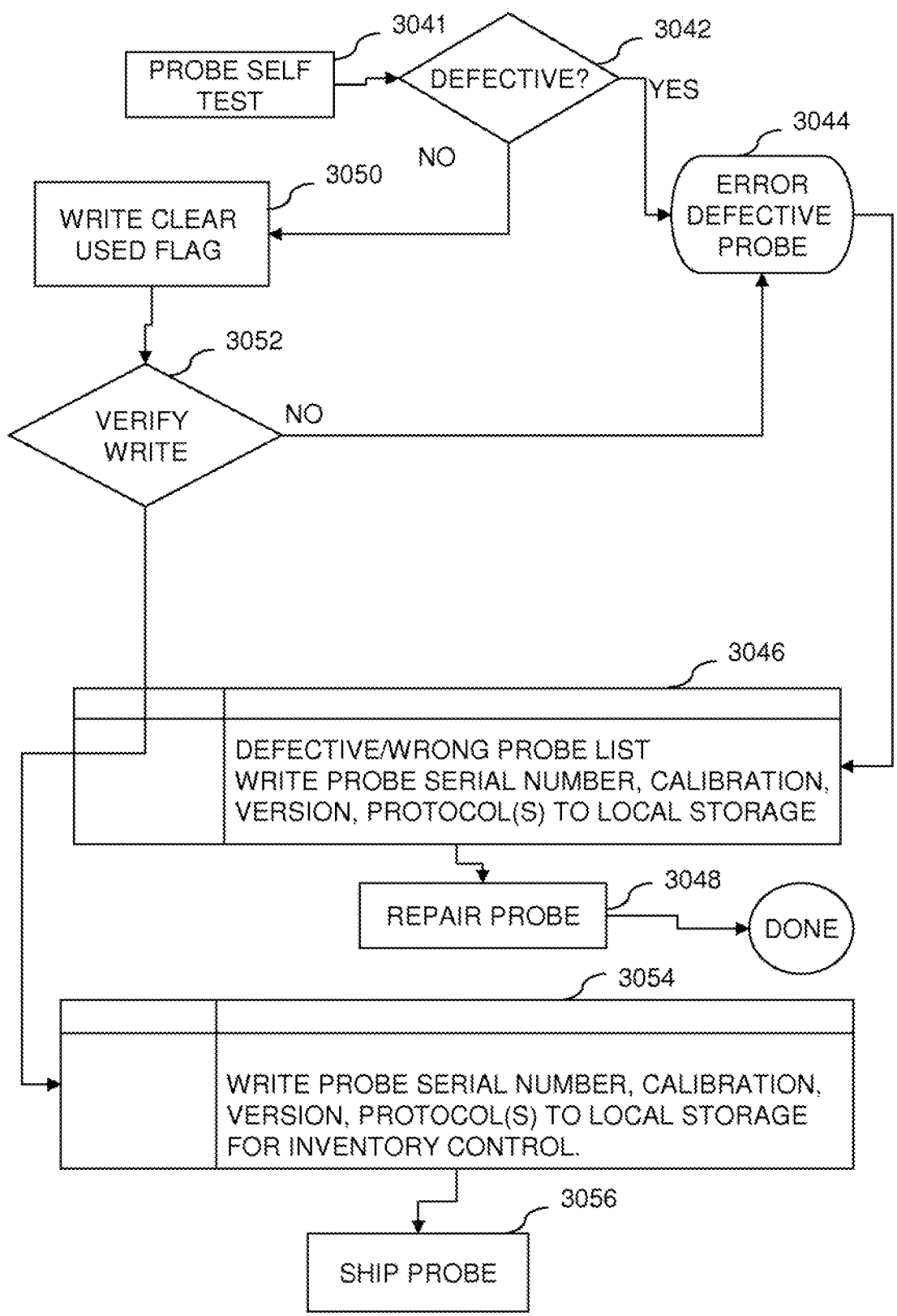
FIG. 22 is a flowchart illustrating certain aspects of a system management method consistent with the present invention.

FIG. 22 illustrates in flow chart form a wireless communication probe self-test. Accuracy and patient safety may be enhanced if the probe self-test occurs while the probe is still in a sterile container. Self-test is preferably accomplished prior to the delivery of a probe to a practitioner. After the correct probe is ordered as described above, a command to a start self-test is issued in step 3041. A rectified RF field can be used to power a processor and/or memory 331 associated with a preferred "smart" probe (See FIG. 1). One embodiment of the probe uses, for example, an Atmel AT90SC6408RFT power processor. This processor is particularly suitable for a smart probe since it includes security features such as: OTP (One Time Programmable) EEPROM area, RNG (Random Number Generator), side channel attack countermeasures, hardware DES/TDES, CRC, ISO 14443 Type A & B contactless and serial interfaces. A smart probe could also be implemented with other processors. An alternative embodiment of the probe, requiring identification only with less security functionality may be implemented with, for example an Atmel AT88SC0204CRF 2-Kbit user memory with authentication and encryption, an ISO/IEC 14443 Type B chip or other less full featured processor.

In step 3041 the processor tests internal memory, the proper operation of the temperature sensor 311 and possibly other matters. A defective probe will generate an error message (step 3042 and step 3044). In such case the defective probe serial number will be written to local storage before the probe is sent for repair (step 3046 and step 3048). A probe passing self-test operation 3041 will be subject to a write clear of the used probe flag as discussed in more detail below (step 3050). Verification of the write clear of the used probe flag is performed (step 3052), with a failed verification resulting in the error notification and repair steps 3044-3048. If the write clear of the used probe flag is verified, the serial number of the probe is written to a record for inventory control (step 3054). This method permits the select probe to be tracked to a specific end user. The public key system detailed above keeps any given probe from accidentally or intentionally being used in non-certified equipment. Once the probe is self-tested it may be shipped to the practitioner (step 3056).

The methods detailed above and illustrated on FIGS. 20-22 include steps which will enhance patient safety and ultimate procedure effectiveness prior to the time a probe or system is delivered to a practitioner for the performance of an ablation, nerve block or other electrosurgical procedure. Additional steps may be included in the system management method which provides protection immediately prior to or during a procedure. The FIG. 23 flowcharts illustrate certain probe usage and safety features which may be implemented immediately prior to or during a therapeutic procedure. In step 3060 of FIG. 23A a probe is removed from sterile packaging and connected to an ablation or stimulation current source control system such as the generator 400 of FIG. 1. The processor associated with the control console establishes communication with the probe over a serial bus 403, an RF Link, or through another communication pathway (step 3062). A failure of the communication link will result in a prompt to reconnect the probe (step 3064 and step 3066). Successful establishment of communication causes a date and time to be read for the generation of session codes for hashing functions (step 3067 and step 3068). In step 3070 the system reads the probe serial number, public key(s) and certified protocols generated and stored as described above. The system may then verify that the private key associated with the generator and the public key match (step 3072). This step assures that a properly ordered probe can only be used in an authorized system. If no match is observed, an error massage is displayed (step 3074).

Assuming, that the probe and control system or generator keys match, the system performs a pre-use probe self-test and calibration (step 3076). At this point in the process, the probe might be identified as defective, out of calibration or the prior use flag associated with the probe might be active, indicating a non-sterile probe which will result in an appropriate error message (step 3078 to step 3084). When a probe passes self-calibration, the serial number is read and the selected treatment protocol or selected energy bolus is matched with the authorized protocols for the probe (steps 3086 and 3088). In the event of a mismatch, an error message may be generated (step 3090). If a successful match is found the practitioner may insert the probe to perform a therapeutic protocol (step 3094). Representative therapeutic protocols are described above in Paragraphs 0163-0170 and illustrated in FIGS. 5A-5B.

Figure 23A:
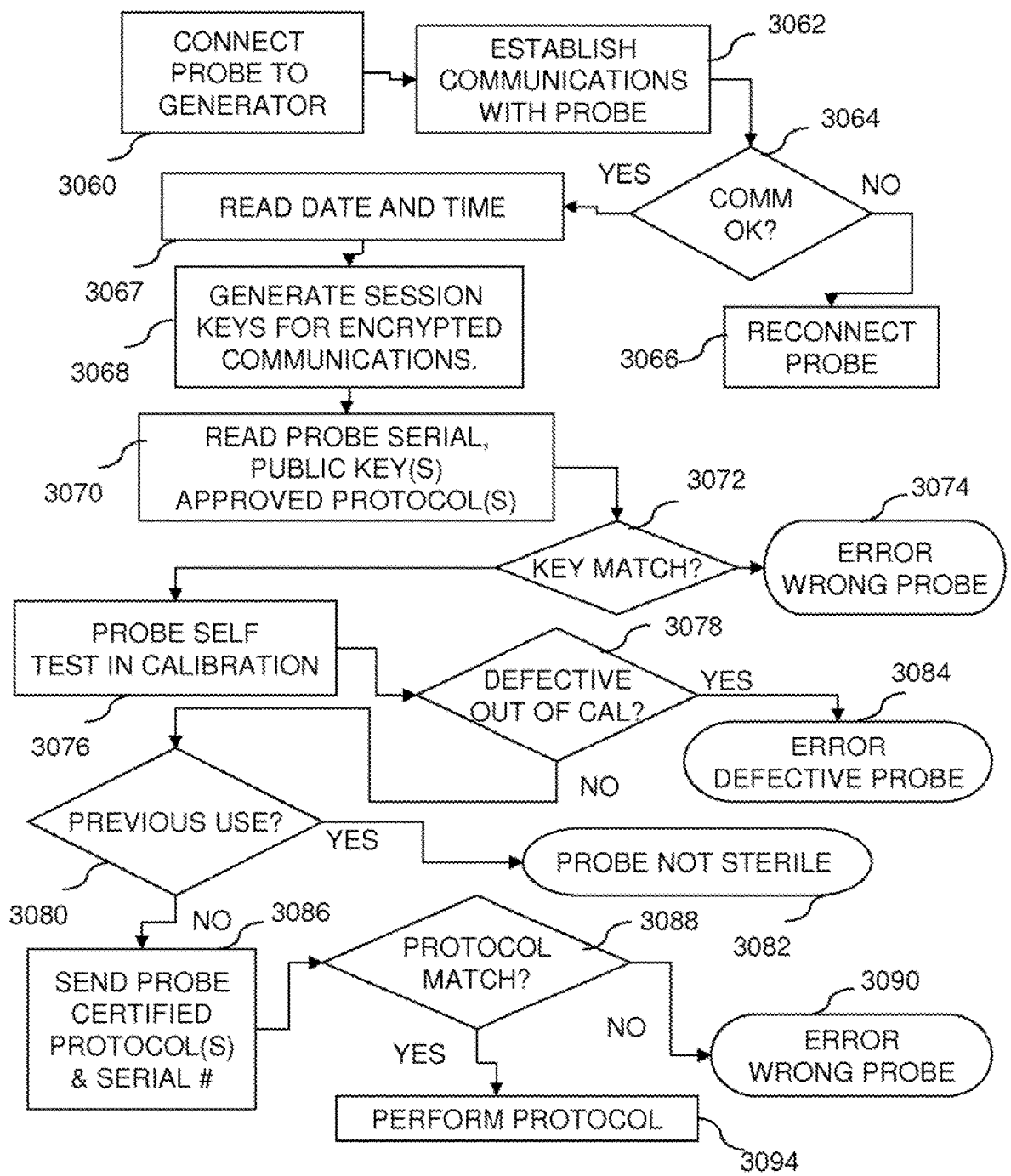
FIG. 23A is a flowchart illustrating certain aspects of a system management method consistent with the present invention.
Figure 23B:
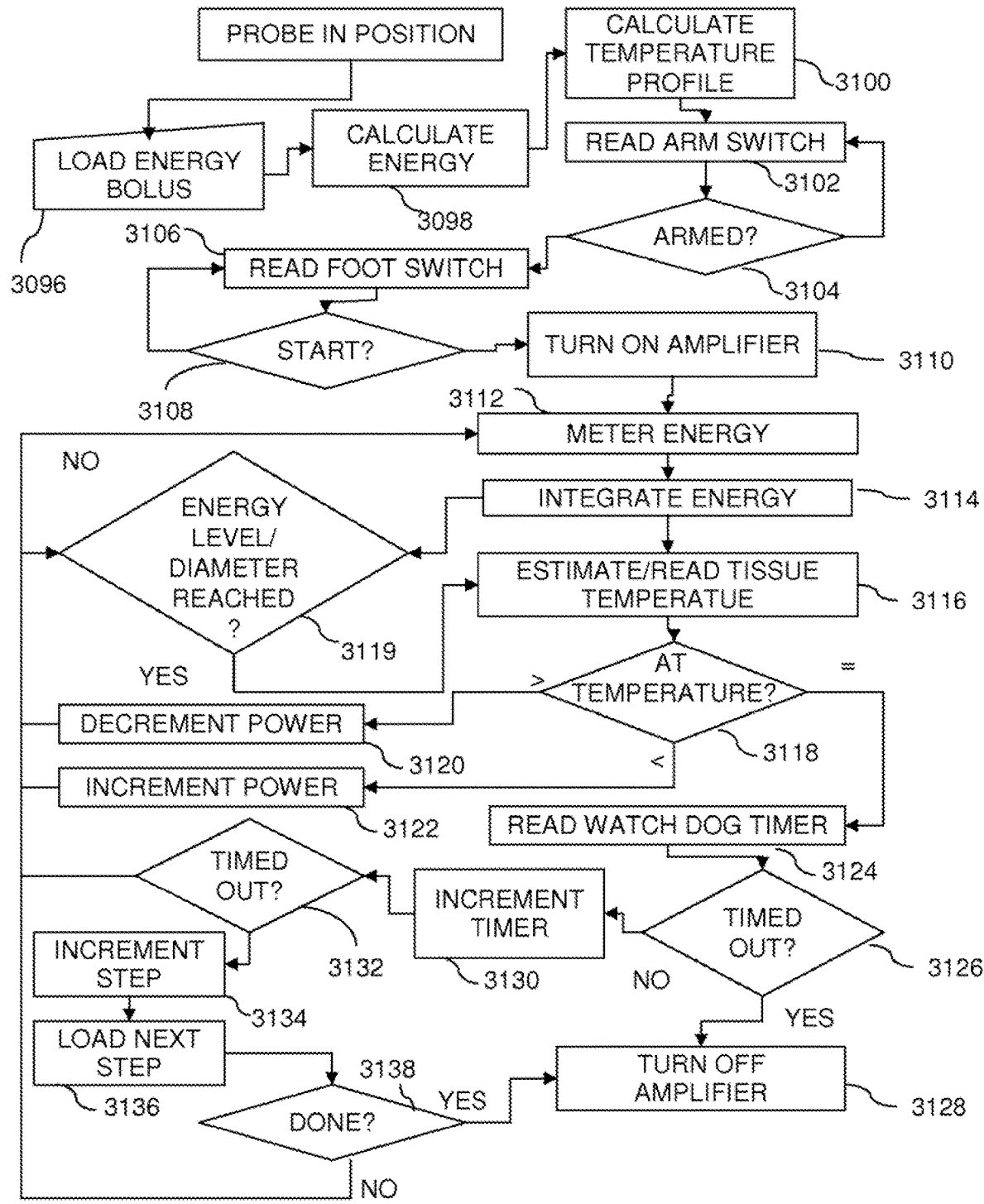
FIG. 23B is a flowchart illustrating certain aspects of a system management method consistent with the present invention.

As shown on FIG. 23B, with the probe in position, a treatment protocol, alternatively known as an energy bolus may be loaded into the generator system (step 3096). The total energy required by the selected bolus is calculated (step 3098) and an estimated temperature profile is calculated (step 3100) from a known energy delivery profile. The operator may press a front panel arm switch or otherwise arm the system once the practitioner has received consent of the patient to proceed. The system reads the arm switch (step 3102) and verifies the system to be armed (step 3104). A supplemental practitioner arming step, for example, a foot switch, further assures patient safety. Thus, the practitioner may press a foot switch to enable the delivery of RF energy when ready. The system reads the activation of the foot switch (step 3106) and waits until the practitioner requests energy delivery (step 3108) at which point the amplifier is turned on (step 3110).

Real power is then measured (step 3112) as energy is delivered with power being integrated (step 3114) for total energy delivered. The optional probe temperature sensor is read and or a temperature profile is calculated (step 3116). For example, a 2D thermal model may be solved for real time temperature estimates assuming circular ablation lesion symmetry (step 3119). If the temperature is determined to be greater than desired as in step 3118, power is reduced (step 3120). If the temperature is less than desired, power is increased (step 3122). The watchdog timer is read at each step (step 3124). If the watchdog, timer is timed out, there has possibly been a software or hardware failure and the RF amplifier is turned off (steps 3126, 3128). If the watchdog timer is not timed out the step timer is incremented (step 3130). If the currently selected protocol or energy bolus step timer has elapsed (step 3132) a step counter is incremented, the timer is reset (step 3134) and the next step (3136) is loaded for execution. If the last step associated with a select bolus is finished (step 3138), the energy delivery is terminated (step 3128). The foregoing steps assure that an integrated system as described herein will only deliver a prescribed therapeutic dosage, also known as an energy bolus. Thus over-treatment or burns may be avoided, enhancing patient safety.

Figure 23C:
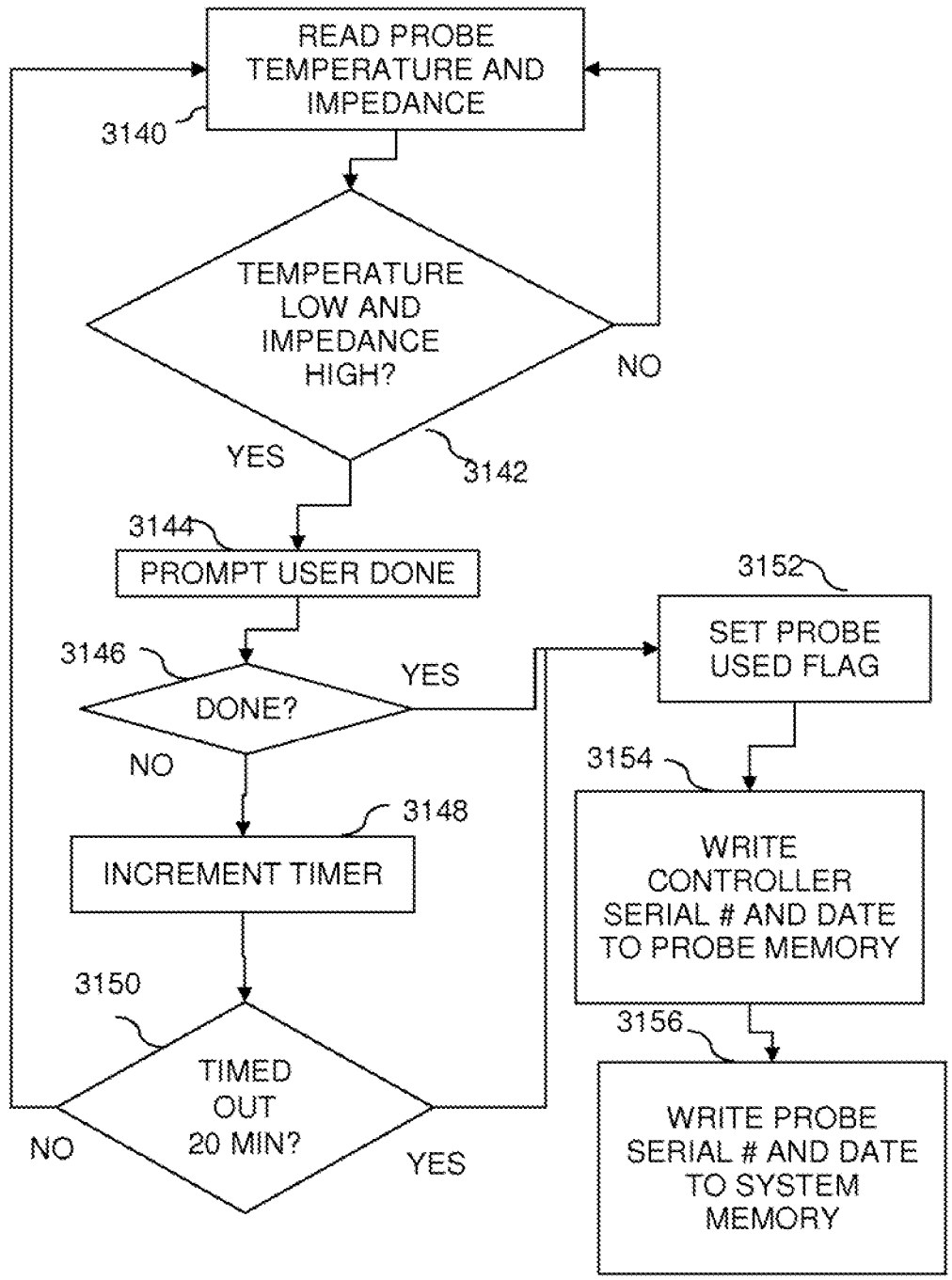
FIG. 23C is a flowchart illustrating certain aspects of a system management method consistent with the present invention.

As illustrated in FIG. 23C, upon completion of a procedure, the probe temperature and impedance is read (step 3140). High impedance and a temperature below body temperature (step 3142) indicate that the probe is removed from body and the operator is prompted by the system if done (step 3144). If no reply is received from the operator (step 3146), the timer is incremented (step 3148). If the timer has timed out (step 3150) or if an affirmative reply is received (step 3146), the probe used flag, is set (step 3152) in probe mentor 331 and the controller 400 serial number and date are written to probe memory (step 3154). Also the probe serial number, date, time, and any sampled treatment data are written to system memory (step 3156).

In summary, the steps illustrated on FIGS. 23A-C serve to verify that the probe is sterile (not used), properly calibrated and not defective. These steps also assure that the probe matches the current source or generator console, that the probe matches the certified treatment protocols for the practitioner and that the maximum treatment time dosage for a given treatment protocol is not exceeded. Thus the above steps assure that the probe and system are properly used to supply the selected treatment protocol, enhancing patient safety and treatment effectiveness.

Figure 24:
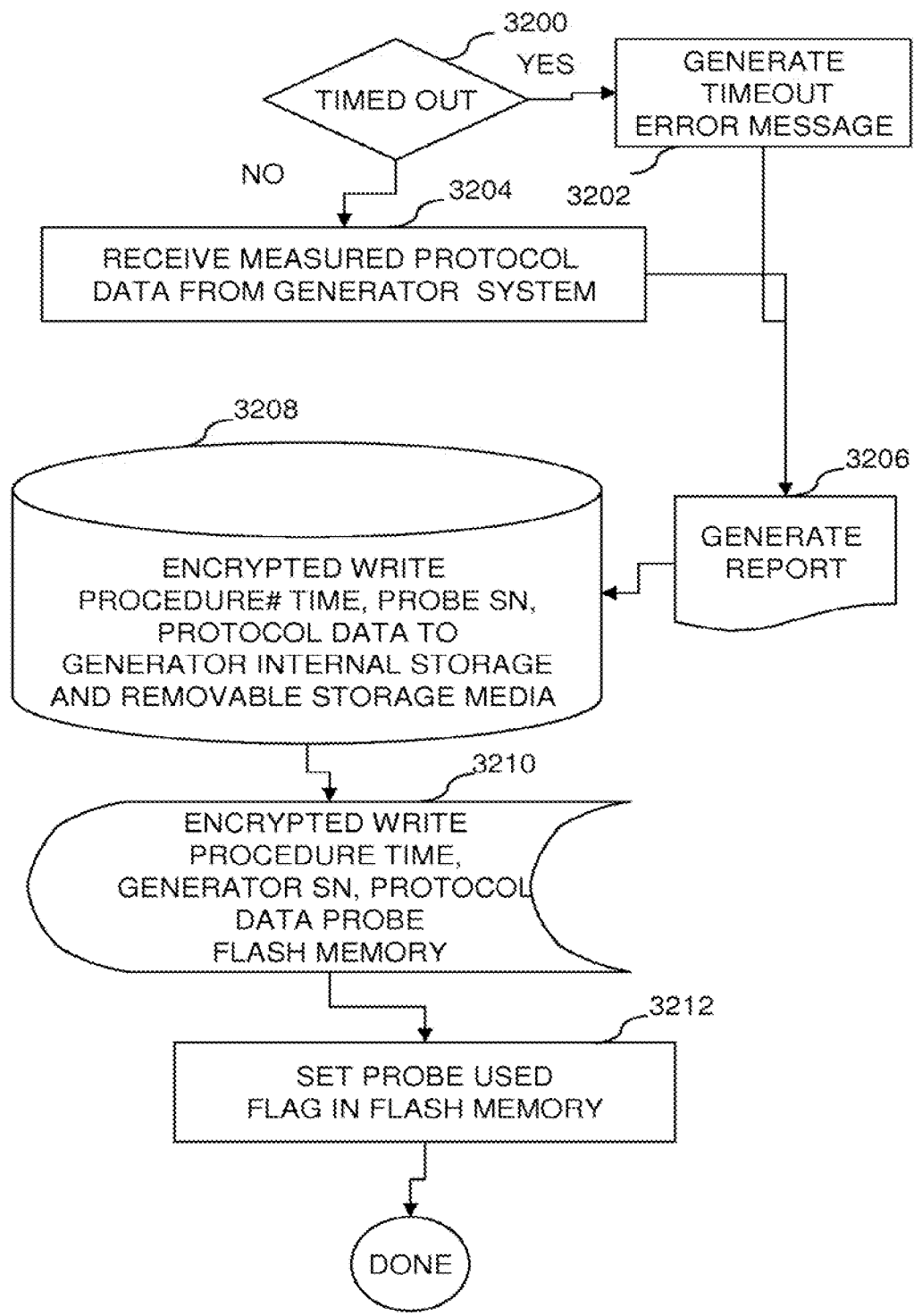
FIG. 24 is a flowchart illustrating certain aspects of a system management method consistent with the present invention.

FIG. 24 is a flowchart illustrating, a data writing procedure suitable for documenting information at the conclusion of the treatment procedure. If the selected probe has timed out during, the procedure, an error message is generated (step 3200, step 3202). Otherwise, procedure data is retrieved from the system and a report is generated (step 3204, step 3206) the report may be saved, or displayed on the user display 450 (See FIG. 1). The report may be encrypted (step 3210) and include, but not be limited to, the probe serial number, the procedure time/date, the therapeutic protocol(s) used, current source current and runtime data, temperatures, impedances and error messages. Similarly encrypted data may be written to the probe memory 331 (see FIG. 4), including but not limited to the system generator serial number, protocol, and date (step 3210). In addition, the probe-used flag must be set to a used status in the probe flash memory 331 (step 3212).

The system of the present invention is preferably implemented with an integrated and attractively packaged control console which includes within one or related multiple housings a stimulation current source, an ablation energy source, and a practitioner interface unit. See FIG. 1 for example. The practitioner interface, particularly if implemented as a computer style monitor, with or without touch screen capacity also provides for novel training and system use control methods. For example, the system may be used to store and display practitioner training, promotional and client multimedia files for each procedure/protocol. Interactive multimedia files may be included to instruct a practitioner in the numerous safety features, therapeutic protocol or energy bolus prescriptions and nerve location methods taught herein. Similar multimedia files may be used to teach the protocol system settings and location of anatomical landmarks. The training and other multimedia materials may be customized for each practitioner. Thus the fully integrated system described herein may be used to provide ongoing practitioner training thereby assuring patient safety and procedure effectiveness.

Therapeutic Treatment Protocols

As disclosed herein tissue ablation or a nerve block or other minimally invasive electrosurgical procedure may be performed with precisely applied RF energy. A fundamental requirement of the therapeutic RF waveform is to heat and denature human tissue in a small area over a selected time frame, for example, less than 25 seconds. Laboratory experiments indicate this to be a suitable time required to adequately ablate a small motor nerve. Longer or shorter treatment times may be required for other applications. The temperature required to denature the fine structure of the selected tissue, primarily proteins and lipids is approximately 65.degree. C. and above.

To safely achieve appropriate ablation, nerve block or other treatment goals, the RF waveform may be generated and applied to meet the following criteria: [0237] 1. The probe temperature will be limited to less than 160.degree. C. in order to prevent excess damage to collateral tissue areas.

[0238] 2. The probe temperatures will preferably be held to between 90.degree. and 105.degree. C.

1. The probe temperature will be limited to less than 60.degree. C. in order to prevent excess damage to collateral tissue areas.

2. The probe temperatures will preferably be held to between 90.degree. and 105.degree. C.

This range will prevent excessive tissue sticking as well as aid in the growth of an appropriate ablation lesion.

Initial RF power application should bring the temperature of the probe tip to a working therapeutic temperature in controlled manner, causing minimal overshoot. The time frame for the initial warming, phase may be between 0.2 to 2.5 seconds.

To achieve the foregoing generalized goals, specific treatment protocols may be developed. In one embodiment of the present invention, the delivery of a specific therapeutic protocol (also described as an "energy bolus") herein is automated. Automation can increase safety and treatment effectiveness since the practitioner may concentrate on probe placement while the system assures the delivery of the selected energy bolus. For example, the system controller 401 may be configured to control the waveform of energy supplied to an electrosurgical probe connected to the system in particular, the wave shape, waveform modulation or pulse time may be controlled. Also, the total time during which power may be applied and maximum power or voltage limits may be set. In addition, a specific treatment protocol may be actively controlled according to feedback such as the probe temperature, adjacent tissue temperature, tissue impedance or other physical parameters which may be measured during the delivery of treatment energy. Sped fie energy delivery prescriptions or energy boluses may be developed for specific treatment goals. These energy prescriptions may be stored in memory associated with the controller as a permitted therapeutic protocol. A representative therapeutic energy protocol 3250 is shown in tabular form on FIG. 25.

Figure 25:
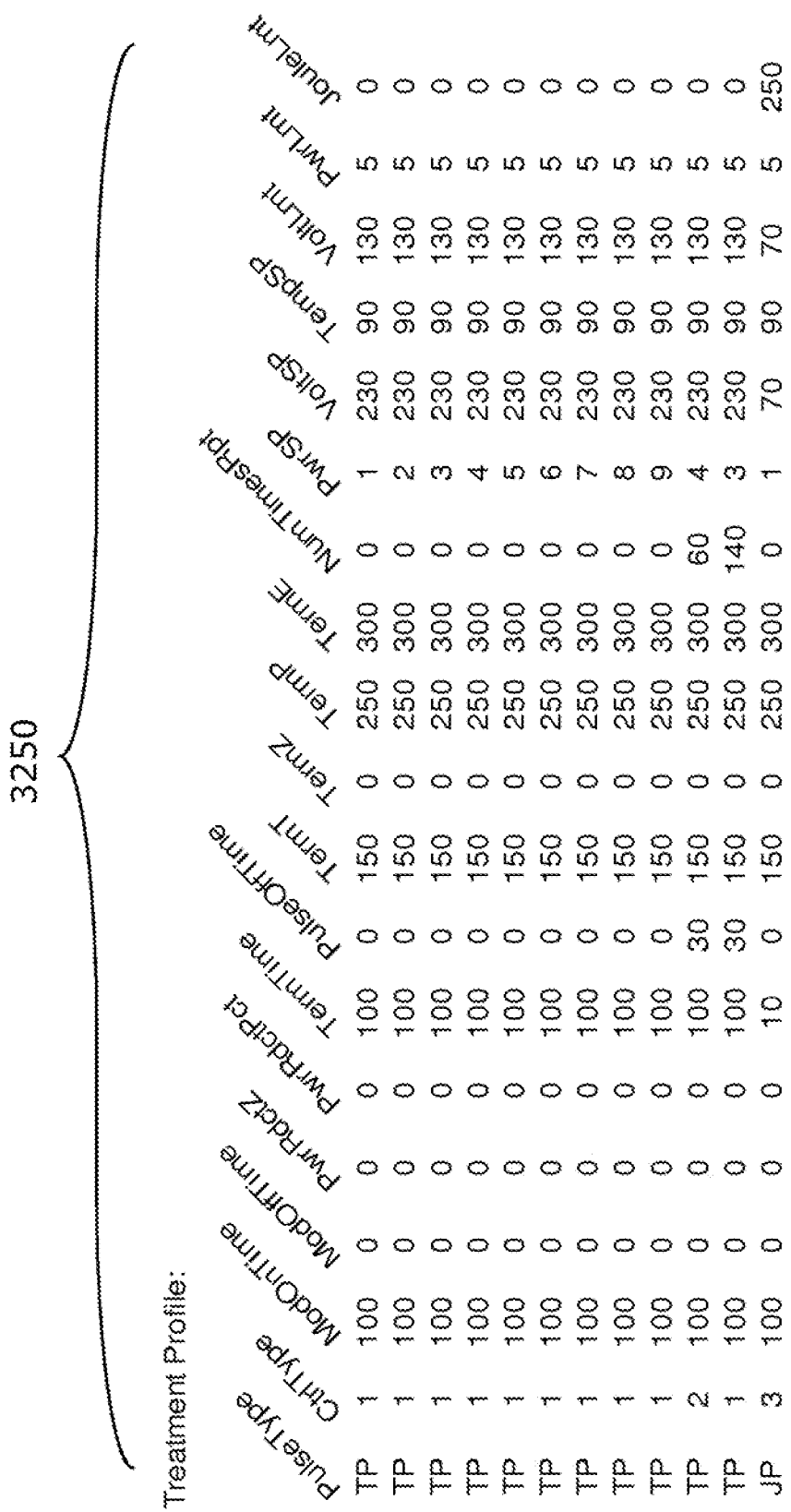
FIG. 25 is a tabular representation of a therapeutic energy protocol consistent with the present invention.

The therapeutic protocol 3250 of FIG. 25 is optimized for the therapeutic ablation of a human nerve having a diameter of approximately 1 millimeter. As shown on FIG. 26, the treatment protocol 3250 is generally designed to rapidly heat tissue during an initial phase 3252. Rapid heating during the initial phase has been shown to minimize perceived pain and reduce muscle stimulation from the subsequent application of pulsed RF energy. A second phase 3254 includes constant power application resulting in a slower ramp to a desired therapeutic tissue/probe temperature. As also shown on FIG. 26, a third phase 3256 includes the maintenance of a constant temperature at reduced power to grow the ablation lesion to a desired size.

Figure 26:
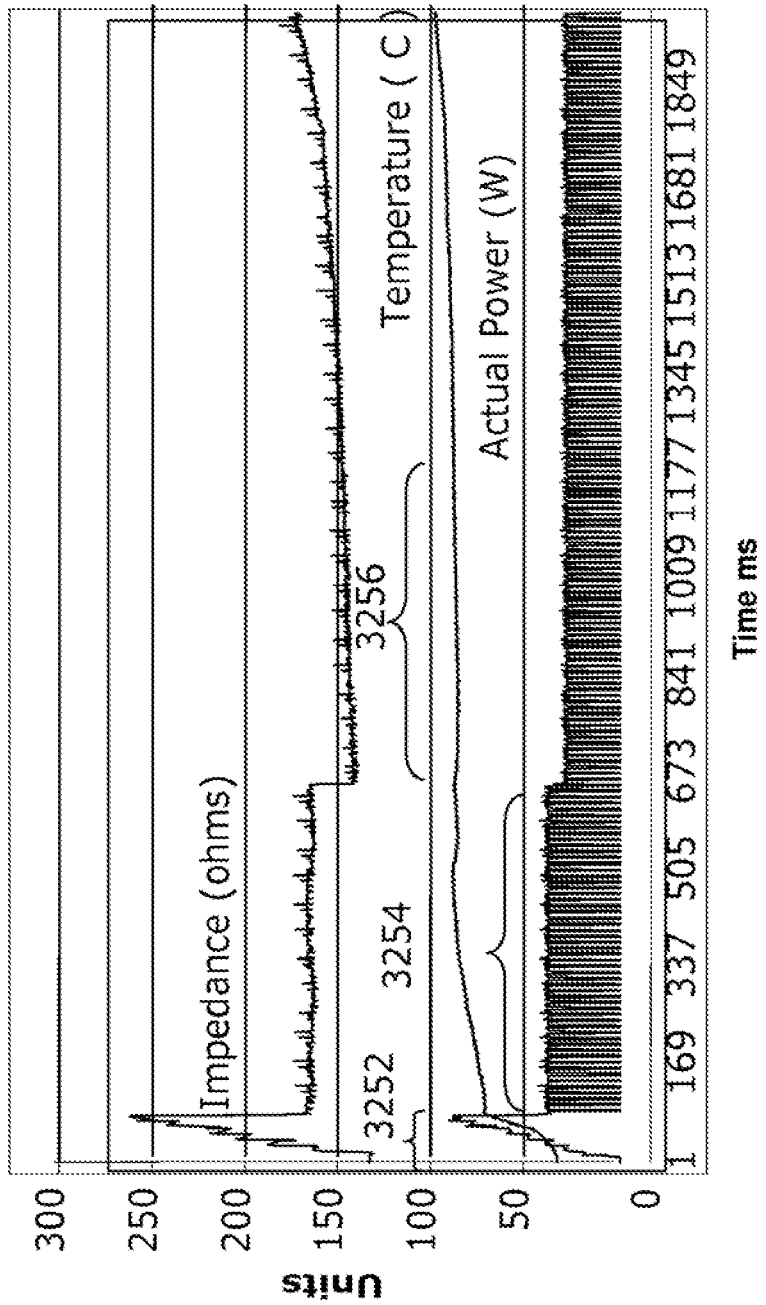
FIG. 26 is a graphic representation of a therapeutic energy protocol consistent with the present invention.

The therapeutic treatment protocol 3250 illustrated on FIGS. 25 and 26 is only one treatment protocol which has been found suitable for the ablation of a small motor nerve. Other treatment protocols may be developed for other or the same therapeutic goals. In all cases, the level of tissue ablation is substantially exponentially related to the product of time and temperature above 40.degree. C. as is well known in the art as the Arrhenius rate. Thermal heat transport through target tissue may be calculated with a finite difference algorithm. Tissue properties may be specified on a 2D mesh and such properties can be arbitrary functions of space and time Arrhenius rate equations may be solved for the extent of ablation caused by elevated temperatures. In addition, optical and electrical properties which are characteristic of ablated tissue may be measured and determined through histological studies. Thus, various therapeutic protocols such as that illustrated in FIGS. 25 and 26 may be developed and optimized for the controlled achievement of desired therapeutic results. Preferably the therapeutic protocols are automatically delivered to assure that the selected energy bolus is precisely delivered.

Figure 27:
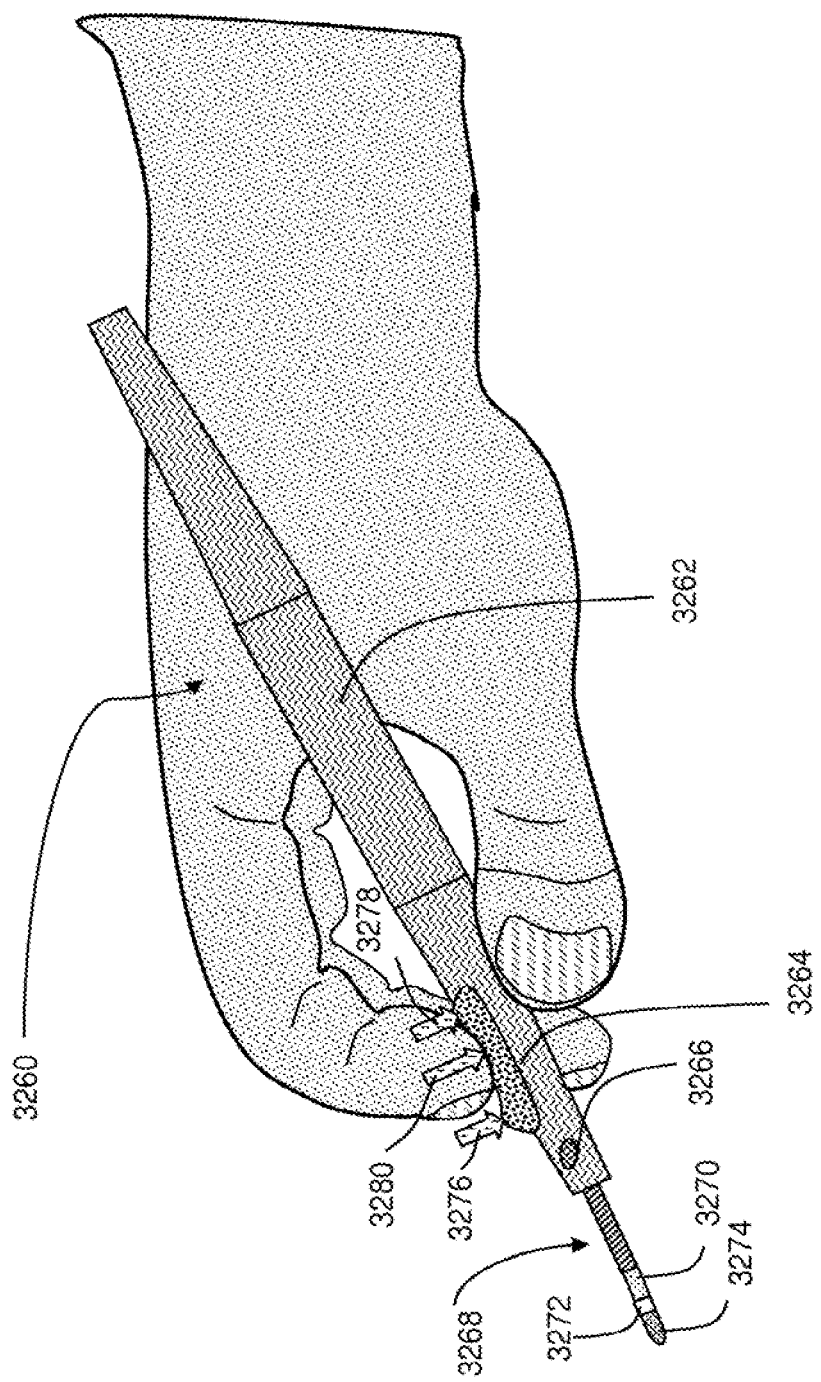
FIG. 27 is a perspective view of an electrosurgical probe featuring a multi-position switch to control stimulation current.

As described above, the system may be configured to deliver a prescribed energy bolus automatically. Automated energy delivery can increase safety and treatment effectiveness, since the practitioner is free to concentrate on probe placement. The goals of enhanced patient safety and treatment effectiveness can be further advanced by providing an ergonomically appropriate probe with associated switches and control functions providing the practitioner with a tool that allows him to easily and safely initiate the automated delivery of an energy bolus while concentrating on probe placement. For example, FIG. 27 is a perspective view of an electrosurgical probe 3260 consistent with the present invention held by practitioner's hand. The probe 3260 includes an ergonomic probe handle 3262 which is symmetrical allowing for left or right handed operation. A sealed rocker switch 3264 is located at the forward ⅓ of handle 3262 for operation with the practitioner's index finger or thumb. Although a rocker switch is shown in FIG. 27, other multi-function switch styles are suitable for the implementation of this aspect of the invention. A light indicator 3266 is installed on the handle 3262 near the probe needle 3268 to signal the system generator status. The needle has an exposed return electrode 3270, insulator 3272 and blunt active electrode 3274 in use, the blunt active electrode 3274 is inserted in proximity to a target nerve.

During the process of probe placement, the stimulation current level may be increased or decreased as described herein by sequentially depressing one of the forward or rearward sides of the rocker switch (see arrows 3276 and 3278) thus closing internal switches 314 and 315 respectively. A speaker associated with the system may emit a tone having a volume or frequency or other sound attribute substantially proportional to the amplitude setting of the stimulation current with each switch closure. This feature permits the practitioner to adjust the stimulation level without the necessity of adjusting any level dials or switches associated with the generator, allowing the practitioner to focus on critical probe placement.

When the stimulation process is complete, and the probe is positioned for treatment, the practitioner may depress switch 3264 at the center (see arrow 3280), thus closing both switches and commanding the generator to arm the ablation current source. It should be noted that the blunt tip embodiment permits iterative probe placement while minimizing the risk of cutting arteries or other structures as with a chisel or pointed tip. When the rocker switch is centrally depressed, the light 3266 may illuminate a select color, green for example, signaling to the practitioner that the system is ready to apply RF ablation energy. Without moving the probe, a pre-selected RF energy bolus may be delivered by closure of a foot switch (not shown). Light source 3266 may illuminate a different color, blue for example, during the application of RF ablation energy. In addition, the system generator may be configured to emit a tone signaling energy delivery. Thus, the disclosed probe and system may be used by a practitioner to skillfully implement one of the probe location and placement methods described herein, followed by the initiation of the automatic delivery of a selected energy bolus.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

We claim:

1. An electrosurgical probe comprising:
   a rigid probe body defining a central longitudinal probe axis,
   a single probe tip coupled to the probe body and disposed along the central longitudinal probe axis, wherein the probe tip is configured to produce a single point of puncture;
   multiple conductive electrodes coupled to the probe body, wherein the conductive electrodes are longitudinally coaxial with one another and axially spaced along the central longitudinal probe axis,
   and a dielectric insulator operatively disposed between the conductive electrodes,
   wherein, the conductive electrodes are in electrical communication with a radiofrequency energy source, with at least one additional conductive electrode spaced from either a first or a second conductive electrode,
   wherein, at least one of the conductive electrodes is in electrical communication with a stimulation current source that causes an observable response when applied; and
   wherein a surface area of at least the first conductive electrode and the second conductive electrode are similar such that application of ablation energy creates a heating zone having a symmetrical ellipsoid form.

2. The probe of claim 1, wherein the probe body is configured to be able to be moved laterally or in a circular manner during insertion to permit manipulation of the handle to reposition conductive region within a region of tissue.

3. The probe of claim 1, further comprising a temperature sensing element located between the first conductive electrode and the second conductive electrode.

4. The probe of claim 1, where the dielectric insulator comprises a tapered profile.

5. The probe of claim 1, further comprising an illumination source on a handle of the probe body.

6. The probe of claim 5, where the illumination source comprises a modulation flash rate proportional to the amount of stimulation energy.

7. The probe of claim 5, where the illumination source comprises a means to distinguish delivery of stimulation energy from delivery of ablation energy.

8. The probe of claim 1, further comprising a lumen operatively disposed along the length of the single axis probe.

9. The probe of claim 8 where the lumen is in communication with a fluid reservoir.

10. The probe of claim 1, wherein the probe is in communication with a controller configured to determine the impedance of the tissue surrounding the probe.

11. The probe of claim 1, wherein, the handle is enabled to switch between the radiofrequency source and the stimulation current source.

12. The probe of claim 11 wherein, the stimulation current source stimulates a motor nerve.

13. The probe of claim 1, wherein, the stimulation current source is between 1 milliamp and 20 milliamps.

14. The probe of claim 1, wherein, there is an LED on a handpiece of the probe body.

15. The probe of claim 1, wherein the switch is located as to allow use of the switch without repositioning of the hand of the handle.

16. The probe of claim 1, wherein the probe tip is conical.

17. An electrosurgical probe comprising:
   a rigid probe body defining a central longitudinal probe axis,
   a single probe tip coupled to the probe body and disposed along the central longitudinal probe axis, wherein the probe tip is configured to produce a single point of puncture;
   multiple conductive electrodes coupled to the probe body, wherein the conductive electrodes are longitudinally coaxial with one another and axially spaced along the central longitudinal probe axis, and where a portion of at least one electrode extends over the tip
   and a dielectric insulator operatively disposed between the conductive electrodes,
   wherein, the conductive electrodes are in electrical communication with a radiofrequency energy source,
   wherein, at least one of the conductive electrodes is in electrical communication with a stimulation current source that causes an observable response when applied.

18. The probe of claim 17, wherein a surface area of a first conductive electrode and a second conductive electrode are different.

* * * * *